US010964443B2

(12) United States Patent
Press et al.

(10) Patent No.: US 10,964,443 B2
(45) Date of Patent: Mar. 30, 2021

(54) CONDUCTIVE YARN

(71) Applicant: SP Nano Ltd., Yavne (IL)

(72) Inventors: Konstantin Press, Rishon-LeZion (IL);
Asa Eitan, Tel-Aviv (IL); Tamir Fine,
Petach-Tikva (IL); Michael Kaminsky,
Geva Binyamin (IL); Amnon Wolf,
Herzlia Pituach (IL)

(73) Assignee: SP Nano Ltd., Kibbutz Reshafim (IL)

( * ) Notice: Subject to any disclaimer, the term of this patent is extended or adjusted under 35 U.S.C. 154(b) by 0 days.

(21) Appl. No.: 16/073,790

(22) PCT Filed: Jan. 29, 2017

(86) PCT No.: PCT/IL2017/050106
§ 371 (c)(1),
(2) Date: Jul. 29, 2018

(87) PCT Pub. No.: WO2017/130203
PCT Pub. Date: Aug. 3, 2017

(65) Prior Publication Data
US 2019/0198191 A1    Jun. 27, 2019

(30) Foreign Application Priority Data
Jan. 28, 2016  (IL) .......................... 243839

(51) Int. Cl.
| | | |
|---|---|---|
| *H01B 1/24* | (2006.01) | |
| *C07K 14/415* | (2006.01) | |
| *D06M 15/15* | (2006.01) | |
| *D02G 3/44* | (2006.01) | |
| *D06M 11/74* | (2006.01) | |
| *D06M 11/83* | (2006.01) | |
| *D06M 15/61* | (2006.01) | |
| *C08J 7/04* | (2020.01) | |
| *D06M 23/08* | (2006.01) | |
| *C03C 25/54* | (2006.01) | |
| *H01B 3/30* | (2006.01) | |
| *H01B 5/14* | (2006.01) | |
| *H01B 13/00* | (2006.01) | |
| *D06M 101/32* | (2006.01) | |
| *D06M 101/36* | (2006.01) | |

(52) U.S. Cl.
CPC .............. *H01B 1/24* (2013.01); *C03C 25/54* (2013.01); *C07K 14/415* (2013.01); *C08J 7/042* (2013.01); *C08J 7/0427* (2020.01); *D02G 3/441* (2013.01); *D06M 11/74* (2013.01); *D06M 11/83* (2013.01); *D06M 15/15* (2013.01); *D06M 15/61* (2013.01); *D06M 23/08* (2013.01); *H01B 3/303* (2013.01); *H01B 5/14* (2013.01); *H01B 13/0036* (2013.01); *D06M 2101/32* (2013.01); *D06M 2101/36* (2013.01); *D10B 2101/122* (2013.01)

(58) Field of Classification Search
CPC ............................... H01B 1/24; C07K 14/415
See application file for complete search history.

(56) References Cited

U.S. PATENT DOCUMENTS

| | | | |
|---|---|---|---|
| 2,850,578 | A | 9/1958 | Gatzert |
| 3,791,932 | A | 2/1974 | Schuurs et al. |
| 3,839,153 | A | 10/1974 | Schuurs et al. |
| 3,853,987 | A | 10/1974 | Dreyer |
| 3,850,578 | A | 11/1974 | McConnell |
| 3,850,752 | A | 11/1974 | Schuurs et al. |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein |
| 3,984,533 | A | 10/1976 | Uzgiris |
| 3,996,345 | A | 12/1976 | Ullman et al. |
| 4,002,531 | A | 1/1977 | Royer |
| 4,179,337 | A | 12/1979 | Davis et al. |
| 4,666,828 | A | 5/1987 | Gusella |
| 4,683,202 | A | 7/1987 | Mullis |
| 4,801,531 | A | 1/1989 | Frossard |
| 5,073,292 | A | 12/1991 | Hessel et al. |
| 5,097,025 | A | 3/1992 | Benfey et al. |
| 5,192,659 | A | 3/1993 | Simons |
| 5,272,057 | A | 12/1993 | Smulson et al. |
| 6,472,505 | B1 | 10/2002 | Condon et al. |
| 7,131,474 | B2 | 11/2006 | Sandstrom |
| 7,253,341 | B2 | 8/2007 | Wang et al. |
| 7,284,583 | B2 | 10/2007 | Dheur et al. |
| 7,304,128 | B2 | 12/2007 | Jakota et al. |
| 7,318,464 | B2 | 1/2008 | Hahn et al. |
| 7,337,815 | B2 | 3/2008 | Spadone et al. |
| 7,354,877 | B2 | 4/2008 | Rosenberger et al. |
| 7,445,764 | B1 | 11/2008 | Kratz |

(Continued)

FOREIGN PATENT DOCUMENTS

| | | |
|---|---|---|
| EP | 0774512 | 5/1997 |
| JP | 04-263667 | 9/1992 |

(Continued)

OTHER PUBLICATIONS

Hu et al., 2007, A General Route to Prepare One- and Three-Dimensional Carbon Nanotube/Metal Nanoparticle Composite Nanostructures, Langmuir, 23: 6352-6357.*
Wang et al., 2006, Aspen SP1, An Exceptional Thermal, Protease and Detergent-Resistant Self-Assembled Nano-Particle, Biotechnology and Bioengineering, 95(1): 161-168.*
Zhu et al., 2013, Amperometric Immunosensor for Carbofuran Detection Based on MWCNTs/GS-PEI-Au and AuN Ps-Antibosy Conjugate, Sensors, 13: 5286-5301.*

(Continued)

*Primary Examiner* — Amber D Steele

(57) ABSTRACT

An electrically conductive yarn or film and method of manufacturing thereof in which a SP1/nanoparticle complex bound to the yarn or film serves as a platform for adhesion of a metallic coating.

17 Claims, 20 Drawing Sheets
Specification includes a Sequence Listing.

(56) References Cited

U.S. PATENT DOCUMENTS

| | | | |
|---|---|---|---|
| 7,528,186 B2 | 5/2009 | Halasa et al. | |
| 7,581,439 B2 | 9/2009 | Rensel et al. | |
| 8,957,189 B2 | 2/2015 | Wolf et al. | |
| 2002/0098999 A1 | 7/2002 | Gallop et al. | |
| 2003/0092624 A1 | 5/2003 | Wang et al. | |
| 2003/0106160 A1* | 6/2003 | Sun | C09B 67/0097 8/115.51 |
| 2004/0058457 A1 | 3/2004 | Huang et al. | |
| 2004/0173295 A1 | 9/2004 | Zanzig et al. | |
| 2005/0074763 A1 | 4/2005 | Wang et al. | |
| 2005/0263456 A1* | 12/2005 | Cooper | A61L 2/0082 210/660 |
| 2005/0277160 A1 | 12/2005 | Shiba et al. | |
| 2006/0074225 A1 | 4/2006 | Chamberlain | |
| 2006/0172298 A1 | 8/2006 | Wang et al. | |
| 2006/0240238 A1* | 10/2006 | Boussaad | B82Y 30/00 428/293.4 |
| 2007/0112174 A1 | 5/2007 | Shiba et al. | |
| 2007/0117147 A1 | 5/2007 | Jagota et al. | |
| 2007/0117148 A1 | 5/2007 | Jagota et al. | |
| 2007/0117150 A1 | 5/2007 | Jagota et al. | |
| 2010/0078103 A1 | 4/2010 | Nakamura | |
| 2010/0104868 A1 | 4/2010 | Lee | |
| 2012/0202397 A1* | 8/2012 | Wolf | H01B 1/24 442/111 |
| 2012/0312343 A1* | 12/2012 | VanVechten | H01L 35/22 136/201 |
| 2013/0302605 A1* | 11/2013 | Yang | D01F 9/12 428/368 |
| 2014/0044929 A1* | 2/2014 | Evans | B32B 3/266 428/190 |
| 2014/0178483 A1 | 6/2014 | Wolf et al. | |
| 2014/0227572 A1* | 8/2014 | Kwon | H01M 10/0525 429/94 |
| 2015/0299408 A1* | 10/2015 | Nguyen | C08J 5/24 428/300.1 |

FOREIGN PATENT DOCUMENTS

| | | |
|---|---|---|
| WO | WO 1999/033940 | 7/1999 |
| WO | WO 2000/076550 | 12/2000 |
| WO | WO 2001/009163 | 2/2001 |
| WO | WO 2002/015877 | 2/2002 |
| WO | WO 2002/049676 | 6/2002 |
| WO | WO 2002/070647 | 9/2002 |
| WO | WO 2004/022697 | 3/2004 |
| WO | WO 2007/007325 A2 | 1/2007 |
| WO | WO 2011/027342 A2 | 3/2011 |

OTHER PUBLICATIONS

Azadbakht et al., 2015, Immobilized organorutheniunn(II) complexes onto polyethyleneimine-wrapped carbon nanotubes/in situ formed gold nanoparticles as a novel electrochemical sensing platform, Materials Science and Engineering, 48: 270-278.*

Database WPI Week 199244 Thomson Scientific, London, GB; AN 1992-361800-XP002794218-JPH04263667 A (Achilles Corp)—Sep. 18, 1992—Abstract.

Katz, E. et al. (2004)—Integrated nanoparticle—biomolecule hybrid systems: synthesis, properties, and applications—Angewandte Chemie International Edition, 43(45), 6042-6108.

Lyashenko, T. et al.(2013)—Improved Mode II delamination fracture toughness of composite materials by selective placement of protein-surface treated CNT-Composites science and technology, 85, 29-35.

Medalsy, I. el al.(2008)—SP1 protein-based nanostructures and arrays—Nano letters, 8(2), 473-477.

Sarikaya, M. et al. (2003)—Molecular biomimetics: nanotechnology through biology—Nature materials, 2(9). 577-585.

Sequence 1 from U.S. Pat. No. 8,957,189.GenBank: AKW92032.1, Aug. 12, 2015.URL: https://www.ncbi.nlm.nih.gov/protein/915343807? report=genbank&log$=protalign&blast_rank=1&RID= 4AMRAGXP014.

Sequence 4 from U.S. Pat. No. 8,957,189.GenBank: AKW92035.1, Aug. 12, 2015.URL: https://www.ncbi.nlm.nih.gov/protein/915343810? report=genbank&log$=protalign&blast_rank=1&RID= 4AMK553J014.

Sequence 8 from U.S. Pat. No. 8,957,189.GenBank: AKW92038.1, Aug. 12, 2015.URL:https://www.ncbi.nlm.nih.gov/protein/915343813? report=genbank&log$=protalign&blast_rank=1&RID= 4AM28FSD015.

Sun, T. X. et al.(1999)—Thermodynamic stability of human lens recombinant αA- and αB-crystallins—Journal of Biological Chemistry, 274(48), 34067-34071.

Supplementary European Search Report for EP Application No. 17743855 dated Sep. 13, 2019.

Wang, W. X. et al.(2002)—Characterization of SP1, a stress-responsive, boiling-soluble, homo-oligomeric protein from aspen—Plant Physiology, 130(2), 865-875.

Willner, I.(2002)—Biomaterials for sensors, fuel cells, and circuitry-Science, 298(5602), 2407-2408.

Bachilo et al. "Structure-assigned optical spectra of single-walled carbon nanotubes" science. Dec. 20, 2002;298(5602):2361-6.

Chiang et al. "Purification and characterization of single-wall carbon nanotubes (SWNTs) obtained from the gas-phase decomposition of CO (HiPco process)" The Journal of Physical Chemistry B. Sep. 6, 2001;105(35):8297-301.

Dgany et al. "The structural basis of the thermostability of SP1, a novel plant (Populus tremula) boiling stable protein" Journal of Biological Chemistry. Dec. 3, 2004;279(49):51516-23.

Dyke et al. Separation of single-walled carbon nanotubes on silica gel. Materials morphology and Raman excitation wavelength affect data interpretation. Journal of the American Chemical Society. Mar. 30, 2005;127(12):4497-509.

Eitan et al. "Non-Toxic Reinforcement Textile for Tires and Mechanical Rubber Goods", Rubber World, vol. 254, No. 6, Sep. 1, 2016 (Sep. 1, 2016), pp. 24-27, XP00951310.

Holten-Andersen et al. "Mussel-designed protective coatings for compliant substrates" Journal of dental research. Aug. 2008;87(8):701-9.

International Search Report for PCT Application No. PCT/IL2017/050105 dated May 3, 2017.

Kase et al. "Affinity selection of peptide phew libraries against single-wall carbon nanohorns identifies a peptide aptamer with conformational variability" Langmuir. Sep. 28, 2004;20(20):8939-41.

Pender et al. "Peptide-mediated formation of single-wall carbon nanotube composites" Nano letters. Jan. 11, 2006;6(1):40-4.

Sano et al. "A hexapeptide motif that electrostatically binds to the surface of titanium" Journal of the American Chemical Society. Nov. 26, 2003;125(47):14234-5.

Sano et al. "Utilization of the plelotropy of a peptidic aptamer to fabricate heterogeneous nanodot-containing multilayer nanostructures" Journal of the American; Chemical Society. Feb. 8, 2006;128(5)1717-22.

Sano et al. "In aqua structuralization of a three-dimensional configuration using biomolecules" Nano letters. Oct. 10, 2007;7(10):3200-2.

Sarikaya et al. "Molecular biomimetics: nanotechnology through biology" Nature materials. Sep. 2003;2(9):577-85.

Supplementary European Search Report for European Application No. 17743854.6 dated Jul. 24, 2019.

Wang et al. "Aspen SP1, an exceptional thermal, protease and detergent-resistant self-assembled nano-particle" Biotechnology and bioengineering. Sep. 5, 2006;95(1):161-8.

Wang et al. "Peptides with selective affinity for carbon nanotubes" Nature materials. Mar. 2003;2(3):196-200.

Weisman et al. "Dependence of optical transition energies on structure for single-walled carbon nanotubes in aqueous suspension: an empirical Kataura plot" Nano letters. Sep. 10, 2003;3(9)1235-8.

Wolf et al. "Improved adhesives containing CNT/SP1 nano fillers" The Journal of Adhesion. Apr. 1, 2012:88(4-6):435-51.

* cited by examiner

CONDUCTIVE YARN

CROSS-REFERENCE TO RELATED APPLICATIONS

This application is a National Phase Application of PCT International Application No. PCT/IL2017/050106, International Filing Date Jan. 29, 2017, claiming priority from IL Patent Application(s) No(s). 243839, filed Jan. 28, 2016, which are hereby incorporated by reference in their entirely.

BACKGROUND OF THE INVENTION

The present invention relates to the enablement of non-metallic yarns, fabrics and films as electrical conductors by supporting a coating of conductive metal with a Stable Protein (SP1) nanoparticle matrix bound to the fabric or film material.

Stable Protein 1 (SP1)

Stable protein 1 (SP1) is a homo-oligomeric protein isolated from aspen (*Populus tremula aspen*) plants and forms a ring-shape dodecameric particle with a central cavity. The oligomeric form of SP1 is an exceptionally stable structure that is resistant to proteases, such as trypsin, V8, and proteinase K, high temperatures, organic solvents, and high levels of ionic detergent.

Carbon Nanoparticles (CNP) Reinforced Composite Materials

Although the present invention relates both to carbon and non-carbon nanoparticles, without diminishing in scope carbon nanoparticles will be discussed herewithin.

Carbon nanotubes are nano-scale hollow cylinders of graphite carbon atoms. They provide the highest Young's modulus (stiffness), highest thermal conductivity, highest electrical conductivity, and highest current density of any known material, while having a low density. The nanotubes may consist of one (single walled carbon nanotubes) up to tens (multi-walled CNTs) and hundreds of concentric shells of carbons with adjacent shells separation of ~0.34 nm. Single walled carbon nanotubes tend to be stronger, more flexible, more transparent and better electrical conductors and are more transparent. High production costs plus health and safety considerations have led to multi-walled carbon nanotubes being more widely used in composite materials.

When carbon nanotubes are added to a matrix material the composite normally takes on some of the carbon nanotubes' properties, due to the rule of mixtures. However, the theoretical property values of carbon nanotubes composites are presently not attained due to the inability to efficiently produce fully integrated composites.

SP1 variants capable of forming molecular complexes with carbon nanotubes address the insufficient bonding across the interface of the nanotube and matrix material.

Carbon Nanoparticles Binding with Fabrics

Carbon Nanoparticles possess much larger surface specific area than fibers, fabrics, or films, and is therefore a desirable platform for loading conductive metals. SP1 protein facilitates binding of CNP with the fibers, even when low loading levels of SP1 are employed. SP1 binding to the fiber has been found to be enhanced through a prior application of a polymeric coating on the fiber via bonding of reactive groups of the protein.

Specifically designed SP1/CNP compositions (Also referred to as matrices and complexes) utilizing carbon black (CB), carbon nanotubes (CNT) of either graphene or graphite form stable dispersions in solvents. They may be complexed to a broad range of target compounds such as carbon fabrics, aramid, polyester, or nylon fibers, yarns, films, fabrics, and also glass fiber fabrics to form useful molecular complexes in the production of highly specific composite materials such as SP1-polypeptide-CNP-aramid complex fabrics, films, yarns and polymeric fabrics.

Carbon Nanoparticles Binding with Aramid Polymers (Kevlar)

As is well-known in the art, aramid (e.g. KEVLAR™) is chemically inert and is not soluble in any common solvent, has a very high melting point, and decomposes above 400° C. As a result, aramid fibers must be produced by wet spinning from sulfuric acid solutions. Binding of SP1/CNP complex to aramid can facilities the adhesion of carbon nanoparticles (e.g., CNT or CB) onto pre-formed polymer products like KEVLAR™ yarns.

Electrical Conductivity

The SP1/CNP complex further provides a platform for bonding electrically conductive metals to yarn or fabric. To date, conductive fabrics have been constructed by spinning metallic yarn together with staple yarn or, in the production of conductive fabric, incorporating metallic wire or mesh into fabric. The SP1/CNP platform advantageously facilities scalable processing schemes and highly efficient use of metallic materials by exhausting the metallic solutions from their metallic content during conductive coating processes. The SP1/CNP platform further provides flexibility and shape memory functionality.

SUMMARY OF THE INVENTION

According to the teachings of the present invention there is provided a conductive yarn including a plurality of interlocked fibers; at least partially coated with a composition of carbon nanoparticle and SP1 based polypeptide (SP1/CNP); one or more polyamine coatings; and an outer metal coating.

According to a further feature of the present invention, wherein the polyamine coatings are implemented as a first polyamine coating sandwiched between the fiber and the composition of the SP1/CNP and a second polyamine coating between the composition and the outer metal coating.

According to a further feature of the present invention, there is also provided an inner metal coating disposed between the second polyamine coating and the outer metal coating.

According to a further feature of the present invention, the SP1 based polypeptide is non-covalently bound to the carbon nanoparticle.

According to a further feature of the present invention, the SP1 based polypeptide is characterized by at least 85% amino acid homology to SEQ ID NO:1 (wild type); and stable dimer-forming capability.

According to a further feature of the present invention, the SP1 based polypeptide is further characterized by at least one conserved amino acid sequence in at least one region corresponding to amino acids 9-11, 44-46 and/or 65-73, of SEQ ID NO:4.

According to a further feature of the present invention, the SP1 based polypeptide is a chimeric SP1 polypeptide characterized by at least 85% amino acid homology to SEQ ID NO:1; stable dimer-forming capability; at least one conserved amino acid sequence in at least one region corresponding to amino acids 9-11, 44-46 and/or 65-73, of SEQ ID NO:4; and a carbon surface binding peptide at the N-terminus of the SP1 polypeptide.

According to a further feature of the present invention, the carbon surface binding peptide has an amino acid sequence selected from the group consisting of SEQ ID NOs: 10-13.

According to a further feature of the present invention, the SP1 base polypeptide has the amino acid sequence as set forth in any one of SEQ ID NOs: 3, 4, 6, 8, 9, 14-18 and 86.

According to a further feature of the present invention, the chimeric SP1 polypeptide has the amino acid sequence as set forth in any one of SEQ ID NOs: 6, 8, 9, 14-18 and 86.

According to a further feature of the present invention, the chimeric SP1 polypeptide has the amino acid sequence as set forth in SEQ ID NO: 8.

According to a further feature of the present invention, the carbon nanoparticle is implemented as either conductive carbon black, non-conductive carbon black, or carbon nanotube.

According to a further feature of the present invention, the outer metal coating is implemented as a copper coating.

According to a further feature of the present invention, the inner metal coating is as Pd(I), Pt(II), Rh(I), Ir(I), iron, aluminum, gold, silver, nickel, or combination thereof.

According to a further feature of the present invention, the fiber is selected from the group consisting of cotton fiber, wool fiber, silk fiber, glass fiber, nylon fiber, polyester fiber, aramid fiber, polyethylene fiber, poly-olefin fiber, polypropylene fiber, and elastane fiber.

According to a further feature of the present invention, wherein the load of the SP1/CNP on the yarn is between 0.01 gr/kg and 100 gr/kg.

According to a further feature of the present invention, the load of the SP1/CNP on the plurality of fibers is between 5 gr/kg and 15 gr/kg.

According to a further feature of the present invention, the load of the SP1/CNP on the plurality of fibers is between 7 gr/kg and 14 gr/kg.

According to a further feature of the present invention, the CNP:SP1 ratio is between 0.1:1 to 30:1 dry w/w.

According to a further feature of the present invention, the CNP:SP1 ratio is between 2.5:1 to 8:1 dry w/w.

According to a further feature of the present invention, the CNP:SP1 ratio is between 5:1 to 7:1 dry w/w.

According to a further feature of the present invention, the yarn has a twist range of at least 10 winds/meter.

According to a further feature of the present invention, the outer metal coating has a thickness of between 0.01 µm and 100.0 µm.

According to a further feature of the present invention, the yarn has a resistance between 0.001 Ω/m to 1000 mega Ω/m.

According to a further feature of the present invention, the polyamine includes polyethyleneimine (PEI).

According to a further feature of the present invention, there is further provided a polymeric coating on the outer metal coating.

There is also provided according to the teachings of the present invention, a method of producing the conductive yarn, including contacting a plurality of fibers with a polyamine so as to form a plurality of polyamine coated fibers; contacting the polyamine coated fibers with a dispersion comprising an SP1/CNP complex so as to form a plurality of complex coated fibers; and contacting the plurality of complex coated fibers with a metal, so as to form plurality of metal coated fibers.

According to a further feature of the present invention, there is also provided at least one step of washing the yarn with a buffer or water after each step of the method.

According to a further feature of the present invention, the each step of contacting is implemented in a textile dying machine or a bath.

According to a further feature of the present invention, the dispersion includes an SP1/CNP composition in a concentration of between 0.001% and 50% w/w.

According to a further feature of the present invention, the dispersion comprises an SP1/CNP composition is in a concentration of 0.05%, 0.1%, or between 0.05% and 0.15%.

According to a further feature of the present invention, the dispersion comprises an SP1/CNP composition is in a concentration of between 1% and 20% w/w.

According to a further feature of the present invention, the dispersion comprises an SP1/CNP composition is in a concentration of 2%, 4%, 6%, or 8% w/w.

According to a further feature of the present invention, the PEI is applied to the yarn at a load of 0.0035% to 30% w/w.

According to a further feature of the present invention, the PEI is applied to the yarn at a load of 0.007% to 0.7% w/w.

According to a further feature of the present invention, the PEI is applied to the yarn at a load of about 0.35% w/w.

According to a further feature of the present invention, the method is performed at a temperature between 4°-90° C.

According to a further feature of the present invention, the metallic catalyst is implemented as Pd(II), Pt(II), Rh(I), Ir(I), Cu(II) or any combination thereof.

According to a further feature of the present invention, the metallic catalyst is implemented as a combination of Pd(II) and Cu(II).

According to a further feature of the present invention, the ratio between Pd(II) and Cu(II) is 1:10.

According to a further feature of the present invention, the metallic catalyst is iron, gold, silver, nickel platinum, aluminum, or any combination thereof.

According to a further feature of the present invention, there is also provided comprising applying an outer metallic coating of copper outside of the metallic catalyst coating the fibers.

According to a further feature of the present invention, contacting the plurality of fibers with a metallic catalyst is implemented in a time span ranging from 5 seconds to 1 hour.

According to a further feature of the present invention, there is further provided a step of drying the fibers after contacting the metal catalyst.

According to a further feature of the present invention, there is further provided reducing the metallic catalyst to its metallic state.

According to a further feature of the present invention, the CNP of the SP1/CNP complex is implemented as conductive carbon black ($CB_{max}$).

According to a further feature of the present invention, there is further provided applying a polymeric coating onto the outer metallic coating of copper.

There is also provided according to the teachings of the present invention, conductive yarn including a plurality of interlocked fibers at least partially coated with a composition of carbon nanoparticle and SP1 based polypeptide (SP1/CBmax); one or more polyamine coatings; and an outer metal coating.

According to a further feature of the present invention, there is further provided a polymeric coating on the outer metal coating.

According to a further feature of the present invention, the polyamine coatings are implemented as a first polyamine coating sandwiched between the fiber and the composition of the SP1/CNP and a second polyamine coating between the composition and the outer metal coating.

There is also provided according to the teachings of the present invention, a polymeric film coated at least partially coated with a composition of carbon nanoparticles (CNP) and SP1 based polypeptide (SP1/CNP); a plurality of polyamine coatings; and a first metal coating disposed on the polyamines coating.

According to a further feature of the present invention, the polyamine coatings are implemented as a first polyamine coating sandwiched between the film and the composition and a second polyamine coating between the composition and the first metal coating.

According to a further feature of the present invention, there is also provided a second metal coating disposed between the second polyamine coating and the first metal coating.

According to a further feature of the present invention, the CNP includes conductive $CB_{max}$.

BRIEF DESCRIPTION OF THE DRAWINGS

The subject matter regarded as the invention is particularly pointed out and distinctly claimed in the concluding portion of the specification. The invention, however, the invention and its method of production, features, and advantages is best understood in reference to the following detailed description and accompanying drawings in which:

Figure 1A:
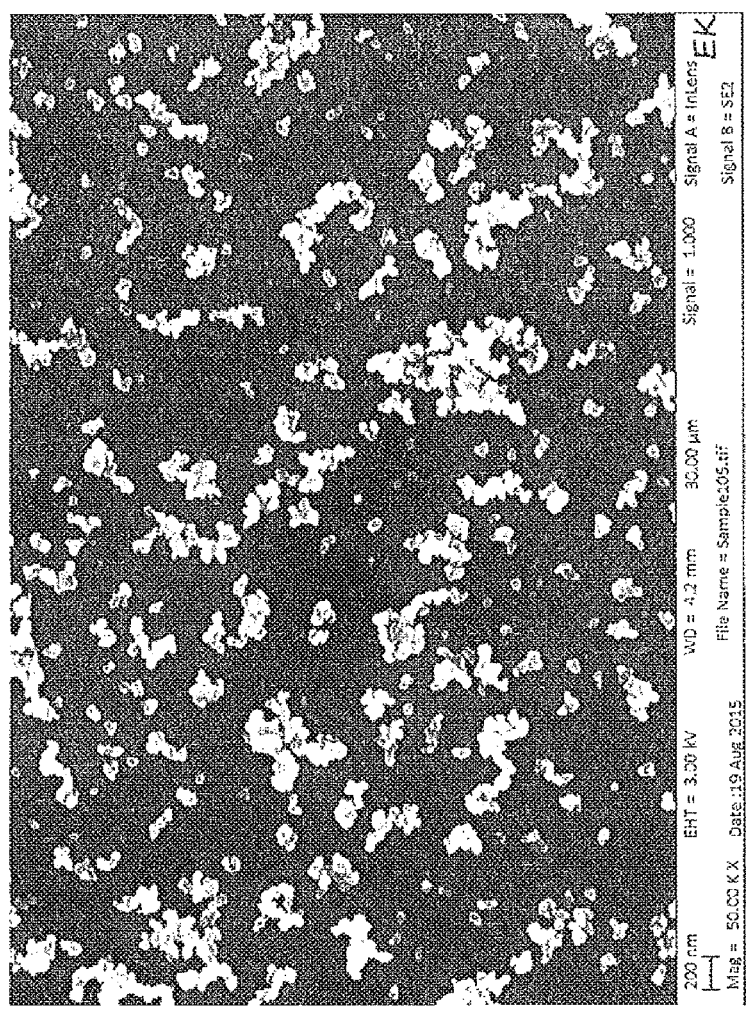
FIGS. 1A and 1B are high resolution scanning electron microscope images of SP1/CB (N326) dispersion and polymeric fiber coated with the SP1/CB (N326) complex, respectively.

It will be appreciated that for the sake of clarity, elements shown in the figures have not necessarily been drawn to scale. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. It should be understood that the invention includes combinations of features set forth in various embodiments. Also, it is to be understood that the phraseology and terminology employed herein is for the purpose of description and should not be regarded as limiting.

The present invention relates to conductive non-metallic polymeric or glass materials having metallic coating and structurally reinforcing SP1/CNP complex providing a platform for bonding of electrically conductive metals.

The SP1/CNP complex may be implemented as any of several SP1 variants complexed with carbon black or carbon nanotubes, or both.

SP1 polypeptide is an exceptionally stable polypeptide, forming hetero- and homo-oligomers which are resistant to denaturation by heat and most chemical denaturants, resistant to protease digestion, and capable of stabilizing molecular interactions and forming three dimensional structures (Dgany et al, JBC, 2004; 279:51516-23, and U.S. Pat. No. 7,253,341 to Wang et al)

SP1 Based Polypeptides

The bi- and multi-functional binding properties of chimeric SP1 polypeptides bind to fibers, films and fabrics and can be used to modify the physical properties of fibers, films and fabrics such as aramid (Kevlar™ and Twaron™), silk, polyester, glass-fiber, polyamide, cotton, nylon, and carbon fibers.

SP1 based polypeptides can be used as a protein scaffold for the presentation of surface active moieties. A versatile protein scaffold should generally constitute a conformationally stable folding entity that is able to display a multitude of loop structures or amino-acid sequences in a localized surface region. SP1 can be engineered to display various moieties contributing to their binding capability in a cooperative manner. Moreover, peptide exposure can be manipulated under solvent conditions that reduce non-specific binding.

Thus, according to one aspect of the present invention the SP1 based polypeptide comprised in the composition of matter according to this invention is characterized by: i) at least 65% amino acid homology to native SP1 (SEQ ID NO: 4); and ii) stable dimer-forming capability.

According to another aspect of the present invention the composition of matter according to this invention comprises isolated chimeric polypeptides comprising an SP1 polypeptide and a target binding peptide, wherein the SP1 polypeptide is characterized by: i) at least 65% amino acid homology to native SP1 (SEQ ID NO: 4); ii) stable dimer-forming capability; and iii) at least one conserved amino acid sequence in at least one region corresponding to amino acids 9-11, 44-46 and/or 65-73, of SEQ ID NO:4.

As used herein the phrase "SP1 based polypeptide" refers to a protein having at least the following characteristic properties: at least 65% sequence homology to SEQ ID NO:4; and being capable of forming stable dimers. In another embodiment, the phrase refers to a protein having at least the following characteristic properties: at least 65% sequence homology to SEQ ID NO:4; being capable of forming stable dimers, and having at least one conserved amino acid sequence in at least one region corresponding to amino acids 9-11, 44-46 and/or 65-73, of SEQ ID NO:1, as determined using a Best Fit algorithm of GCG, Wisconsin Package Version 9.1, using a plurality of 10.00, a threshold of 4, average weight of 1.00, average match of 2.91 and average mismatch of minus 2.00. In some embodiments, the SP1 polypeptide has conserved consensus sequences: "HAFESTFES" (65-73, SEQ ID NO:1), "VKH" (9-11, SEQ ID NO:1) and "KSF" (44-46, SEQ ID NO:1). According to one embodiment of the invention, "wild-type" or "native" SP1 is the stress related SP1 protein from aspen (SEQ ID NO:4), as disclosed by Wang et al (U.S. patent application Ser. No. 10/233,409, filed Sep. 4, 2002, now U.S. Pat. No. 7,253,341, issued Aug. 7, 2007, which is a Continuation in Part of PCT IL 02/00174, filed Mar. 5, 2002, both of which are incorporated by reference as if fully set forth herein.). The term "SP1 based polypeptide" refers in the context of this invention also to chimeric SP1 based polypeptide, i.e., polypeptides comprising an SP1 based polypeptide and a non-SP1 oligo- or polypeptide. In one embodiment, the SP1 based polypeptide is the crude SP1, i.e., is the heat stable fraction of the crude extract obtained from the bacteria that expressed it. In another embodiment, the SP1 based polypeptide is the pure SP1, obtained by further purification of the heat stable fraction of the crude extract expressed by the bacteria.

In one embodiment, the SP1 based polypeptide comprised in the composition of matter according to this invention is 70%, 75%, 80%, 85%, 90%, 95%, or up to 100% homologous to SEQ ID NO: 4. It will be appreciated that SP1 homologues have been identified in plant species other than aspen, and that these SP1 homologues can be suitable for use with the present invention, when fulfilling the abovementioned criteria.

The SP1 based polypeptide comprised in the composition of matter according to this invention, can be native SP1 (for example, SEQ ID NO: 4), or can be a chimera, i.e., an SP1 polypeptide having a modified amino acid sequence. In some embodiments modified SP1 polypeptides retain the above-mentioned activities of native SP1 polypeptide such as ability of forming oligomer and complexes that are pH-stable, hear-stable and denaturant- and protease-resistant.

As mentioned hereinabove, SP1 variant polypeptides can be modified to impart specific properties to the SP1 variant, thereby rendering the molecular complexing with, and release of other substances more efficient and controllable, and adaptable to specific conditions. Dgany et al (JBC 2004 279:51516-523) have identified a number of structurally significant regions in the SP1 polypeptide.

In some embodiments, the chimeric SP1 polypeptides contemplated in the composition of matter of this invention include, but are not limited to, modifications to side chains, incorporation of unnatural amino acids and/or their derivatives during peptide synthesis and the use of cross-linkers and other methods which impose conformational constraints on the peptides or their analogues.

According to one embodiment of the present invention any type of SP1 based polypeptide, may bind carbon fibers or surfaces. Thus, SP1 wild type or chimeric polypeptides can be used to bind carbon nanoparticles (e.g., carbon nanotubes, carbon black) and/or graphitic surfaces. Thus, according to further aspects of the present invention there is provided a composition comprising wild type SP1 protein and a carbon nanotube, carbon black, or graphitic surfaces. According to further aspects of the present invention there is provided a chimeric polypeptide comprising an SP1 based polypeptide and a carbon nanotube, carbon black, or graphitic surfaces binding peptide, and a carbon nanotube, carbon black, or graphitic surface.

According to one embodiment of the present invention the target binding peptide binds carbon nanoparticles or carbon surfaces. Thus, the chimeric polypeptides can be used to bind carbon nanoparticles (e.g., carbon nanotubes, carbon black) and/or graphitic surfaces. Thus, according to further aspects of the present invention there is provided a chimeric polypeptide comprising an SP1 based polypeptide and a carbon nanotube, carbon black, or graphitic surfaces binding peptide. Carbon nanotube binding peptides suitable for use with the chimeric polypeptide of the invention are well known in the art, for example, the peptides disclosed in U.S. Pat. No. 7,304,128 to Jagoda et al. According to some embodiments, the carbon nanotube, carbon black or graphitic surfaces binding peptide is HWSAWWIRSNQS (SEQ ID NO: 10), HSSYWYAFNNKT (SEQ ID NO: 11), DYFSSPYYEQLF (SEQ ID NO:12) or SNQS (SEQ ID NO:13) and the chimeric SP1 based polypeptide has an amino acid sequence as set forth in SEQ ID NOs:6, 8, 9 and 14-18. In certain embodiments, the carbon nanotube, carbon black or graphitic surfaces binding peptide is located at the N-terminus of the SP1 polypeptide.

In some embodiments, peptides that non-specifically bind to materials can be used in the chimeric SP1 based polypeptides comprised in the composition of matter according to this the invention. These include, but are not limited to repeated tyrosine rich motifs from specific mussel proteins (mfp1), where the tyrosine residues may be converted to L-DOPA (L-3,4-dihydroxyphenylalanine) (Holten-Andersen & Waite J Dent Res 87(8):701-709, 2008), such as AKPSYPPTYK, (SEQ ID NO: 20), AKPTYK (SEQ ID NO: 21), PKISYPPTYK (SEQ ID NO: 22), APPPAXTAXK (SEQ ID NO: 23), ATPKPXTAXK (SEQ ID NO: 24), PYVK (SEQ ID NO: 25), AKPSPYVPTGYK (SEQ ID NO: 26), GQQKQTAYDPGYK (SEQ ID NO: 27).

As used herein, a "chimeric polypeptide" refers to an amino acid sequence having two or more parts which generally are not found together in a single amino acid sequence in nature. Chimeric SP1 based polypeptides are defined herein as polypeptides comprising an SP1 based polypeptide and a non-SP1 oligo- or polypeptide having binding affinity for target molecules such as carbon nanoparticles (e.g., carbon black, carbon nanotubes, etc.) metals and other ions, the SP1 polypeptide and the non-SP1 component connected through a peptide bond.

Surprisingly, it was uncovered that SP1-CBD fusion protein binds fibers, fabrics and fabric substrates, as well as to carbon nanotubes with high affinity. Thus, according to one aspect of the present invention there is provided a composition of matter comprising an SP1-CBD chimeric polypeptide complexed with carbon nanotubes. According to another aspect there is provided a composition of matter comprising an SP1-CBD chimeric polypeptide complexed with carbon black.

The SP1-CBD chimeric polypeptide complexed with carbon nanotubes or carbon black can be used to incorporate carbon nanotubes or carbon black into textiles, yarns, fabrics and the like. Thus, in one embodiment, there is further provided an SP1-CBD chimeric polypeptide-CNT-complexed polymer, fiber, film, fabric or polymeric fabric. In another embodiment, there is further provided an SP1-CBD chimeric polypeptide-CB-complexed polymer, fiber, film, fabric or polymeric fabric.

The chimeric SP1 polypeptides of the present invention can also be used to bind carbon nanotube, carbon black and/or graphite surfaces.

Preferred SP1 based polypeptides to be used in composition of matter according to this invention include SP1 protein extracts represented by: SEQ ID NO: 4 (WT), SEQ ID NO: 6 (L1-SP1), SEQ ID NO: 14 (L2-SP1), SEQ ID NO: 8 (L3-SP1), SEQ ID NO: 15 (L6-SP1), SEQ ID NO: 3 (mtbSP-SP1), SEQ ID NO: 9 (L4-SP1), SEQ ID NO: 86 (SP1-CBD) or any combination thereof. In one embodiment, the protein extracts are pure, i.e., undergo a further step of purification after obtaining the heat stable fraction of the crude extract expressed by the bacteria. In another embodiment, the protein extracts are crude extracts, i.e., the heat stable fraction of the crude extract, used as obtained from the bacteria that expressed them.

In some embodiments, the SP1 based polypeptide interact with the target substance, or with the chemical environment via a reversible interaction such as Van Der Waals (VDW), hydrogen bonds, or electrostatic interactions, or via non-reversible covalent bonds, all are referred to herein as molecular associations. As used herein the phrase "molecular association" refers to a chemical association or a physical association or both, which takes place on a molecular level. For example, a bond or association can be a covalent bond, a VDW interaction, hydrogen bonds, electrostatic interactions, hydrophobic interactions, etc.

Types of reversible molecular associations or bonds suitable for use in the present invention are associations selected from the group consisting of electrostatic bonding, hydrogen bonding, van der Waals forces, ionic interaction or donor/acceptor bonding. The reversible association can be mediated by one or more associations between the substance (i.e., CNP, e.g., CB or CNT) and the SP1 based polypeptide. For example, the reversible association can include a combination of hydrogen bonding and ionic bonding between the complexing substance and the SP1 polypeptide. Additionally, or alternatively, the reversible association can be in combination with, for example, covalent or other noncovalent interactions between components, such as between a substance and an SP1 based polypeptide or chimeric polypeptide. In one embodiment, the SP1 based polypeptide or the chimeric SP1 based polypeptide interact with the CNP via hydrophobic interactions. In another embodiment, via hydrogen bonds. In another embodiment, via VDW interactions; or in another embodiment, via electrostatic interactions. In another embodiment, the SP1 based polypeptide or the chimeric SP1 based polypeptide interact with the CNP via combination of hydrophobic interactions, hydrogen bonds, VDW interactions, and electrostatic interactions. Such interactions between the SP1 based polypeptide or the chimeric SP1 polypeptide and the CNP are also regarded herein as "complexation", whereas the bound SP1-CNP material is regarded herein as an SP1/CNP "complex".

The SP1 based polypeptides, chimeric SP1 polypeptides and compositions of matter comprising the same have been shown to enhance dispersal of bound substances in a solvent. For example, highly insoluble carbon nanotubes were found to disperse with up to 1000-fold greater concentration in both aqueous and organic environments when complexed with a chimeric, carbon nanotube-binding L1 SP1 (see U.S. Pat. No. 8,957,189 herein incorporated by reference in its entirely).

As used herein, the term "dispersion" refers to the ability of a solute or a colloid to be evenly distributed and/or dissolved in a solvent, in order to form a solution or suspension comprising the solvent and solute. It will be appreciated that all solutes are, in theory, soluble in all solvents. However, poorly or negligibly soluble (immiscible) solutes or colloids do not form solutions or suspensions of any significant concentration with given solvents.

Thus, as used herein, "enhancing the dispersion" refers to increasing the concentration of said substance, as a solute or colloid, in a solution or suspension with a solvent. In a preferred embodiment, the substance is a hydrophobic substance, typically insoluble or poorly soluble in water, and the solvent is an aqueous solvent.

Stability under centrifugation under standard conditions is used as a measure for dispersion ability.

The stability of SP1 based polypeptides and chimeric SP1 based polypeptides bound to CNT (SP1/CNT complexes) to boiling, protease digestion and pH extremes is shown in U.S. Pat. No. 8,957,189.

Following is a list of the ID sequences associated with SP1.

| | |
|---|---|
| SEQ ID NO. 1 | CTGCTCGATCTCATTCCAAGCTGTA AGAGTTTCAATTGGGGCACG |
| SEQ ID NO. 2 | GCAAGTCTGGTTTGCAAGA GTACTGCGATTCTGCTGCTCTTGCTG |
| SEQ ID NO. 3 | MRKLPDAATRTPKLVKHTLLTRFKDEITREQIDNYINDYTNLLDLIPSMKSFNW GTDLGMESAELNRGYTHAFESTFESKSGLQEYLDSAALAAFAEGFLPTLSQRLV IDYFLY |
| SEQ ID NO. 4 | MATRTPKLVKHTLLTRFKDEITREQIDNYINDYTNLLDLIPSMKSFNWGTDLGM ESAELNRGYTHAFESTFESKSGLQEYLDSAALAAFAEGFLPTLSQRLVIDYFLY |
| SEQ ID NO. 5 | RKLPDAA |

| | |
|---|---|
| SEQ ID NO. 6 | MHWSAWWIRSNQSATRTPKLVKHTLLTRFKDEITREQIDNYINDYTNLLDLIPS<br>MKSFNWGTDLGMESAELNRGYTHAFESIFESKSGLQEYLDSAALAAFAEGFLPT<br>LSQRLVIDYFLY |
| SEQ ID NO. 7 | CCACAGAGAG AAAGGGAAGA CATGAAGCTT GTGAAGCACA CATTGTTGAC<br>TCGGTTCAAG GATGAGATCA CACGAGAACA GATCGACAAC TACATTAATG<br>ACTATACCAA TCTGCTCGAT CTCATTCCAA GCATGAAGAG TTTCAATTGG<br>GGCACGGATC TGGGCATGGA GTCTGCGGAG CTAAACCGAG GATACACTCA<br>TGCCTTTGAA TCTACATTTG AGAGCAAGTC TGGTTTGCAA GAGTACCTCG<br>ATTCTGCTGC TCTTGCTGCA TTTGCAGAAG GGTTTTTGCC TACTTTGTCA<br>CAGCGTCTTG TGATAGACTA CTTTCTCTAC TAA |
| SEQ ID NO. 8 | MDYFSSPYYEQLFATRTPKLVKHTLLTRFKDEITREQIDNYINDYTNLLDLIPS<br>MKSFNWGTDLGMESAELNRGYTHAFESTFESKSGLQEYLDSAALAAFAEGFLPT<br>LSQRLVIDYFL |
| SEQ ID NO. 9 | MHWSAWWIRSNQSATRTPKLVKHTLLTRFKDEITKEQIDNYINDYTNLLDLIPS<br>MKSFNWGTDLGMESAELNRGYTHAFESTFESKSGLQEYLDSAALAAFAEGFLPT<br>LSQRLVIDYFLY |
| SEQ ID NO. 10 | HWSAWWIRSNQS |
| SEQ ID NO. 11 | HSSYWYAFNNKT |
| SEQ ID NO. 12 | DYFSSPYYEQLF |
| SEQ ID NO. 13 | SNQS |
| SEQ ID NO. 14 | MHSSYWYAFNNKTATRTPKLVKHTLLTRFKDEITREQIDNYINDYTNLLDLIPS<br>MKSFNWGTDLGMESAELNRGYTHAFESTFESKSGLQEYLDSAALAAFAEGFLPT<br>LSQRLVIDYFLY |
| SEQ ID NO. 15 | MSNQSATRTPKLVKHTLLTRFKDEITREQIDNYINDYTNLLDLIPSMKSFNWGT<br>DLGMESAELNRGYTHAFESIFESKSGLQEYLDSAALAAFAEGFLPTLSQRLVID<br>YFLY |
| SEQ ID NO. 16 | MHWSAWWIRSNQSATRTPKLVKHTLLTRFKDEITREQIDNYINDYTNLLDLIPS<br>MKSFNWGTDLGMESAELNRGYTHAFESIFESKSGLQEYLDSAALAAFAEGFLPT<br>LSQRLVIDYFLY |
| SEQ ID NO. 17 | MHWSAWWIRSNQSATRTPKLVKHTLLTRFKDEICREQIDNYINDYTNLLDLIPS<br>MKSFNWGTDLGMESAELNRGYTHAFESIFESKSGLQEYLDSAALAAFAEGFLPT<br>LSQRLVIDYFLY |
| SEQ ID NO. 18 | MHWSAWWIRSNQSATRTPKLVKHTLLTRFKDEITKEQIDNYINDYTNLLDLIPS<br>MKSFNWGTDLGMESAELNRGYTHAFESTFESKSGLQEYLDSAALAAFAEGFLPT<br>LSQRLVIDYFLY |
| SEQ ID NO. 19 | RALPDA |
| SEQ ID NO. 20 | AKPSYPPTYK |
| SEQ ID NO. 21 | AKPTYK |
| SEQ ID NO. 22 | PKISYPPTYK |
| SEQ ID NO. 23 | APPPAXTAXK |
| SEQ ID NO. 24 | ATPKPXTAXK |
| SEQ ID NO. 25 | PYVK |
| SEQ ID NO. 26 | AKPSPYVPTGYK |
| SEQ ID NO. 27 | GQQKQTAYDPGYK |
| SEQ ID NO. 28 | ATCCACAGAG AGAAAGGGAA GACATGGCAA CCAGAACTCC AAAGCTTGTG<br>AAGCACACAT TGTTGACTCG GTTCAAGGAT GAGATCACAC GAGAACAGAT<br>CGACAACTAC ATTAATGACT ATACCAATCT GCTCGATCTC ATTCCAAGCA<br>TGAAGAGTTT CAATTGGGGC ACGGATCTGG GCATGGAGTC TGCGGAGCTA<br>AACCGAGGAT ACACTCATGC CTTTGAATCT ACATTTGAGA GCAAGTCTGG<br>TTTGCAAGAG TACCTCGATT CTGCTGCTCT TGCTGCATTT GCAGAAGGGT<br>TTTTGCCTAC TTTGTCACAG CGTCTTGTGA TAGACTACTT TCTCTACTAA<br>ACGCTCAGGA GTAACGACTT CGGCCGGGCT ATTTCATGGT AATAAAGTAA<br>TGTAATGTTC AATAAATGCT GGTTTTGAAC CACTGAATGT TCGTGTCTTG<br>ATTTCTTGTC TGTGCTAAGT GAAGGGAGTG CTGCTATTCC TTTAAAAATA<br>AAGCCCTTGG GGTTGAGTTG TAGTTTTTCA ATCTTTTTCC CCGATTTATT<br>TCGGTCTTGG TGTTGTT |

-continued

| | |
|---|---|
| SEQ ID NO. 29* | VVKHLVIVQFKEDVTPERLDGLIRGYAGLVDKVPSMKAFHWGTDVSIE Xaa Xaa NMHQGFTHVFESTFESTEGVKEYVYHEFATDFLGSTEKVLIIDF |
| SEQ ID NO. 30* | VVKHLVIVQFKEDVTPERLDGLIRGYAGLVDKVPSMKAFHWGTDVSIEN Xaa MHQGFTHVFESTFESTEGVKEYVYHPAHVEFATDFLGSTEKVLIIDF |
| SEQ ID NO. 31* | VVKHLVIVQFKEDVTPERLEGLIRGYAGLVDKVPSMKAFHWGTDVSIEN Xaa MHQGFTHVFESTFESTEGVKEYVYHPAHVEFATDFLGSTEKVLIIDF |
| SEQ ID NO. 32* | VVKHILLASEKEEVTQERLDELIRGYAALVGVVPSMKAFHWGTDVSIEN Xaa MHQGFTHVFESTFESTEGIKEYIEHPAHVEFAK |
| SEQ ID NO. 33* | VVKHILLARFKEDVAPERLDQLIRGYAGLVDLVPSMKAFHWGTDVSIEN Xaa MHQGFTHVFESTFESTEGVKEYIEHPAHVEFANEFLPVLEKTLIIDY |
| SEQ ID NO. 34* | VVKHLVLARFKEEATPEALD Xaa LIRRYAGLVDAVPSfMKAFHWGTDVTV Xaa Xaa LDTHEGFTHVFESTFESAEGVKEYIAHPSHVEFVDEFLALAEKML IVDY |
| SEQ ID NO. 35 | MEEAKGPVKHVLLASEKDGVSPEKIEELIKGYANLVNLIEPMKAFHWGKDVSIE NLHQGYTHIFESTFESKEAVAEYIAHPAHVEFATIFLGSLDKVLVIDYKPTSVS L |
| SEQ ID NO. 36 | LHQGYTHILESIFESKEAVAEYIAHPAHVEFATIFLGSLDKVLVIDY |
| SEQ ID NO. 37* | VVKHVLLAKFKDDVTPERIEELIKDYANLVNLIPPMKSFHWGKDVSAEN Xaa LHQGFTHVFESIFESPEGVAEYVAHPAHVEYANLELSCLEKVIVIDY |
| SEQ ID NO. 38* | VVKHILLAKEKDGIPPEQIDQLIKQYANLVNLVEPMKAFQWGKDVSIEN Xaa LHQGFTHVFESTFDSLEGVAEYIAHPVHVEYANTLLPQLEKFLIVDY |
| SEQ ID NO. 39* | HVLLPKLKDYFTPERIELMVDYANLVNLMPRMKSFHSGRDVSAEYLHL Xaa Xaa GCTHVYESTFDSPGVAEYVAHAAHVEYANQDLSCLEKVIAIDY |
| SEQ ID NO. 40 | MATRTPKLVKHTLATREKDEITREQIDNYINDYTNLLDLIPSMKSENWGTDLGM ESAELNRGYTHAFESTFESKSGLQEYLDSAALAAFAEGFLPTLSQRLVIDYFLY |
| SEQ ID NO. 41* | KHLCLVRFKEGVVVEDI Xaa Xaa Xaa IEELTKLAAE Xaa LDTVKFFGW GKDVLNQEALTQGFTHVFSMSFASAEDLAAYMGHEKHSAFAATFMAVLDKVVVL DF |
| SEQ ID NO. 42* | KHLCLVRFKEGVVVEDI Xaa Xaa Xaa IEELTKLAAELDTVKFFGWGKDVL NQEA Xaa LTQGFTHVESMSFASAEDLAACMGHEKHSAFAATFMAVLDKVVVL DF |
| SEQ ID NO. 43* | KHLCMAKFKEGVVVEDI Xaa Xaa Xaa IQELTKLAAELDTVKYFGWGKDVL NQEA Xaa LTQGETHVEVMTFASAEDLAACMGHEKHTAFAATFMAALDKVVVM DF |
| SEQ ID NO. 44* | VKHLCLVKFKEEVL Xaa Xaa Xaa VDDILQGMTKLVS EMDMVKSFEWGKD V Xaa LNQEMLTQGFTHVFSLTFASSEDLTTYMSHERHQEFAGTFMAAIDKVV VVDF |
| SEQ ID NO. 45* | RRPTMGEVKHLCLVKFKEGVVVEDVLKGMTDLVAGMDMV Xaa Xaa Xaa KS FEWGQDV Xaa LNQEMLTQGFTHVFSLTFAFADDLATYMGHDRHAAFAATFMA ALDKVVVIDF |
| SEQ ID NO. 46* | ESTFESTEGIKEYIEHPAHVEFAK Xaa LNQEMLTQGFTHVFSLTFATAADLA AYMAHDSHTAFAATFMAAIDKVLVVDF |
| SEQ ID NO. 47* | KHLVLVKFKEDVVVEDILKELEKLVQEMDIV Xaa Xaa Xaa KSFVWGKDV Xaa Xaa ESHEMLRQGFTHAIIMTENSKEDYQTFANHPNHVGFSATFATVIDK AVLLDF |
| SEQ ID NO. 48* | LLVKFKQDVVEEDVLKQIEQLVNEIDLI Xaa Xaa Xaa KSFVWGKDT Xaa Xaa ESNEMVTQGYTHAMIMTENSKEDYEACVVKEV Xaa Xaa EFSAIFVTV VEKILVLNF |
| SEQ ID NO. 49* | HYVIVKFKDGVA Xaa Xaa Xaa VDDLIQGLEKMVEGIDHVKSFEWGKDI Xaa Xaa ESHDMLRQGFTHAFLMTFNGKEEFNAFQTHPNHLEFSGVFSPAIEK IVVLDF |
| SEQ ID NO. 50* | HYVIVKFKDGVA Xaa Xaa Xaa VDELIQGLEKMVSGIDHVKSFEWGKDI Xaa Xaa ESHDMLRQGFTHVFLMAFNGKEEFNAFQTHPNHLEFTGVFSPAIEK IVVLDF |

| | |
|---|---|
| SEQ ID NO. 51* | KHEVIVKFKEGVA Xaa Xaa Xaa VDELTKGMEKLVTEIGAVKSFEWGQDI Xaa Xaa ESLDVLRQGFTHAFLMTFNKKEDFVAFQSHPNHVEFSTKFSAAIEN IVLLDF |
| SEQ ID NO. 52* | LVSEIHAVKSFEWGQDI Xaa Xaa ESLDVLRQGFTHAFLMTFNKKRRL |
| SEQ ID NO. 53 | MATSGEKHLVVVKFKEDTKVDEILKGLENLVSQIDTVKSFEWGEDKESHDMLRQ GFTHAFSMIPENKDGYVAFTSHPLHVEFSAAFTAVIDKIVLLDFPVAAVKSSVV ATP |
| SEQ ID NO. 54* | KTVEHIVLFKVKEETEPSKVSDMVNGLGSLVSLDPVLH Xaa LSVGPLLRNRS SALT Xaa Xaa FTHMLHSRYKSKEDLEAYSAHPSHVSVVKGYVLPIIDDIMS VDW |
| SEQ ID NO. 55 | AAAACATATG CGCAAACTTC GGATGCGGC AACCAGAACT CCAAAGCTTG TGAAGCACAC ATTGTTGACT CGGTTCAAGG ATGAGATCAC ACGAGAACAG ATCGACAACT ACATTAATGA CTATACCAAT CTGCTCGATC TCATTCCAAG CATGAAGAGT TTCAATTGGG GCACGGATCT GGGCATGGAG TCTGCGGAGC TAAACCGAGG ATACACTCAT GCCTTTGAAT CTACATTTGA GAGCAAGTCT GGTTTGCAAG AGTACCTCGA TTCTGCTGCT CTTGCTGCAT TTGCAGAAGG GTTTTTGCCT ACTTTGTCAC AGCGTCTTGT GATAGACTAC TTTCTCTACT AA |
| SEQ ID NO. 56 | AAGGAGATAT ACAAAAACAT ATGCACTGGT CAGCATGGTG GATACGATCA AATCAATCAG CAACCAGAAC TCCAAAGCTT GTGAAGCACA CATTGTTGAC TCGGTTCAAG GATGAGATCA CACGAGAACA GATCGACAAC TACATTAATG ACTATACCAA TCTGCTCGAT CTCATTCCAA GCATGAAGAG TTTCAATTGG GGCACGGATC TGGGCATGGA GTCTGCGGAG CTAAACCGAG GATACACTCA TGCCTTTGAA TCTACATTTG AGAGCAAGTC TGGTTTGCAA GAGTACCTCG ATTCTGCTGC TCTTGCTGCA TTTGCAGAAG GGTTTTTGCC TACTTTGTCA CAGCGTCTTG TGATAGACTA CTTTCTCTAC TAA |
| SEQ ID NO. 57 | GAAGGAGATA TACAAAAACA TATGCACTCA TCATACTGGT ACGCATTCAA CAACAAAACA GCAACCAGAA CTCCAAAGCT TGTGAAGCAC ACATTGTTGA CTCGGTTCAA GGATGAGATC ACACGAGAAC AGATCGACAA CTACATTAAT GACTATACCA ATCTGCTCGA TCTCATTCCA AGCATGAAGA GTTTCAATTG GGGCACGGAT CTGGGCATGG AGTCTGCGGA GCTAAACCGA GGATACACTC ATGCCTTTGA ATCTACATTT GAGAGCAAGT CTGGTTTGCA AGAGTACCTC GATTCTGCTG CTCTTGCTGC ATTTGCAGAA GGGTTTTTGC CTACTTTGTC ACAGCGTCTT GTGATAGACT ACTTTCTCTA CTAA |
| SEQ ID NO. 58 | ATACAAAAAC ATATGGATTA TTTTTCATCA CCATATTATG AACAATTATT TGCAACCAGA ACTCCAAAGC TTGTGAAGCA CACATTGTTG ACTCGGTTCA AGGATGAGAT CACACGAGAA CAGATCGACA ACTACATTAA TGACTATACC AATCTGCTCG ATCTCATTCC AAGCATGAAG AGTTTCAATT GGGGCACGGA TCTGGGCATG GAGTCTGCGG AGCTAAACCG AGGATACACT CATGCCTTTG AATCTACATT TGAGAGCAAG TCTGGTTTGC AAGAGTACCT CGATTCTGCT TACTTTCTCT ACTAA |
| SEQ ID NO. 59 | AGAAGGAGAT ATACAAAAAC ATATGTCAAA TCAATCAGCA ACCAGAACTC CAAAGCTTGT GAAGCACACA TTGTTGACTC GGTTCAAGGA TGAGATCACA CGAGAACAGA TCGACAACTA CATTAATGAC TATACCAATC TGCTCGATCT CATTCCAAGC ATGAAGAGTT TCAATTGGGG CACGGATCTG GGCATGGAGT CTGCGGAGCT AAACCGAGGA TACACTCATG CCTTTGAATC TACATTTGAG AGCAAGTCTG GTTTGCAAGA GTACCTCGAT TCTGCTGCTC TTGCTGCATT TGCAGAAGGG TTTTTGCCTA CTTTGTCACA GCGTCTTGTG ATAGACTACT TTCTCTACTA A |
| SEQ ID NO. 60 | AAGGAGATAT ACAAAAACAT ATGCACTGGT CAGCATGGTG GATACGATCA AATCAATCAG CAACCAGAAC TCCAAAGCTT GTGAAGCACA CATTGTTGAC TCGGTTCAAG GATGAGATCA CAAAGAACA GATCGACAAC TACATTAATG ACTATACCAA TCTGCTCGAT CTCATTCCAA GCATGAAGAG TTTCAATTGG GGCACGGATC TGGGCATGGA GTCTGCGGAG CTAAACCGAG GATACACTCA TGCCTTTGAA TCTACATTTG AGAGCAAGTC TGGTTTGCAA GAGTACCTCG ATTCTGCTGC TCTTGCTGCA TTTGCAGAAG GGTTTTTGCC TACTTTGTCA CAGCGTCTTG TGATAGACTA CTTTCTCTAC TAA |
| SEQ ID NO. 61 | AAGGAGATAT ACAAAAACAT ATGCACTGGT CAGCATGGTG GATACGATCA AATCAATCAG CAACCAGAAC TCCAAAGCTT GTGAAGCACA CATTGTTGAC TCGGTTCAAG GATGAGATCT GCCGAGAACA GATCGACAAC TACATTAATG ACTATACCAA TCTGCTCGAT CTCATTCCAA GCATGAAGAG TTTCAATTGG GGCACGGATC TGGGCATGGA GTCTGCGGAG CTAAACCGAG GATACACTCA TGCCTTTGAA TCTACATTTG AGAGCAAGTC TGGTTTGCAA GAGTACCTCG ATTCTGCTGC TCTTGCTGCA TTTGCAGAAG GGTTTTTGCC TACTTTGTCA CAGCGTCTTG TGATAGACTA CTTTCTCTAC TAA |
| SEQ ID NO. 62 | AAGGAGATAT ACAAAAACAT ATGCACTGGT CAGCATGGTG GATTCGTTCA AATCAATCAG CAACCAGAAC TCCAAAGCTT GTGAAGCACA CATTGTTGAC |

|  |  |
|---|---|
| SEQ ID NO. 63 | AAGGAGATAT ACAAAAACAT ATGCACTGGT CAGCATGGTG GATTCGTTCA<br>AATCAATCAG CAACCAGAAC TCCAAAGCTT GTGAAGCACA CATTGTTGAC<br>TCGGTTCAAG GATGAGATCA CAAAAGAACA GATCGACAAC TACATTAATG<br>ACTATACCAA TCTGCTCGAT CTCATTCCAA GCATGAAGAG TTTCAATTGG<br>GGCACGGATC TGGGCATGGA GTCTGCGGAG CTAAACCGAG GATACACTCA<br>TGCCTTTGAA TCTACATTTG AGAGCAAGTC TGGTTTGCAA GAGTACCTCG<br>ATTCTGCTGC TCTTGCTGCA TTTGCAGAAG GTTTTTGCC TACTTTGTCA<br>CAGCGTCTTG TGATAGACTA CTTTCTCTAC TAA |
| SEQ ID NO. 64 | MKLVKHTLLTREKDEITREQIDNYINDYTNLLDLIPSMKSENWGTDLGMESAEL<br>NRGYTHAFESTEESKSGLQEYLDSAALAAFAEGELPTLSQRLVIDYELY |
| SEQ ID NO. 65 | CTGCTCGATCTCATTCCAAGCTGTA AGAGTTTCAATTGGGGCACG |
| SEQ ID NO. 66 | GCAAGTCTGGTTTGCAAGA GTACTGCGATTCTGCTGCTCTTGCTG |
| SEQ ID NO. 67 | AAAACATATGCGCAAACTTCCGGATGCGGCAACCAGAACTCCAAAGCTTG |
| SEQ ID NO. 68 | AAAAGAGCTCTTAGTAAAGAAAGTAATCAATAAC |
| SEQ ID NO. 69 | ATGAAGCTTG TGAAGCACAC ATTGTTGACT CGGTTCAAGG ATGAGATCAC<br>ACGAGAACAG ATCGACAACT ACATTAATGA CTATACCAAT CTGCTCGATC<br>TCATTCCAAG CTGTAAGAGT TTCAATTGGG GCACGGATCT GGGCATGGAG<br>TCTGCGGAGC TAAACCGAGG ATACACTCAT GCCTTTGAAT CTACATTTGA<br>GAGCAAGTCT GGTTTGCAAG AGTACCTCGA TTCTGCTGCT CTTGCTGCAT<br>TTGCAGAAGG GTTTTTGCCT ACTTTGTCAC AGCGTCTTGT GATAGACTAC<br>TTTCTCTACT AA |
| SEQ ID NO. 70 | AAGGAGATATACAAAAACATATGCACTGGTCAGCATGGTGGATACGATCA<br>AATCAATCAGCAACCAGAACTCCAAAG |
| SEQ ID NO. 71 | CTTTGGAGTTCTGGTTGCTGATTGATTTGATCGTATCCACCATGCTGA<br>CCAGTGCATATGTTTTTGTATATCTCCTT |
| SEQ ID NO. 72 | AGAAGGAGATATACAAAAACATATGCACTCATCATACTGGTACGCATTCA<br>ACAACAAAACAGCAACCAGAACTCCAAAGC |
| SEQ ID NO. 73 | GCTTTGGAGTTCTGGTTGCTGTTTTGTTGTTGAATGCGTACCAGTATGATGA<br>GTGCATATGTTTTTGTATATCTCCTTCT |
| SEQ ID NO. 74 | ATACAAAAACATATGGATTATTTTTCATCACCATATTATGAACAATTATTTG<br>CAACCAGAACTCC |
| SEQ ID NO. 75 | GGAGTTCTGGTTGCAAATAATTGTTCATAATATGGTGATGAAAATAATCC<br>ATATGTTTTTGTAT |
| SEQ ID NO. 76 | AGAAGGAGATATACAAAAACATATGTCAAATCAATCAGCAACCAGAACTC<br>CAAAGC |
| SEQ ID NO. 77 | GCTTTGGAGTTCTGGTTGCTGATTGATTTGACATATGTTTTTGTATATCTCCTT<br>CT |
| SEQ ID NO. 78 | ACTGGTCAGCATGGTGGATTCGATCAAATCAATCAG |
| SEQ ID NO. 79 | CTGATTGATTTGATCGAATCCACCATGCTGACCAGT |
| SEQ ID NO. 80 | GTCAGCATGGTGGATTCGTTCAAATCAATCAGCAACC |
| SEQ ID NO. 81 | GGTTGCTGATTGATTTGAACGAATCCACCATGCTGAC |
| SEQ ID NO. 82 | TGACTCGGTTCAAGGATGAGATCACAAAAGAACAGATCGACA |
| SEQ ID NO. 83 | TGTCGATCTGTTCTTTTGTGATCTCATCCTTGAACCGAGTCA |
| SEQ ID NO. 84 | ACTCGGTTCAAGGATGAGATCTGCCGAGAACAGATCGACAACTAC |
| SEQ ID NO. 85 | GTAGTTGTCGATCTGTTCTCGGCAGATCTCATCCTTGAACCGAGT |
| SEQ ID NO. 86 | MAATSSMSVEFYNSNKSAQTNSITPIIKITNTSDSDLNLNDVKVRYYYTSDGTQ<br>GQTFWCDHAGALLGNSYVDNTSKVTANFVKETASPTSTYDTYVEFGFASGRATL<br>KKGQFITIQGRITKSDWSNYTQTNDYSFDASSSTPVVNPKVTGYIGGAKVLGTA<br>PAVPSGSVTSTSKTTTTASKTSTSTSSTSEFMATSTPKLVKHTLLTRFKDEITR |

|  | -continued |
|---|---|
|  | EQIDNYINDYTNLLDLIPSMKSFNWGTDLGMESAELNRGYTHAFESTFESKSGL<br>QEYLDSAALAAFAEGFLPTLSQRLVIDYFLY |
| SEQ ID NO. 87 | MAATSSMSVEFYNSNKSAQTNSITPIIKITNTSDSDLNLNDVKVRYYYTSDGTQ<br>GQTFWCDHAGALLGNSYVDNTSKVTANFVKETASPTSTYDTYVEFGFASGRATL<br>KKGQFITIQGRITKSDWSNYTQTNDYSFDASSSTPVVNPKVTGYIGGAKVLGTA<br>P |
| SEQ ID NO. 88 | MATSTPKLVKHTLLTRFKDETTREQIDNYINDYTNLLDLIPSMKSFNWGTDLGM<br>ESAELNRGYTHAFESTFESKSGLQEYLDSAALAAFAEGFLPTLSQRLVIDYFLY |
| SEQ ID NO. 89 | AVPSGSVTSTSKTTTTASKTSTSTSSTSEF |

In some embodiments, the SP1 polynucleotide sequence is 70%, 75%, 80%, 85%, 90%, 95%, or up to 100% homologous to SEQ ID NO: 28. It will be appreciated that polynucleotides encoding SP1 homologues SEQ ID NOs: 29-54 can be suitable for producing the SP1 polypeptide of the present invention, when fulfilling the abovementioned criteria.

SP1/Carbon Nanoparticle

This invention describes compositions comprising SP1 Based polypeptide, and carbon nanoparticles (CNPs) such as: carbon black (CB) and carbon nanotubes (CNT) (referred herein as "SP1/CNP" composition).

According to this invention, the term "carbon nanoparticle" refers both to carbon nanotubes and to carbon black.

The SP1/CNP compositions are preferably obtained as dispersion in a solvent. The solvent used for the dispersion can be water, common organic solvents or a mixture thereof. Non-limiting exemplary organic solvents include less polar hydrocarbon solvent, such as pentanes, hexanes, petroleum ether, benzene and toluene; and polar solvents, such as ether, tetrahydrofuran, dichloromethane, chloroform, dichloroethane, dimethylsulfoxide, dimethylformamide, dimethylacetamide, dioxane, methanol, ethanol ethyl acetate, acetonitrile, acetone and carbon tetrachloride. Preferably, the solvent is an aqueous solution. More preferably the solvent is water.

As used herein, "films" refer to polymeric sheet. Plastic films have a wide variety of applications including packaging, plastic bags, labels, building construction, landscaping, electrical fabrication, printing substrates photographic film, film stock for movies, video tape, etc. Common plastic films include but are not limited to: Polyethylene film (Low-density polyethylene, Medium-density polyethylene, High-density polyethylene, and Linear low-density polyethylene), Polypropylene film (a cast film, biaxially oriented film (BOPP), or a uniaxially oriented film), Polyester film (Bo-PET is a biaxially oriented polyester film), Nylon film, Polyvinyl chloride film (with or without a plasticizer), and a variety of bioplastics and biodegradable plastic films.

According to some embodiments of the present invention the SP1 based polypeptides, and chimeric SP1-carbon surfaces (i.e. CNT or graphitic surfaces) polypeptides can bind to carbon nanoparticles, forming composition which can further bind to polymer fibers such as carbon fibers, polyesther, kevlar, nylon, cotton, wool and the like, and can be used to modify the properties of such fibers. For example, the SP1/CB, SP1/CNT/can bind to polymer fibers to facilitate to provide added strength, or can be used to promote binding of carbon nanoparticles to synthetic or natural fabrics, fabric precursors and films, such as polyester, aramid (Kevlar™), nylon or cotton, in a uniform manner, to provide fibers and fabrics that have unique chemical, electrical, and thermal properties. Such fabrics and surfaces may comprise layers comprising carbon nanoparticle surfaces associated with certain polymeric substances and resins.

According to some embodiments of the present invention, there are provided compositions of matter comprising an SP1 based polypeptide of the present invention and carbon nanoparticle (e.g., CNT, CB), having a target binding peptide component, and the target substance. Such a composition of matter can include, in some embodiments, for example, L1SP1 chimera (SEQ ID NO: 6) bound to carbon nanotube, L1SP1 (SEQ ID NO: 6) bound to carbon fibers, L3SP1 (SEQ ID NO: 8) bound to carbon black, L3SP1 (SEQ ID NO: 8) bound to carbon nanotube, and the like. In another embodiment, the composition of matter according to this invention may comprise a non-chimeric SP1 based polypeptide, i.e., without a target binding peptide component. e.g., SP1 wild-type, while still comprising a target substance such as carbon nanoparticle (e.g., CNT, CB).

As used herein, the phrase "SP1 based polypeptide-CNP complex" or "SP1/CNP" refers to a composition of matter comprising an SP1 or chimeric SP1 based polypeptide, bound to at least one carbon nanoparticle. In one embodiment, the carbon nanoparticle is carbon black. In another embodiment the carbon nanoparticle is carbon nanotube. In another embodiment, the composition is in the form of dispersion. In a preferred embodiment, the dispersion is an aqueous dispersion.

In one embodiment, this invention is directed to a polymer, fiber, film, fabric or polymeric fabric coated with, or complexed to a composition of matter comprising SP1 based polypeptide, CNP as described herein above. In another embodiment, the polymer, fiber, film, fabric or polymeric fabric comprises at least one of: cotton, wool, silk, nylon, polyester, polypropylene, glass-fiber, elastane, Kevlar and aramid. In another embodiment, the polymer, fiber, film, fabric or polymeric fabric is polyester. In another embodiment, the polymer, fiber, film, fabric or polymeric fabric is Aramid. In another embodiment, the polymer, fiber, film, fabric or polymeric fabric is nylon. In another embodiment, the nylon is a nylon fabric. In another embodiment the nylon is a nylon film.

As used herein, the phrase "SP1 polypeptide-CNP-polymer complex", also regarded as "SP1/CNP coated fiber" or "SP1/CNP enforced fiber" refers to a polymer, fiber, yarn, cord, film or fabric coated with, or complexed to a composition comprising an SP1 based or chimeric SP1 based polypeptide and CNP bound thereto. In one embodiment, the CNP is carbon black. In another embodiment the CNP is carbon nanotube.

In another embodiment, the polymer, fiber, film, fabric or polymeric fabric according to this invention further comprises a polyethyleneimine (PEI). In another embodiment, the polymer, fiber, film, fabric or polymeric fabric according to this invention is coated with at least one layer of polyethyleneimine (PEI). In another embodiment, with one layer; two layers; three layers; or four layers of PEI; each possibility represents a separate embodiment of the invention.

"Polyethylenimine" (PEI) (also called "polyaziridine") is a polymer with repeating unit composed of the amine group and two carbon aliphatic $CH_2CH_2$ spacer. Linear polyethyleneimines contain all secondary amines, in contrast to branched PEIs which contain primary, secondary and tertiary amino groups. PEI is available at various molecular weights. In one embodiment, the PEI that finds utility in the context of this invention has a molecular weight of between 800 Da and 750,000 Da. In another embodiment, the PEI is high molecular weight PEI. In another embodiment the PEI is low molecular weight PEI. In another embodiment, the molecular weight of the PEI is between 1 KDa and 10,000 KDa; In another embodiment, between 10 KDA and 100 KDa; In another embodiment, between 25 KDa and 80 KDa; In another embodiment, between 50 KDa and 70 KDa. In another embodiment, the molecular weight of the PEI is about 60 KDa.

In another embodiment, the loading of the PEI applied to the fiber, film or fabric is between about 0.05% and about 5% (weight PEI/weight fabric). In another embodiment, between about 0.5% and about 2.5%. In another embodiment, between about 0.5% and about 1.5%. In another embodiment, between about 1.8% and about 2.0%. In another embodiment, between about 0.1% and about 1.0%.

In one embodiment, the fiber, yarn, cord, film, or fabric coated with the composition of matter according to this invention comprises a woven or non-woven fiber, yarn, cord, film, or fabric. In another embodiment said woven and non-woven fiber, yarn, cord, film, or fabric is selected from natural fiber, yarn, cord, film, or fabric, synthetic fiber, yarn, cord, film, or fabric, a mixture of natural and synthetic fiber, yarn, cord, film, or fabric, and inorganic material based fiber, yarn, cord, film, or fabric. Exemplary natural fabrics include, but are not limited to cotton, wool and silk. Exemplary synthetic fabric fiber or film include, but are not limited to nylon, polyester, aramid, rayon, polypropylene, polyethylene naphthanate (PEN), polyolefin ketone (POK), and elastane (Lycra™-Spandex™). Examples of garments, rope, sewn, molded and woven items fashioned from fabric and yarns coated with the SP1/CNT according to the present invention include, but are not limited to: parachutes, clothing, sleeping bags, bicycle parts and equipment, skis, etc (for further detailed examples, see U.S. Pat. Nos. 7,354,877, and 8,957,189, which are incorporated herein by reference).

In one embodiment, the polymer, fiber, film, fabric or polymeric fabric of this invention comprises a plurality of layers of the composition of matter of this invention bound to said polymer, fiber, film, fabric or polymeric fabric. In another embodiment, it comprises one layer of said composition of matter bound to said polymer, fiber, film, fabric or polymeric fabric. In another embodiment, it comprises two layers of said composition of matter bound to said polymer, fiber, film, fabric or polymeric fabric. In another embodiment, it comprises three layers of said composition of matter bound to said polymer, fiber, film, fabric or polymeric fabric.

In one embodiment, this invention is directed to a polymer, fiber, film, fabric or polymeric fabric coated with at least one layer of a composition of matter comprising SP1 based polypeptide according to this invention, Carbon nanoparticle (i.e., SP1/CB, SP1/CB). In one embodiment the fiber, film or fabric is coated with at least one layer of SP1/CB. In another embodiment, the fiber, film or fabric is coated with at least one layer of SP1/CB/metal. In another embodiment, the fiber, film or fabric is coated with at least one layer of SP1/CNT/metal.

In one embodiment, this invention is directed to a polymer, fiber, film, fabric or polymeric fabric complexed with a composition of matter comprising SP1 based polypeptide according to this invention, Carbon nanoparticle (i.e., SP1/CB). In one embodiment the fiber, film or fabric is complexed with SP1/CB.

In another embodiment the carbon nanoparticle (CNP) is carbon nanotube.

Further embodiments of the invention include, but are not limited to, tires having at least one SP1 based polypeptide-CNT-complexed polymer, fiber, film, fabric or polymeric fabric element forming a conductive path for discharging static electric charge buildup (for details of construction of such tires, see, for example, US Patent Application 2010078103, to Nakamura, U.S. Pat. No. 7,528,186 to Halas a, U.S. Pat. No. 7,284,583 to Dheur et al and U.S. Pat. No. 7,131,474 to Sandstrom), tires having at least one SP1 based polypeptide-CNT-complexed polymer, fabric or polymeric fabric element having improve thermal conductivity and heat transfer to the road during use (for details of construction and use of such tires, see, for example, U.S. Pat. No. 7,337,815 to Spadone), tires having at least one SP1 based polypeptide-CNT-complexed polymer, fabric or polymeric fabric element capable of communicating information on tire status and performance, such as tire pressure, deformation, tread and sidewall wear and failure, rolling resistance, etc. at rest and in motion, during use (for details of construction and use of such tires, see, for example, U.S. Pat. No. 7,318,464 to Hahn et al and U.S. Pat. No. 7,581,439 to Rensel, et al.) and electrical energy generating tires with a conductive strip of a SP1 based polypeptide-CNT-complexed polymer, fabric or polymeric fabric, and an energy generating component (such as a piezo-ceramic or thermal-harvesting material) incorporated into the tread and/or sidewall of the tire ((for details of construction and use of such tires, see, for example, U.S. patent application Ser. No. 00/70,028,958 to Retti and U.S. patent application Ser. No. 00/90,314,404 to Rodgers et al).

SP1 based polypeptides complexed with target substances can be added to polymers, fibers, films, or fabrics in a variety of methods. In some embodiments, the complex of SP1 based polypeptide and target substance (for example, L3-SP1-CB complex) is prepared similarly to the method described in U.S. Pat. No. 8,957,189 for SP1-CNT complexes. Alternatively, the complex of SP1 based polypeptide and target substance (e.g. carbon nanotube, carbon black) is prepared by as described herein below.

This invention also relate to methods of producing fibers, yarns, cords, films, fabrics or polymeric fabrics enforced with carbon nanoparticles (CNP). In one embodiment, the method for producing such fibers, yarns, cords, films, fabrics or polymeric fabrics comprise contacting a dispersion comprising composition of matter comprising SP1 based polypeptide according to this invention and CNP (SP1/CNP), with a polymer, fiber, film, fabric or polymeric fabric. Preferably, the method comprises a pre-step of de-sizing of said fibers, yarns, cords, films, fabrics or polymeric fabrics prior to contacting it with the composition. In one embodiment, the method further comprises a step of washing the unbound composition from said polymer, fiber, film, fabric or polymeric fabric with buffer or water. In another embodiment, the method further comprises a step of contacting the polymer, fiber, film, fabric or polymeric fabric, with polyethyleneimine (PEI) prior to contacting the polymer, fiber, film, fabric or polymeric fabric with said composition, and after the de-sizing pre-step. Preferably, the steps of contacting the fiber with PEI, contacting the dispersion with the fiber, and washing the unbound composition, are repeated at least once; in another embodiment, they are repeated twice; three, four times, or even up to ten times. In one embodiment, the method further comprises a post-treatment step of contacting the fiber, yarn, cord, film, fabric or polymeric fabric with PEI as the last step. In one embodiment, the CNP is implemented as CB. In another embodiment, the CNP is implemented as CNT. In another embodiment, said step of contacting the dispersion comprising the composition of this invention with the polymer, fiber, film, or fabric, is performed using a textile dying machine. Non limiting examples of textile dying machines are: Jigger coating machine for woven fabrics or vertical or horizontal yarn or fabric package dyeing system.

In one embodiment, a method of producing a fiber, yarn, cord, film, fabric or polymeric fabric coated with carbon nanoparticles includes:

a. Optionally de-sizing a fiber, yarn, cord, film, fabric or polymeric fabric;
b. Optionally contacting said fiber, yarn, cord, film, fabric or polymeric fabric with polyethyleneimine (PEI);
c. Contacting a dispersion comprising a composition of SP1 Based polypeptide and CNP according to this invention with the fiber, yarn, cord, film, fabric or polymeric fabric; and
d. Optionally repeating steps (b) and (c) at least once;
e. Optionally contacting said fiber, yarn, cord, film, fabric or polymeric fabric, with polyethyleneimine (PEI).

In another embodiment, the method further comprises a step of washing the fiber, yarn, cord, film, fabric or polymeric fabric with a buffer or water after each step.

In another embodiment, said step of contacting the dispersion comprising the composition of this invention with the polymer, fiber, film, or fabric, is performed using a textile dying machine.

SP1/Carbon Black (CB)

The present invention provides, in some embodiments thereof, the ability to weave carbon black into fibers, films and fabrics that may be applied to a wide range of uses.

Unexpectedly, it was found by the inventors that SP1 based polypeptides are capable of enhancing the dispersion of not only CNT; but also, CB in aqueous solutions. Such SP1/CB dispersions can be utilized for the reinforcement of polymer fibers, fabrics and films.

CB binding to fibers via the SP1 protein provides additional surface for receiving metallic conductors, improves interaction with the fibers, and induces cross linking between the fibers. In addition protein binding to the fiber by itself may improve the interaction with the polymer through reactive groups on the protein surface. It is demonstrated that SP1 variants according to this invention, are capable of binding CB to structural fibers.

Successful incorporation of CB into the fabric allows the fabrics to adopt some of the mechanical, thermal, electrical, physical and chemical properties associated with carbon black. The SP1/CB compositions of matter according to this invention can be utilized to incorporate the CB into the fabrics.

"Carbon black" (CB) is a form of para-crystalline carbon that has a high surface-area-to-volume ratio, albeit lower than that of activated carbon. It is dissimilar to soot in its much higher surface-area-to-volume ratio and significantly lower (negligible and non-bioavailable) PAH (polycyclic aromatic hydrocarbon) content. It is produced by the incomplete combustion of heavy petroleum products such as FCC tar, coal tar, ethylene cracking tar, and a small amount from vegetable oil. It is used often in the Aerospace industry in elastomers for aircraft vibration control components such as engine mounts. In the context of this invention, any type of CB can be used. The various CB types and brands are differing in their surface area, aggregate size distribution and morphological structure. Non limiting examples of CB types include: conductive CB, CB-N326, CB-N220, CB-N660, CRX™ 1346, CRX™ 1490, PROPEL™ D11, PROPEL™ E3, PROPEL™ E6, PROPEL™ E7, REGAL® 300, VULCAN® 10, VULCAN® 10H, VULCAN® 10HD, VULCAN® 1345, VULCAN® 1380, VULCAN® 1391, VULCAN® 1436, VULCAN® 3, VULCAN® 3H, VULCAN® 6, VULCAN® 6-LP, VULCAN® 7H, VULCAN® 8, VULCAN® 9, VULCAN® 9H, VULCAN® J, VULCAN® M. In general CB particles ranging from 10 nm to 10 micron may be used.

Accordingly provided herein is a composition of matter comprising carbon black (CB) bound to an SP1 based polypeptide according to this invention (referred herein as "SP1/CB" composition). In another embodiment, the carbon black is non-covalently bound to the SP1 based polypeptide. In another embodiment, the SP1 based polypeptide is a wild type SP1 protein. In another embodiment, the SP1 based polypeptide is a chimeric SP1 based polypeptide as described herein above. In another embodiment, the SP1 based polypeptide comprises a carbon nanotube or graphitic surfaces binding peptide. In another embodiment, the chimeric SP1 polypeptide has the amino acid sequence as set forth in SEQ ID NO: 8.

Accordingly, in another embodiment, provided herein is a composition of matter comprising carbon black (CB), SP1 based polypeptide according to this invention. In one embodiment, the CB is non-covalently bound to the SP1 based polypeptide.

The SP1/CB compositions of matter according to this invention are preferably obtained as dispersions in solvent. The solvent used for the dispersion can be water, common organic solvents or a mixture thereof. Non-limiting exemplary organic solvents include less polar hydrocarbon solvent, such as pentanes, hexanes, petroleum ether, benzene and toluene; and polar solvents, such as ether, tetrahydrofuran, dichloromethane, chloroform, dichloroethane, dimethylsulfoxide, dimethylformamide, dimethylacetamide, dioxane, methanol, ethanol, ethyl acetate, acetonitrile, acetone and carbon tetrachloride. Preferably, the solvent is an aqueous solution. More preferably the solvent is water.

In one embodiment, the SP1/CB is in the form of aqueous dispersions in a concentration of between 0.01% and 50% w/w. In another embodiment, the composition is in the form of an aqueous dispersion in a concentration of between 0.5% and 30%. In another embodiment, the composition is in the form of an aqueous dispersion in a concentration of between 1% and 20%. In another embodiment, the composition is in the form of an aqueous dispersion in a concentration of between 4% and 17%. In another embodiment, the composition is in the form of an aqueous dispersion in a concentration of 1% w/w, 2% w/w, 3% w/w, 4% w/w, 6% w/w, 8% w/w, 10% w/w, 12% w/w, 14% w/w, 16% w/w, 17% w/w, 18% w/w, 20% w/w, 22% w/w, 24% w/w, 25% w/w, 28% w/w, 30% w/w; each value represents a separate embodiment of the invention. Preferably, the dispersion concentration is up to 17% w/w; more preferably, the dispersion concentration is 17% w/w.

For use in fiber coating methods, the SP1/CB dispersion is normally diluted to a concentration of between 0.01% and 0.5% w/w. Preferably, the concentration is between 0.05% and 0.15% w/w. More preferably the concentration is 0.05%, 0.1% or between 0.05% and 0.1% w/w; each value represents a separate embodiment of the invention.

The SP1/CB dispersions can be formed in various CB:SP1 ratios as stable dispersion. In one embodiment, the CB:SP1 ratio in the dispersion ratio is between 0.1:1 to 15:1 dry weight/weight. Preferably the CB:SP1 ratio is between 0.3:1 to 10:1 dry w/w. More preferably, the CB:SP1 ratio is between 3:1 to 8:1 dry w/w. In one embodiment, the CB:SP1 ratio is 5.5 dry w/w. In another embodiment, the CB:SP1 ration is 3.0 dry w/w, 3.5 dry w/w, 4.0 dry w/w, 4.5 dry w/w, 5.0 dry w/w, 5.5 dry w/w, 6.0 dry w/w, 6.5 dry w/w, 7.0 dry w/w, 7.5 dry w/w, 8.0 dry w/w, 9.0 dry w/w, or 10.0 dry w/w; each value represents a separate embodiment of the invention. In one embodiment the SP1 is an isolated SP1. In another embodiment, the SP1 is the crude SP1, i.e. the heat stable fraction of an extract of bacteria expressing the SP1 protein.

In one embodiment, this invention is directed to a polymer, fiber, film, fabric or polymeric fabric coated with at least one layer of a composition of matter comprising SP1 based polypeptide, CB (SP1/CB) and as described herein above. In another embodiment, the polymer, fiber, film, fabric or polymeric fabric comprises at least one of: cotton, wool, silk, nylon, polyester, polypropylene, glassfiber, elastane, Kevlar and aramid. In another embodiment, the polymer, fiber, film, fabric or polymeric fabric is polyester. In another embodiment, the polymer, fiber, film, fabric or polymeric fabric is Aramid. In another embodiment, the polymer, fiber, film, fabric or polymeric fabric is nylon. In another embodiment, the nylon is a nylon fabric. In another embodiment the nylon is a nylon film.

In another embodiment, the polymer, fiber, film, fabric or polymeric fabric according to this invention further comprises at least one layer of polyethyleneimine (PEI). In another embodiment, the polymer, fiber, film, fabric or polymeric fabric according to this invention is coated with at least one layer of polyethyleneimine (PEI). In another embodiment, the PEI is high molecular weight PEI. In another embodiment the PEI is low molecular weight PEI. In one embodiment, the PEI that finds utility in the context of this invention has a molecular weight of between 800 Da and 750,000 Da. In another embodiment, the PEI is high molecular weight PEI. In another embodiment the PEI is low molecular weight PEI. In another embodiment, the molecular weight of the PEI is between 1 KDa and 10,000 KDa; In another embodiment, between 10 KDA and 100 KDa; In another embodiment, between 25 KDa and 80 KDa; In another embodiment, between 50 KDa and 70 KDa. In another embodiment, the molecular weight of the PEI is about 60 KDa. In another embodiment, the applied loading of the PEI on the fiber, film or fabric is between about 0.05% and about 5%. In another embodiment, between about 0.5% and about 2.5%. In another embodiment, between about 0.5% and about 1.5%. In another embodiment, between about 1.8% and about 2.0%. In another embodiment, between about 0.05% and about 0.3%. In another embodiment, the applied loading of the PEI on the fiber, film or fabric is 0.05%, 0.07%, 0.09%, 0.1%, 0.12%, 0.14%, 0.16%, 0.18%, 0.2%, 0.21%, 0.25%, 0.28%, or 0.3%; each value represents a separate embodiment of the invention.

In another embodiment, the loading of said composition on said polymer, fiber, film, fabric or polymeric fabric is between 5 gr/kg and 15 gr/kg. In another embodiment, the loading is between 7 gr/kg and 14 gr/kg. In another embodiment, the loading is about 7 gr/kg. In another embodiment, the loading is about 10 gr/kg. In another embodiment, the loading is about 10.5 gr/kg. In another embodiment, the loading is about 14 gr/kg. In another embodiment, the loading is about 3.5 gr/kg. In another embodiment, the loading is about 1 gr/Kg, 2 gr/Kg, 3 gr/Kg, 3.5 gr/Kg, 4 gr/Kg, 5 gr/Kg, 5.5 gr/Kg, 6 gr/Kg, 7 gr/Kg, 8 gr/Kg, 9 gr/Kg, 10 gr/Kg, 11 gr/Kg, 12 gr/Kg, 14 gr/Kg, 16 gr/Kg, 18 gr/Kg, 20 gr/Kg, 30 gr/Kg, 40 gr/Kg, 50 gr/Kg, 60 gr/Kg, 70 gr/Kg, 80 gr/Kg, 90 gr/Kg, 100 gr/Kg; each value represents a separate embodiment of the invention. Preferably, the loading is 7 gr/Kg. The loading can be achieved by one layer coating or by multi-layer coating; in one embodiment, the loading is achieved by one layer coating; in another embodiment, the loading is achieved by two layer coating; in another embodiment, the loading is achieved by three layer coating; preferably the coating is achieved by two layer coating; e.g. two loadings of 3.5 g/Kg.

In one embodiment, this invention is directed to a polymer, fiber, film, fabric or polymeric fabric coated with a composition of matter comprising SP1 based polypeptide and CB according to this invention (i.e., SP1/CB composition).

In one specific embodiment, SP1 based polypeptides and chimeric SP1 polypeptides, are used to bind carbon black, and the resulting SP1 polypeptide-CB-complex (i.e., SP1/CB composition) is then used to bind the CB to a polymer fiber, film or fabric, such as aramid (e.g. Kevlar™), for incorporation into rubber tires, in order to enhance the mechanical and/or physical properties (e.g. electrical, mechanical and/or thermal) and function of the tires.

As used herein, the phrase "SP1 based polypeptide-CB complex" or "SP1/CB composition" refers to a composition comprising an SP1 or chimeric SP1 polypeptide, bound to carbon black.

As used herein, the phrase "SP1 polypeptide-CB-polymer complex" or SP1/CB-enforced fiber" refers to a polymer, fiber, yarn, cord, film or fabric coated with an SP1/CB composition according to this invention.

This invention also relate to methods of producing fibers, yarns, cords, films, fabrics or polymeric fabrics coated with carbon nanoparticles (e.g., carbon black or carbon nanotubes). In one embodiment, the method for producing such fibers, yarns, cords, films, fabrics or polymeric fabrics comprise contacting a dispersion comprising composition of matter comprising SP1 based polypeptide according to this invention, CB (SP1/CB) with a polymer, fiber, film, fabric or polymeric fabric. Preferably, the method comprises a prestep of de-sizing of said fibers, yarns, cords, films, fabrics or polymeric fabrics prior to contacting it with the composition. In one embodiment, the method further comprises a step of washing the unbound composition from said polymer, fiber, film, fabric or polymeric fabric. In another embodiment, the method further comprises a step of contacting the polymer, fiber, film, fabric or polymeric fabric, with polyethyleneimine (PEI) prior to contacting the polymer, fiber, film, fabric or polymeric fabric with said composition, and after the de-sizing pre-step. Preferably, the steps of contacting the dispersion with the fiber, washing the unbound composition and contacting with PEI are repeated at least once. In one embodiment, the method further comprises a post-treatment step of contacting the fiber, yarn, cord, film, fabric or polymeric fabric with PEI as the last step. In another embodiment, said step of contacting the dispersion comprising the composition of this invention with the polymer, fiber, film, or fabric, is performed using a textile dying machine. Non limiting examples of textile dying machines are: Jigger coating machine for woven fabrics or vertical or horizontal yarn or fabric package dyeing system.

In one embodiment, this invention is directed to a method of producing a fiber, yarn, cord, film, fabric or polymeric fabric coated with carbon black, said method comprises:
a. Optionally de-sizing a fiber, yarn, cord, film, fabric or polymeric fabric;
b. Optionally contacting said fiber, yarn, cord, film, fabric or polymeric fabric with polyethyleneimine (PEI);
c. Contacting a dispersion comprising a composition of SP1 Based polypeptide, CB with the fiber, yarn, cord, film, fabric or polymeric fabric;
d. Optionally repeating steps (b) and (c) at least once;
e. Optionally contacting said fiber, yarn, cord, film, fabric or polymeric fabric, with polyethyleneimine (PEI).

In another embodiment, said step of contacting the dispersion comprising the composition of this invention with the polymer, fiber, film, or fabric, is performed using a textile dying machine.

Methods of preparing composite materials using SP1/CB complexes include, but are not limited to contacting an SP1/CB dispersion in a solvent with polymer, fiber, film, or fabric under conditions sufficient to form an SP1/CB-polymer composite, wherein the SP1/CB complex is deposited on the polymer, fiber, film or fabric. In one embodiment, the polymer, fiber, film or fabric is dipped into the SP1/CB dispersion to form a SP1/CB coated composite material. The solvent used for the SP1/CB dispersion can be water, common organic solvents or a mixture thereof.

In one specific embodiment, SP1 based polypeptides and chimeric SP1 polypeptides, are used to hind carbon nanotubes, and the resulting SP1 polypeptide-CNT-complex is then used to bind the CNT to a polymer fiber, film or fabric, such as aramid (e.g. Kevlar™).

As used herein, the phrase "SP1 based polypeptide-CNT complex" or "SP1/CNT" refers to a composition comprising an SP1 or chimeric SP1 polypeptide, bound to at least one carbon nanotube, for example, as described in detail in Examples 1-3. This invention also relate to methods of producing fibers, yarns, cords, films, fabrics or polymeric fabrics coated with carbon nanotubes. In one embodiment, the method for producing such fibers, yarns, cords, films, fabrics or polymeric fabrics comprise contacting a dispersion comprising composition of matter comprising SP1 based polypeptide according to this invention, CNT with a polymer, fiber, film, fabric or polymeric fabric. Preferably, the method comprises a pre-step of de-sizing of said fibers, yarns, cords, films, fabrics or polymeric fabrics prior to contacting it with the composition. In one embodiment, the method further comprises a step of washing the unbound composition from said polymer, fiber, film, fabric or polymeric fabric with buffer or water. In another embodiment, the method further comprises a step of contacting the polymer, fiber, film, fabric or polymeric fabric, with polyethyleneimine (PEI) prior to contacting the polymer, fiber, film, fabric or polymeric fabric with said composition, and after the de-sizing prestep. Preferably, the steps of contacting the dispersion with the fiber, washing the unbound composition and contacting with PEI are repeated at least once. In one embodiment, the method further comprises a post-treatment step of contacting the fiber, yarn, cord, film, fabric or polymeric fabric with PEI as the last step. In another embodiment, said step of contacting the dispersion comprising the composition of this invention with the polymer, fiber, film, or fabric, is performed using a textile dying machine. Non limiting examples of textile dying machines are: Jigger coating machine for woven fabrics or vertical or horizontal yarn or fabric package dyeing system.

In one embodiment, a method of producing a fiber, yarn, cord, film, fabric or polymeric fabric coated with carbon nanotubes, includes:

a. Optionally de-sizing a fiber, yarn, cord, film, fabric or polymeric fabric;
b. Optionally contacting said fiber, yarn, cord, film, fabric or polymeric fabric with polyethyleneimine (PEI);
c. Contacting a dispersion comprising a composition of SP based polypeptide, CNT according to this invention with the fiber, yarn, cord, film, fabric or polymeric fabric;
d. Optionally repeating steps (b) and (c) at least once; and
e. Optionally contacting said fiber, yarn, cord, film, fabric or polymeric fabric, with polyethyleneimine (PEI).

In a certain embodiment, washing is performed at each step with a buffer, water, or other appropriate scouring agent.

Contacting the dispersion with the polymer, fiber, film, or fabric, is performed either in a textile dying machine for batch processing or in a bath for continuous processing depending on the embodiment.

Various techniques are suitable for the formation of nanocomposite materials. These include injection molding, extrusion, blow molding, thermoforming, rotational molding, cast and encapsulation and calendaring.

Definitions

As used herein, a plurality of filaments or fibers grouped together either through twisting or entanglement forms a yarn strand also referred to as yarn. A plurality of yarn wound together forms thread and a plurality of threads wound together forms cord. Yarn, thread, or cord combined into a sheet either through weaving or otherwise forms fabric.

A "fiber" refers to a strand having a diameter between 1-1000 micron.

"Tex" unit refers to mass in grams of fiber/1,000 meters and a decitex (dtex) refers to grams of fiber/10,000 meters.

"High twist" refers to more than 120 twists of yarn or thread/meter and low twist refers to at less than 80 twists of yarn or thread/meter. Medium twist refers to 80-120 twists/meter. Twist levels applies to fibers, yarn, and thread.

"Interlocked fibers" refers to state in which a plurality of fibers are held together either through entanglement or twisting with each other, according to an embodiment.

"Coating" is defined by the type material forming the coating; a coating that is formed from material different from the adjacent material is deemed as a separate coating. For example, three coatings in which a material differing from the outer coatings would constitutes three coatings even if the outer layers are the same material since coating each is different from the adjacent material. It should be appreciated that each coating is formed by one or more contiguous layers.

"Room Temperature" refers to a temperature anywhere between 20°-60° C. In a certain embodiment certain steps or all steps can be performed at a temperature as low as 4° C. and as high as 90° C.

It should be appreciated that the number twists is defined by the outmost unit and not the subunits forming the unit for the purposes of this application. For example, high twist thread refers to the number of winds of thread and not the number of winds of yarn forming the thread. Similarly, low twist yarn refers to the number of winds of yarn and not the number of winds of the fibers forming the yarn.

As used herein the term "about" refers to ±10%.

Throughout this application, various embodiments of this invention may be presented in a range format. It should be understood that the description in range format is merely for convenience and brevity and should not be construed as a limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above description, illustrate some embodiments of the invention in a non-limiting fashion.

General Experimental Concept of Complexing SP1 and CNP

The studies presented below demonstrate two strategies for altering the binding properties of SP1 variants, namely the affinity and avidity of SP1 variants to various substrates and controlling the immobilization of SP1 on various surfaces. Affinity and avidity are two terms used in protein biochemistry to describe strength of non-covalent interactions, the phenomenon whereby certain atoms or molecules have the tendency to aggregate or bond.

The term "affinity" is used to describe the strength of a single bond, while the term "avidity" is use to describe the combined strength of multiple bond interactions affinity. Dissociation constant (Kd), or equilibrium constant, is the inverse of the affinity constant, measures the propensity of a larger object to separate (dissociate) reversibly into smaller components, as when a complex falls apart into its component molecules, or when a salt dissociates into its component ions. The dissociation constant is usually denoted Kd and is the inverse of the affinity constant. In the special case of salts, the dissociation constant can also be called the ionization constant.

The first strategy involves positioning of the anchoring side-chains, such as found in cysteine residues, on the dodecameric protein's ring rim, and comparing the binding properties of the resulting construct with those of a protein construct having anchoring side-chains positioned at the inner side of the annulus (the pore or "hole" of the ring). This strategy uncovers the capacity of the SP1 basic architecture to protect certain regions on its surface, and ligands attached thereat, from surface exposure.

In the second strategy, several binding moieties are attached to the SP1 dodecameric protein at the protein's annulus inner pore by genetic engineering. By fusing these specific affinity peptides at a putative protected part of the protein, the binding moieties are expected to be less available for binding with large entities which are excluded from the protein's pore. This experimental strategy is designed to study the effect of changing the conditions of the media of the protein, and to show that entering a factor to the media, which can affect the structure of the SP1 monomers and thus the structure of the entire dodecamer, can control the degree of exposure of the binding moieties to the media. The event of adding the structure altering factor, such as a denaturating agent, can thus increase the ability of the binding moieties to interact and bind large entities in the media. The capacity to switch from a non-binding entity to a binding entity by adding and removing a chemical factor constitutes a chemical switch.

The concept of a chemical switch was demonstrated by fusing several specific affinity peptides, such as silicon binding peptides, to each of the SP1 basic skeleton, at inner pore position, to thereby obtain a silicon binding protein switch, which is sensitive to the media levels of denaturating agents, such as guanidinium hydrochloride (GuHCl). The affinity peptide was isolated by Sano and coworkers [Sano, K. I. et al. JACS. 125, pp 14234-14235, 2003; Sano, K. I et al., JACS, 128, pp 1717-1722, 2006; and Sano, K. I. et al., Nano Lett., 7, pp 3200-3202, 2007] using a peptide-phage display system. This six amino acids peptide, referred to herein and in the art as mTBP, was reported by Sano and coworkers to bind to Ti, Ag and Si surfaces, but not to Au, Cr, Pt, Sn, Zn, Cu, or Fe.

Thus, a SP1 scaffold was modified to present 12 copies of the mTBP hexapeptide in a switchable manner. A positive cooperative effect is demonstrated when the peptide is presented on the SP1 dodecamer, as compared to the free peptide, accompanied with significant reduction in non-specific binding of the fused peptides compared to that of the free peptide.

Example 1

Construction of SP1 Variants with High Affinity to Various Materials

WO 2007/007325 provides a non-limiting list of peptides forming complexes with inorganic ionic substances, adapted from Sarikaya et al. [Ann. Rev. Mater. Res., 2004, 34, 373-408]. These relatively short peptides are suitable for fusion to the SP1 protein as part of the modification of the SP1 polypeptide. Many more examples of peptides with high affinity to different materials are disclosed in the literature.

Table 1 presents the SP1 variants used in this context, their binding ability, primers used for their construction, mutation or insertion at the N-terminus, SP1 template, reference, and growth conditions/induction. All mutant proteins demonstrated characteristics similar to the wild type SP1 in terms of heat stability, protease resistance and complex formation. Standard nomenclature of mutations is used i.e., amino acids position using wild type sequence including first methionine residue.

TABLE 1

| SP1 variant/ Relevant activity | PCT Primers | Mutation and/or Insertion at the N-terminus | SP1 Template and reference | Growth conditions/ induction |
|---|---|---|---|---|
| Wild type SP1 (SEQ ID NO: 4) | | | U.S. patent application No. 2006/0172298 | Terrrfic broth or Luria broth/ 37° C./ IPTG 1 mM |
| Δ2-6 (SEQ ID NO: 64) | | Δ2-6 | Wang et al. (2006); WO 2007/007325 | Luria broth/ 37° C./ IPTG 1 mM |
| M43C Δ2-6 (SEQ ID NO: 1) | 5' CTGCTCGAT CTCATTCCAAGC TGTAAGAGTTTC AATTGGGGCAC G 3' | M43C Δ2-6 | Δ2-6 | Luria broth/ 37° C./ IPTG 1 mM |
| L81C Δ2-6 Flat gold binding (SEQ ID NO: 2) | 5' GCAAGTCTG GTTTGCAAGAGT ACTGCGATTCTG CTGCTCTTGCT G 3'. | L81C Δ2-6 | Δ2-6 | Luria broth/ 37° C./ IPTG 1 mM |
| mtbSP Switchable silicon oxide binding CNT dispersion (SEQ ID NO: 3) | 5'-AAAACATAT GCGCAAACTTCC GGATGCGGCAAC CAGAACTCCAAA GCTTG-3' and SP1rev 5'-AAAAGAGCT CTTAGTAAAGAA AGTAATCAATAA C-3') | RKLPDAA (SEQ ID NO: 5) | M43C Δ2-6 Medalsy et al. (2008); WO 2007/007325 | Terrific broth or Luria broth/ 37° C./ IPTG 1 mM |
| L1-SP1 CNT dispersion (SEQ ID NO: 6) | 5'AAGGAGATAT ACAAAAACATAT GCACTGGTCAGC ATGGTGGATACG ATCAAATCAATC AGCAACCAGAAC TCCAAAG 3' 5'CTTTGGAGTT CTGGTTGCTGAT TGATTTGATCGT ATCCACCATGCT GACCAGTGCATA TGTTTTTGTATA TCTCCTT 3' | HWSAWWIRSNQS (SEQ ID NO: 10) | Wild type | Terrific broth/ 28° C./ IPTG 1 mM |

TABLE 1-continued

| SP1 variant/ Relevant activity | PCT Primers | Mutation and/or Insertion at the N-terminus | SP1 Template and reference | Growth conditions/ induction |
|---|---|---|---|---|
| L2-SP1 CNT dispersion (SEQ ID NO: 14) | 5'AGAAGGAGAT ATACAAAAACAT ATGCACTCATCA TACTGGTACGCA TTCAACAACAAA ACAGCAACCAGA ACTCCAAAGC 3' 5'GCTTTGGAGT TCTGGTTGCTGT TTTGTTGTTGAA TGCGTACCAGTA TGATGAGTGCAT ATGTTTTTGTAT ATCTCCTTCT 3' | HSSYWYAFNNKT (SEQ ID NO: 11) | Wild type | Terrific broth/ 37° C./, IPTG 0.1 mM |
| L3-SP1 CNT dispersion Kevlar binding (SEQ ID NO: 8) | 5'ATACAAAAAC ATATGGATTATT TTTCATCACCAT ATTATGAACAAT TATTTGCAACCA GAACTCC 3' 5'GGAGTTCTGG TTGCAAATAATT GTTCATAATATG GTGATGAAAAT AATCCATATGTT TTTGTAT 3 | DYFSSPYYEQLF (SEQ ID NO: 12) | Wild type | Terrific broth/ 37° C./ IPTG 0.5 mM |
| L6-SP1 CNT dispersion (SEQ ID NO: 16) | 5'AGAAGGAGAT ATACAAAAACAT ATGTCAAATCAA TCAGCAACCAGA ACTCCAAAGC 3' 5'GCTTTGGAGT TCTGGTTGCTGA TTGATTTGACAT ATGTTTTTGTAT ATCTCCTTCT 3 | SNQS (SEQ ID NO: 13) | Wild type | IPTG 1 mM/ 37° C./ Terrific broth |

Example 2

Carbon Nanotubes (CNT) Dispersion by SP1 Variants

The Examples presented below provide SP1 variants, fused to CNT-binding peptides, which are capable of binding to CNT and thereby enable the aqueous dispersion of these protein-coated CNT. Several examples of short peptides that were isolated from phage display libraries as CNT-binding peptides are disclosed in the literature. See, for example, Nature materials, 2003, 2, 196; Nano lett., 2006, 6, 40-44; and Langmuir, 2004, 20, 8939-8941).

Table 2 below presents the terminus sequence of these variants, as well as their purification method and grade, N-terminal sensitivity to digestion by alcalase, and the SP1 variant concentration which is required for CNT dispersion. All mutant proteins demonstrated characteristics similar to the wild type SP1 in terms of heat stability, protease resistance and complex formation. Shift in molecular weight relatively to samples that were not treated with alcalase was observed both in samples that were not boiled or boiled in SDS gel application buffer (complex and monomer, respectively). In all cases the apparent molecular weight of the alcalase treated SP1 variants was higher than those of wild type, indicating that some but not all the added amino-acids were removed, and they are different from published sequences.

TABLE 2

| SP1 variant | Peptide fused to the N-terminus | Grade | SDS PAGE analysis: Complex Formed | SDS PAGE analysis: N-terminal sensitivity to digestion by alcalase | SP1 concentration required for CNT dispersion (mg/ml) | References |
|---|---|---|---|---|---|---|
| Wild type | None | 80° C. plus alcalase treatment | Yes | No | 1 | |
| | | Ion exchange purified protein | Yes | | <1 | |

TABLE 2-continued

| | | | | SDS PAGE analysis | | |
| | | | | N-terminal sensitivity to digestion by alcalase | SP1 concentration required for CNT dispersion (mg/ml) | |
| SP1 variant | Peptide fused to the N-terminus | Grade | Complex Formed | | | References |
| --- | --- | --- | --- | --- | --- | --- |
| mtbSP | RKLPDAA (SEQ ID NO: 5) | 80° C. treatment Ion exchange purified protein | Yes Yes | No | 0.2 0.1 | U.S. Application No. 20070112174 U.S. Application No. 20070117148 *Nano Lett.*, 2007, 6, 1579-1579. |
| L1-SP1 | HWSAWWIRSNQS (SEQ ID NO: 10) | 80° C. plus alcalase treatment Ion exchange purified Ion exchange purified plus alcalase treatment | Yes Yes Yes | Yes | 0.004 0.004 0.004 | U.S. Pat. No. 7,304,128 U.S. Application No. 20070117147 U.S. Application No. 20070117150 U.S. Application No. 20070117148 U.S. Application No. 20040058457 *Nature Materials*, 2003, 2, 196 |
| L2-SP1 | HSSYWYAFNNKT (SEQ ID NO: 11) | 80° C. plus alcalase treatment Dissolved inclusion bodies Refolding of IBs | Yes No Yes | Yes Complete digestion Yes | 0.04 0.100 0.1 | U.S. Application No. 20060172282 *Nano Lett.*, 2006, 6, 40-44 |
| L3-SP1 | DYFSSPYYEQLF (SEQ ID NO: 12) | Refolding of IBs 80° C. plus alcalase treatment 80° C. plus alcalase treatment | Yes Yes | Small shift Small shift | 0.1 0.01 | U.S. Application No. 20050277160 *Langmuir*, 2004, 20, 8939-8941 |
| L6-SP1 | SNQS (SEQ ID NO: 13) | 80° C. plus alcalase treatment | Yes | No | 0.05 | |

Surprisingly, treatment with alcalase and partial digestion of the N-terminus doesn't reduce its ability to disperse CNT. This is probably because in each complex not all N-termini are digested and the L1 variant (SEQ ID NO: 6) complex appears as a double band. For example, N-terminus sequencing and MALDY-TOF analysis of alcalase treated L1-SP1 revealed that 8 amino acids were digested by the protease and the N-terminus was SNQS but the digestion doesn't reduce its ability to disperse CNT. In agreement with this conclusion insertion of the SNQS peptide to SP1 N-terminus yields a variant, L6 (SEQ ID NO: 15), with lower CNT dispersion activity, lower than L1 (SEQ ID NO: 6) (50-100 μg/ml versus 4 μg ml, respectively).

Example 3

Tri-Complexes of SP1 Variants, CNT and Aramid (KEVLAR™) or Epoxy Resin

The capacity of the SP1 variants of the present embodiments to bind to advanced materials, such as KEVLAR™, was studied and demonstrated, as presented in detail in U.S. Pat. No. 8,957,189 herein incorporated by reference in its entirely.

SP1 variants were studied for their capacity as multi-functional reagents which can bind CNT through the N-terminus to form a SP1/CNT complex, which in turn can bind to epoxy resin through exposed primary amines. Such reagents can be highly useful in many practical applications involving water interfaces with CNT, including dispersion in epoxy resin. While water and other mediating solvents can be removed by combination of ultra-filtration and freeze drying, these processes are energy consuming and hard to control. The process presented herein takes advantage of the fact that SP1 precipitates in the presence of 70-80% ethanol after 2 hours incubation at −20° C., and so does the CNT protein complex. The precipitated SP1/CNT complex can be easily dispersed in water. The freeze-dried precipitated SP1/CNT complex can be dispersed in epoxy resin as demonstrated in U.S. Pat. No. 8,957,189 herein incorporated by reference in its entirely.

In addition, it was hypothesized that if CNT and aramid (e.g. KEVLAR™—a brand name of a strong and heat-resistant aramid fiber developed by DuPont and used in bullet-proof vests, tires, fiber-optic cables and more) bind to SP1 variants in a similar fashion, the protein may serve as an adhesive mediator to promote attachment of these two components to each other, based on the two-sided doughnut shape of SP1 which exhibits binding sites on both sides of the annulus.

Materials and Methods

Bacterial Strain and Culture Conditions

*Escherichia coli* strain DH5α was used for cloning and *E. coli* strain BL21 (DE3) was used for expression. Cells were grown in either Luria Bertani medium (ΔNSP1, M43CΔNSP1 and L81CΔNSP1), Terrific broth (L1-SP1, L2-SP1, L3-SP1, L6-SP1), or either Luria or Terrific broth interchangeably (native SP1, mtbSP), at 37° C. (except for L1-SP1, which was grown at 28° C.). After induction with isopropyl P-D-thiogalactopyranoside (IPTG)(1 mM for native SP1, mtbSP1, ΔNSP1, M43CΔNSP1, L81CΔNSP1, L1-SP1 and L-6 SP1, 0.5 mM for L3-SP1 and 0.1 mM for L2-SP1) bacteria were grown for additional 4 hours, followed by harvesting by centrifugation at 14,000×g for 15 minutes.

Vector Construction

Both M43C ΔNSP1 mutant and L81C ΔNSP1 mutant were constructed using site directed mutagenesis on the ΔNSP1 coding sequence (SEQ ID NO: 7) template (previously described by Medalsy et al. [Nano lett., 8, 473-477, 2008]), performed in accordance to the Stratagene Quickchange (Stratagene, La Jolla, Calif.) protocol with the PfuTurbo or Deep-vent DNA polymerase.

Primers used for site directed mutagenesis were: C43 (5' CTGCTCGATCTCATTCCAAGCTGTA AGAGTTTCAATTGGGGCACG 3') (SEQ ID NO: 65) for M43C, and C81 (5' GCAAGTCTGGTTTGCAAGA GTACTGCGATTCTGCTGCTCTTGCTG 3') (SEQ ID NO: 66) for L81C.

The mtbSP1 mutant (SEQ ID NO: 3) was constructed using 2 primers: mTB forward primer (5'AAAACATATGCGCAAACTTCCGGATGCGGCAACCAGAACTCCAAAGCTG-3') (SEQ ID NO: 67) and SP1 reverse primer (5'-AAAAGAGCTCTTAGTAAAGAAAGTAATCAATAAC-3') (SEQ ID NO: 68) with M43C ΔNSP1 coding sequence (SEQ ID NO: 69) as a template.

The L1-SP1CNT mutant (SEQ ID NO: 6) was constructed using the primers: forward primer (5'AAGGAGATATACAAAAACATATGCACTGGTCAGCATGGTGGATACGATCA AATCAATCAGCAACCAGAACTCCAAAG 3') (SEQ ID NO: 70) and reverse primer (5'CTTTGGAGTTCTGGTGCTGATTGATTTGATCGTATCCACCATGCTGA CCAGTGCATATGTTTTTGTATATCTCCTT 3') (SEQ ID NO: 71) with native SP1 coding sequence (SEQ ID NO: 28) as a template.

The L2-SP1CNT mutant (SEQ ID NO: 14) was constructed using the primers: forward primer (5'AGAAGGAGATATACAAAAACATATGCACTCATCATACTGCGTACGCATTCA ACAACAAAACAGCAACCAGAACTCCAAAGC 3') (SEQ ID NO: 72) and reverse primer (5'GCTTTGGAGTTCTGGTTGCTGTTTTGTTGTTGAATGCGTACCAGTATGATGA GTGCATATGTTTTTGTATATCTCCTTCT 3') (SEQ ID NO: 73) with native SP1 coding sequence (SEQ ID NO: 28) as a template.

The L3-SP1CNT mutant (SEQ ID NO: 12) was constructed using the primers: forward primer (5'ATACAAAAACATATGGATTATTTTTCATCACCATATTATGAACAATTATTTG CAACCAGAACTCC 3') (SEQ ID NO: 74) and reverse primer (5'GGAGTTCTGGTTGCAAATAATTGTTCATAATATGGTGATGAAAAATAATCC ATATGTTTTTGTAT) 3 (SEQ ID NO: 75) with native SP1 coding sequence (SEQ ID NO: 28) as a template.

The L6-SP1CNT mutant (SEQ ID NO:15) was constructed using the primers: forward primer (5'AGAAGGAGATATACAAAAACATATGTCAAATCAATCAGCAACCAGAACTC CAAAGC 3') (SEQ ID NO: 76) and reverse primer (5' GCTTTGGAGTTCTGGTTGCTGATTGATTTGACATATGTTTTTGTATATCTCCTT CT 3) (SEQ ID NO: 77) with native SP1 coding sequence (SEQ ID NO: 28) as a template.

The L7-SP1CNT mutant (SEQ ID NO: 16) is identical to L1-SP1CNT sequence, except for mutation of the nucleotide sequence encoding the inserted peptide at 5Ile from ata to att, and at 6Arg from cga to cgt, to improve codon usage. The mutant polypeptide was constructed using the primers: for A24T mutant, forward primer (5'-ACTGGTCAGCATGGTGGATTCGATCAAATCAATCAG-3') (SEQ ID NO: 78) and reverse primer (5'-CTGATTGATTTGATCGAATCCACCATGCTGACCAGT-3') (SEQ ID NO: 79). For A27T mutant, forward primer (5'-GTCAGCATGGTGGATTCGTTCAAATCAATCAGCAACC-3') (SEQ ID NO: 80) and reverse primer (5'-GGTTGCTGATTGATTTGAACGAATCCACCATGCTGAC-3') (SEQ ID NO: 81), using "QuikChange Site-Directed Mutagenesis Kit" of "Stratagene" (La Jolla, Calif.).

The L4-SP1CNT mutant (SEQ ID NO: 9) is identical to L1-SP1 CNT sequence, except for mutation of R23K of the inserted peptide. The mutant polypeptide was constructed using the primers: for R23K mutant, forward primer (5'-TGACTCGGTTCAAGGATGAGATCACAAAAGAACAGATCGACA-3') (SEQ ID NO: 82), and reverse primer (5'-TGTCGATCTGTTCTTTTGTGATCTCATCCTTGAACCGAGTCA-3') (SEQ ID NO: 83) using "QuikChange Site-Directed Mutagenesis Kit" of "Stratagene" (La Jolla, Calif.).

The L5-SP1CNT mutant (SEQ ID NO: 17) is identical to L1-SP1CNT sequence, except for mutation of T22C of the inserted peptide. The mutant polypeptide was constructed using the primers: for T22C mutant, forward primer (5'-ACTCGGTCAAGGATGAGATCTGCCGAGAACAGATCGACAACTAC-3') (SEQ ID NO: 84), and reverse primer (5'-GTAGTTGTCGATCTGTTCTCGGCAGATCTCATCCTTGAACCGAGT-3') (SEQ ID NO: 85) using "QuikChange Site-Directed Mutagenesis Kit" of "Stratagene" (La Jolla, Calif.).

The L8-SP1CNT mutant (SEQ ID NO: 18) is identical to L4-SP1CNT sequence, except for mutation of the nucleotide sequence encoding the inserted peptide at 5Ile from ata to att, and at 6Arg from cga to cgt, to improve codon usage. The mutant polypeptide was constructed using the primers: for A24T mutant, forward primer (5'-ACTGGTCAGCATGGTGGATTCGATCAAATCAATCAG-3') (SEQ ID NO: 78) and reverse primer (5'-CTGATTGATTTGATCGAATCCACCATGCTGACCAGT-3') (SEQ ID NO: 79). For A27T mutant, forward primer (5'-GTCAGCATGGTGGATTCGTTCAAATCAATCAGCAACC-3') (SEQ ID NO:80) and reverse primer (5'-GGTTGCTGATTGATTTGAACGAATCCACCATGCTGAC-3') (SEQ ID NO:81), using "QuikChange Site-Directed Mutagenesis Kit" of "Stratagene" (La Jolla, Calif.).

Wild type SP1 was used as a template for PCR reaction (5'-ACTGGTCAGCATGGTGGATTCGATCAAATCAATCAG-3') (SEQ ID NO: 78) and reverse primer (5'-CTGATTGATTTGATCGAATCCACCATGCTGACCAGT-3') (SEQ ID NO: 79) with native SP1 coding sequence (SEQ ID NO: 28) as a template.

All constructs were inserted into pET 29a expression plasmid (Novagen Inc. Madison Wis., USA).

Protein Purification and Refolding

After centrifugation, cell pellets were resuspended in lysis buffer (50 mM Tris HCL 1 mM EDTA, 10 mM MgCl2, pH 8) and sonicated on ice for several minutes with pulsed bursts. Variants were expressed as soluble proteins [mtbSP (SEQ ID NO: 3), L1-SP1 (SEQ ID NO: 6), L6-SP1 (SEQ ID NO: 15)], or aggregated into inclusion bodies [L2 SP1 (SEQ ID NO: 14) and L3-SP1 (SEQ ID NO: 8)].

The insoluble pellets were separated by centrifugation at 14000×g for 15 minutes. Soluble mutated proteins (M43C ΔNSP1 and mtbSP1; L1-SP1; L2-SP1; L3-SP1; L6-SP1) were then heat treated at 85° C. for 30 minutes and treated by protease (alcalase, Novozyme 10<6>-fold dilution: 30 min 40° C.)

Inclusion bodies of L81C ΔNSP1 (SEQ ID NO: 2) mutant were washed first for 15 minutes with the IB washing buffer (20 mM Tris HCL, 2 M urea, pH 8) and thereafter centrifuged at 14000×g for 15 minutes. The pellets were resuspended in denaturation buffer (20 mM Tris HCl, 6 M urea, 10 mM dithiothreitol, pH 8) and diluted to protein concentration of 5 mg/ml. Denaturated proteins were then refolded by dialysis against a folding buffer (20 mM Tris HCl, 1 mM DTT, pH 7) for 4 days.

Ion Exchange FPLC

Hitrap Q Sepharose XL column (1 ml) (Amersham Biosciences, Piscataway, N.J. USA), was used to purify the proteins. Samples were loaded on the column using 20 mM piperazine pH 6.3 buffer at a flow rate of 3 ml/min Elution was conducted with a gradient of 1 M NaCl in the same buffer and determined at 27-33% salt. (mTBP Appendage Peptide: mTBP peptide (SEQ ID NO: 5) was synthetically manufactured by BioSight ltd. (Karmiel, Israel).

Stability Characterization of Mutated Proteins

Three different stability analyses were performed on the wild-type SP1 (SEQ ID NO: 4) and each of the mutated proteins.
1. Heat treatment (H.T) at 80° C. for 30 minutes;
2. Boiling treatment (B.T.) at 100° C. for 30 minutes; and
3. Resistance to proteolysis by proteinase K (PK) at a concentration of 50 ug/ml of the enzyme for one hour at 37° C. PK was eliminated by B.T. for 5 minutes.

Alternatively, alcalase was used to determine stability: Alcalase (Novozyme, 1:1000 dilution) was added at 40° C. for 30 mM Reaction was stopped by inhibition of alcalase at 80° C. for 30 min.

All treatment were followed by centrifugation at 14,000×g for 15 minutes, and analyzed by SDS-PAGE.

Silica Binding mtbSP1 (SEQ ID NO: 3) was mixed with 10 mg silica gel (product no: 28,860-8, Sigma-Aldrich, USA) in 10 mM MES pH 6.5, 150 mM NaCl, with or without 3M GuHCl. The solution was then incubated for one hour on a rotary shaker at room temperature. Thereafter the silica was washed three times with the same buffer without GuHCl. Bound protein was analyzed either by SDS-PAGE or by measuring protein concentration using the Micro BCA assay kit (Pierce, Rockford, USA).

Surface Preparation and Binding

SP1/CNT Binding

SP1/CNT binding to aramid was evaluated using three methods:
1. Determination of the difference between CNT content in solution (suspension) before and after its binding to the fabric. CNT content of a suspension is determined by precipitating the SP1/CNT from a sample of the suspension using guanidinium hydrochloride (100 mM) or HCl (0.3%), before and after its incubation with the fabric (combined with the washing solution), drying the pelleted CNT, and weighing;
2. Spectroscopy: CNT content can be evaluated using spectroscopic method, namely, light transmittance by visualization of a fabric or surface coated by CNT at high resolution under a scanning electron microscope (HR-SEM); and
3. Surface resistivity-CNT content of a coated fabric or surface can be assessed by measuring surface resistivity to current flow (this method is relevant only in cases in which the untreated fabric is a insulator or very poor conductor).

Example 4

Carbon Nanotubes (CNT) Dispersion by SP1 Variants

Materials and Methods:

Multi wall carbon nanotubes (MWCNT) were obtained either from Arkema Inc., France (GRAPHISTRENGTH™ C100) or from Bayer MaterialScience AG, Germany (Baytubes C150 P). Single wall carbon nanotubes (SWCNT) were obtained from Teijin, Ltd (Yamaguchi, Japan).

For small scale production, between 1.0 and 1.3 mg of MWNTs were weighed in 1 ml screw-cap glass tube (Fisherbrand, cat. no. 03-338 AA, size 12×35 mm, ½ DR). A 1 ml protein solution in NaPi buffer (10 mM; pH 8.0) was added to the screw-cap glass tubes containing pre-weighted MWNTs. The resulting mixture was sonicated for 2 hours at 80° C. using an Elma Transsonic Sonifier. The sonicated samples were first centrifuged in an Eppendorf centrifuge tube for 20 minutes at 20000×g. Ninety percent of the upper supernatant was separated using a pipette, avoiding taking the sediment at the bottom, and transferred to another Eppendorf centrifuge tube. The separated supernatant samples were diluted ten-fold. The CNT dispersion by L2-SP1 (SEQ ID NO: 14) was also tested in Tris buffer (10 mM; pH 8.0) with or without urea.

For larger scale production, 400-mg of MWCNT were weighed into a glass flask, a protein solution (400 ml in NaPi buffer; 10 mM; pH 8.0) was added, and the mixture sonicated at a power setting of 260 W for 4 hours, maintaining a maximal temperature of less than 50° C., using a Misonix 4000 Sonicator with a booster home, a 1 inch flat tip and a temperature control unit or a Hielcher sonicator (UIP1000 hd). In order to obtain full dispersion of the sample, the sonicated samples were centrifuged in an Eppendorf centrifuge tube for 20 minutes at 20000×g until only a minor pellet was formed. After pelleting of the undispersed material, the supernatant was very dark with the CNT, even after 100 fold dilution in the same buffer. The last step was centrifugation of the suspension for 60 minutes at 7000 rpm using a Sorval SLA 3000 centrifuge.

Results

Table 2 hereinabove, presents the results of the CNT dispersion experiments. The SP1 variants described in Table 2, are heat stable and generally protease resistant, however, incubation with alcalase (1000-fold dilution) causes a shift in the molecular weight relative to samples not treated with alcalase. In all cases the apparent molecular weight of the alcalase-treated SP1 variants was still higher than those of native SP1, indicating that some but not all the amino-acids derived from the CNT binding peptides were removed.

As can be seen in Table 2, fusion of copies of these CNT binding peptides to SP1 N-terminus improves the SP1's ability to disperse multi wall carbon nanotubes (MWCNT) in a solvent, while native SP1 protein affords MWCNT dispersion only at high SP protein concentrations (approx. 1 mg/ml). As can further be seen in Table 2, the fusion proteins have a much higher CNT-binding activity. The greatest CNT dispersing capability was observed with L1 (SEQ ID NO: 6), an SP1 polypeptide with the HWSAWWIRSNQS peptide (SEQ ID NO: 10) fused to the N-terminus, which allowed MWCNT dispersion at the relatively low concentration 0.004 mg/ml. Fusion of SP1 with the other CNT-specific peptides L2 (SEQ ID NO: 14) and L3 (SEQ ID NO: 8) [HSSYWYAFNNKT (SEQ ID NO: 11) and DYFSSPYYEQLF (SEQ ID NO: 12) peptides respectively] also resulted in greater CNT dispersing activity than native SP1. Using the L3-SP1 the Hielcher sonicator, maximal CNT concentration was 40 mg CNT/gr fabric, or 4%. If SP1 solubility is as high as 150 mg/ml theoretically, maximal CNT concentration, can be as high as 30%.

Variants L2-SP1 (SEQ ID NO: 14) and L3-SP1 (SEQ ID NO: 8) differ from other SP1 variants in that they form both soluble and insoluble protein found in inclusion bodies (IB). The protein found in IB can be dissolved in the presence of urea and refolds upon urea dilution. While properly folded L2-SP1 forms complexes and was protease resistant, the dissolved L2-SP1 from IB did not form complexes and was protease sensitive. The L2-SP1 and L3-SP1 from inclusion bodies can disperse CNT but with much less efficiency than the soluble protein (Table 2).

As can be seen in Table 2 hereinabove, the minimal SP1 concentration required for CNT dispersion depends on the sequence of the peptide fused to the N-terminus.

In the case of L1-SP1 (SEQ ID NO: 6), an ion exchange purified protein was treated with alcalase, and the protein underwent N-terminus sequencing and molecular weight determination using MOLDY-TOF. The results indicated that 8 amino acids were digested by the alcalase from its N-terminus, leaving the SNQS peptide fused to the protein N-terminus. It is noted herein that the SP1 variant with an insertion of the SNQS peptide at the N-terminus (L6-SP1, SEQ ID NO: 15) exhibited similar characteristics, namely mobility in SDS PAGE and CNT dispersion ability, as compared to the alcalase-treated L1-SP1.

In addition to the CNT specific peptides, fusion of the silicon/titanium oxide binding peptide (RKLPDAA) (SEQ ID NO: 5), which yields the SP1 variant mtbSP1 (SEQ ID NO: 3), was found to facilitate CNT dispersion at lower concentration than native SP1.

For industrial applications it is preferred to keep the protein production costs as low as possible, and to make sure that other peptides that may exist in the crude extract of transformed cells expressing a recombinant protein do not interfere with the variant SP1's CNT dispersion capability. To test this facet, crude extract obtained from bacteria transformed to express L1-SP1 was exposed to combinations of heat and protease treatments, and was then assessed for the retention or loss of CNT dispersion activity, as presented in Table 3 below.

olysis used during the preparation of the mutant, did not abolish the capacity to disperse CNT.

A direct demonstration that L1-SP1 binds to CNT and forms a complex was obtained by comparing a suspension of a sample of L1-SP1 (SEQ ID NO: 6) with CNT (L1-SP1/CNT), a sample of the protein without CNT (L1-SP1) and a filtrate (0.22 micron filter) of these two samples before and after boiling. Both the boiled and not boiled samples were analyzed by SDS PAGE.

The boiled L1-SP1 was detected as a band of the monomeric form and a band of the trimeric form, while the unboiled L1-SP1 appears as a high molecular weight complex only.

A large fraction of the CNT was excluded by filtration, therefore longer than 0.22 micron. The proportion of the SP1 trimer bands in the absence of CNT was lower than that detected in the presence of CNT, both in the filtrates and in the unfiltered samples. Apparently not all the protein dissociated upon mixing with the SDS Tricine sample buffer and SDS PAGE application.

Another indication that the L1-SP1 protein (SEQ ID NO: 6) binds to the CNT comes from the protein determination assay (Bradford protein assay) of both mtbSP-SP1/CNT suspension and the microfiltration (0.2 micron) flow-through, demonstrating that about 50% of the protein after CNT complexing is larger than the 0.2 micron pore size and is retained by the filter (data not shown).

Yet further evidence for the formation of a SP1-CNT complex is seen in the results of ethanol precipitation (Table 3): While uncomplexed protein does not precipitate with 50% ethanol, SP1-CNT does precipitate with 50% ethanol. CNT precipitate also with GuHCl (100 mM) and in acidic pH (by adding HCl or acetic acid), however, while GuHCl does not induce uncomplexed protein precipitation but acidic pHs does. This phenomenon is used to determine CNT concentration to fabrics.

Heat stability, protease and alkali resistance of L1-SP1-CNT complex: To assess the stability of the complex, L1-SP1/CNT was subjected to heat treatment (100° C.; 10 minutes or 80° C.; 30 minutes) both at pH 8.0 and pH 11, or proteolysis at pH 8.0. Incubation of L1SP1/CNT samples, at different pHs, were followed by high speed centrifugation (20 minutes; 20000×g) and 10-fold dilution of the supernatant. The results of the heat and proteinase assays demonstrate that the SP1/CNT complex is heat stable and protease resistant, allowing economically desirable heat drying and powdering of the complex prior to its dispersion in important polymeric compounds, such as epoxy.

TABLE 3

| | Crude extract treatment | | CNTs dispersion | |
|---|---|---|---|---|
| | Heat treatment | Alcalase treatment | Maximal dilution | Minimal protein concentration μg/ml |
| Standard treatment. | 80° C., 30 minutes × 2 | + | 1:26 | 10 |
| Heat treatment. | 80° C., 120 minutes | – | 1:26 | 9.3 |
| Alcalase treatment with final inactivation of alcalase | 80° C., 30 minutes after alcalase treatment | + | 1:26 | 6 |
| Alcalase treatment without final Inactivation of alcalase. | — | + | 1:26 | 11 |

As can be seen in Table 3, the heat treatment of crude extract of L1-SP1, up to 120 minutes at 80° C. and prote- The high durability of the SP1/CNT complex allowed the development of simple method to obtain a dry pellet of SP1/CNT complex that can easily re-dispersed in water. The process includes first dispersion of 4% CNT, followed by three steps of wash and precipitation by 1:5 dilution in ethanol (final 99% ethanol), and dehydration using a vacuum pump.

Example 5

SP1 Variants Binding to Aramid (e.g. KEVLAR™)

Material scientists and engineers are excited by the possibilities for creating super-strong, high-performance polymer composite materials using carbon nanotubes. Currently, all existing methods of fabricating CNT-polymer composites involve complicated, expensive, time-demanding processing techniques such as solution casting, melting, molding, extrusion, and in situ polymerization, requiring that the nanotubes either be incorporated into a polymer solution, molten polymer or mixed with the initial monomer before the formation of the final product (e.g. yarn, ribbon or film). This is unsuitable for insoluble or temperature sensitive polymers, which decompose without melting.

Aramid polymers (e.g. KEVLAR™) is a well-known high-strength polymer with a variety of important applications such as pneumatic tire tread and sidewalls, bullet-proof vests and car armor plating. However, aramid (e.g. KEVLAR™) is not soluble in any common solvent and, having no melting point, decomposes above 400° C. As a result, aramid (e.g. KEVLAR™) fibers must be produced by wet spinning from sulphuric acid solutions. Binding of SP1/CNT complex to aramid (KEVLAR™) was assessed for effective post-processing incorporation of carbon nanotubes into already formed polymer products, such as, for example, aramid (KEVLAR™) yarns.

CNT binding to the fabric via the protein increases its surface area, allowing better interaction with the fiber and induces cross linking between the fibers. In addition, protein biding to the fiber by itself may improve the interaction with the polymer through reactive groups on the protein surface. It is demonstrated that some SP1 variants that bind CNT also bind to structural fibers.

Materials and Methods

L3SP1/CNT solution (SEQ ID NO: 8), in different concentrations (22 μg/ml, 44 μg/ml, and 88 μg/ml samples in 10 mM NaPi, pH-8) was incubated with 100 mg of aramid (KEVLAR™) fabric in a rotary shaker at 25° C. for 16 hours, followed by extensive wash with the same buffer to remove traces of the unbound protein and CNT, until the solution was colorless, indicating absence of CNT, and until no protein was detected in the wash. CNT binding to the aramid (KEVLAR™) was assessed by darkening of the aramid (KEVLAR™) fibers. SP1 binding to the washed aramid (KEVLAR™) was determined by reacting the aramid (KEVLAR™) with 2 ml of BCA protein assay reagent (Pierce, cat No. 23227) for 30 minutes at 37° C., and measurement of optical density at 562 nm. The amount of protein bound was calculated and plotted, and the results are presented in U.S. Pat. No. 8,957,189 herein incorporated by reference in its entirely.

SP1/CNT binding to aramid was evaluated by precipitation, light transmittance (spectroscopy, visual inspection) and surface resistivity, as detailed above.

Results

Comparison of the bound and unbound fibers after incubation with the L3 SP1/CNT complex, indicated extensive binding of the CNT, even after exhaustive washing (not shown). BCA protein assay also showed that SP1/fabric (w/w) ratio is approximately 2 mg protein/g fiber (2/1000). In parallel experiments it was demonstrated that L-1-SP1 (SEQ ID NO: 6) and L-4 SP1 (SEQ ID NO: 9) also bind to aramid (KEVLAR™). Following incubation with L3-SP1/CNT aramid (KEVLAR™) fibers turned dark in color, indicating binding of the CNT thereto even after extensive wash. Incubation of 30 mg aramid with 180/1000 w/w L4-SP1-CNT dispersion, followed by bath sonication (90 min temperature ranging between 30-70° C.), fiber removal, extensive washing (using the buffer) and boiling (10 min in 60 ul) to extract bound protein and CNT produced darkened fibers bearing bound protein as well as bound CNT.

CNT dispersion (0.1% CNT (Arkema, code C100), using L3SP1 (SEQ No 8)) was incubated with aramid fabric (KEVLAR style 120 plain weave 195 Denier, 58 g/m square; 22 ml suspension per g fabric) by agitation (1 h; 25° C.; 150 rpm) followed by extensive wash in the same buffer, and drying in the open air, overnight CNT content on fabric was about 9 mg/g fabric. Note that the bound CNT dramatically increases surface area, and that the CNT are in close contact with one-another, affording improved electrical conductive properties.

Example 6

SP1 Variants Binding to Carbon Fabric

Carbon fabric is a well-known high-strength material with a variety of important applications in aerospace and automotive fields, as well as in sailboats and sport equipment, where its high strength-to-weight ratio is of importance. Continuous carbon fiber/epoxy composites have been widely used for structural applications due to their excellent mechanical properties. The polymer is most often epoxy, but other polymers, such as polyester, vinyl ester or nylon, are also used. However, their matrix-dominant properties, such as in-plane and inter-laminar shear properties, are much weaker than their fiber-dominated properties, thus limiting the benefits of these conventional composites. In addition, it is known that composites exhibit lower longitudinal compressive strength, a matrix-dominated property, than tensile strength.

CNT binding to the fabric via the protein increases its surface area, allowing better interaction with the fiber, and induces cross linking between the fibers. In addition, protein binding to the fiber by itself may improve the interaction with the polymer through reactive groups on the protein surface. It is demonstrated that some SP1 variants that bind CNT also bind to structural fibers.

Production of SP1-CBD Dissolved Inclusion Bodies

Materials and Methods

SP1-CBD is expressed in bacterial hosts as insoluble inclusion bodies (IBs), as described in U.S. Pat. No. 7,253,341 to Wang et al. Briefly, SP1 cDNA encoding a 108 SP1 amino acid sequence (SEQ ID NO: 88) was cloned into an expression vector bearing a nucleotide sequence encoding a 163 amino acid CBD domain of *Clostridium cellulovorans* cellulose binding protein A (SEQ ID NO: 87). The resulting nucleic acid construct encoded a SP1-CBD fusion protein which includes a peptide linker (SEQ ID NO: 89). Following cloning, the resulting plasmid was used to transform *E. coli* strain BL21 (DE3). Recombinant CBD-SP1 fusion protein synthesis was induced in BL21 (DE3) by the addition of IPTG (isopropyl-D-thiogalactoside) to a final concentration of 1 mM to mid-log phase of the bacterial culture, followed by five additional hours induction at 37° C. Recombinant SP1-CBD fusion protein (SEQ ID NO: 86) was detected in inclusion bodies (IB), and the inclusion bodies isolated and purified. Briefly, IBs containing SP1-CBD were dissolved in Trisma base (20 mM), NaOH (8 mM) (30, min on ice, 1:200 ratio (w/v)), followed by high speed centrifugation, 13,000 rpm for 30 min. The supernatent was diluted 1:10 in water and the pH was adjusted to pH=8.2 (using NaPi buffer, 100 mM pH=6.8).

SP1 Polypeptide-CNT-Complex Binding to Carbon Fiber

Carbon (also glass and aramid) fabrics were washed with phosphate buffer (10 mM; pH 8) in a rotary shaking bath (160 r/min, 10 min, at room temperature) and then incubated in a rotary shaking bath (1 h each side, 160 r/min, room temperature) containing aqueous SP1/CNT (SEQ ID NO: 8) suspension (suspension/fabric w/w ratio was 5:15; CNT concentration was 0.05-0.4%, termed the "applied fraction"). The remaining suspension of CNTs was termed the "unbound fraction". SP1/CNT PAN fabrics were then extensively washed with deionized water, termed the "wash fraction", until the washing solution became colorless. The treated fabrics were then air-dried for 1 week. To confirm and quantify CNT binding to the fabric, the amount of CNT in the "unbound þ washed" fractions was subtracted from its amount in the "applied" fraction. For analytical purposes, the concentrations of SP1/CNT complex in dispersions were determined by two methods with similar results. The maximal CNT binding as measured by this "subtraction" method was about 4 mg CNT/gr fabric 0.4%:

1. Gravimetric method when the dispersion is coagulated & flocculated by using HCl (0.3%), followed by centrifugation (10 min, 2500 g) and pellet dehydration in the oven (80 C, overnight), followed by dry weight measurements.
2. Measuring absorption of diluted L3-SP1/CNT suspension before and after its incubation with the fabric, including the fabric washing solutions, using standard spectrophotometer or 96-well plate reader at 405 nm
3. Bound SP1/CNT can be extracted from wet fabric using 0.5% SDS, but not by using water. However, this extraction method is not practical for evaluation of amount of bound SP1/CNT because of the following reasons: even after very intensive extraction a significant proportion of the CNT is still bound to the fibers (evaluated by HR-SEM analysis); small broken pieces of fibers are released by the extraction mixture.

TABLE 4

Characterization of dispersion made by conjugation of the SP1 protein together with carbon nanoparticles (CNP; multiwall carbon nanotube and carbon black)

| | Multi-walled CNT Graphi | Carbon Black | | | | |
|---|---|---|---|---|---|---|
| Carbon nanoparticle | strength ® C-100 Arkema | N326 | Conductive CB | CB 220 | CB 550 | CB 660 |
| SP1 Variant | Heat stable crude extract of recombinant L3SP1 protein | | | | | |
| Maximal SP1/CNP dry weight/weight ratio | 2.9 ± 0.5 | 7 | 5.5 | 4.5 | 5.5 | 5.5 |
| Dispersion Method | | | Sonication[1] | | | |
| SP1/CNP concentration | 4% | 17% | 4% | 4% | 4% | 4% |
| Fraction of CNP remain in supernatant upon centrifugation [2] | <25% | <30% | 45% | 25% | 20% | 75% |
| Long term stability at room temp [3] | <12 months | <4 month | ND | ND | ND | ND |
| pH stability | 5.5-11 | 5.5-11 | ND | ND | ND | ND |
| stability in the presence of divalent cation ($Ca^{+2}$ $Mg^{+2}$) | >0.3 mM | >3 mM | | | | |

[1]Sonication was conducted using a Hielscher Ultrasonics processor UIP1000 (1000 W), frequency: 20 kHz (autoscan), amplitude: 25 mm (85%), 40 min sonication.

[2] Stability upon centrifugation, a quantify measure for dispersion quality, was assessed by calculating the fraction of CNP remaining in the supernatant under centrifugation (dispersion was diluted to 0.1% in sodium phosphate buffer (10 mM; pH 8.0); Supernatant was collected after centrifugation (30 min; 3000 g, in 50 ml Falcon tube; 25° C.)). Both gravimetric and spectral methods were used to determine the ratio of CNP concentration before and after centrifugation. Gravimetric method: CNPs were flocculated with 0.3% HCl, spun down (10 min, 4700 g), followed by pellet dehydrated (80 C., overnight), and dry weight measurement (detonated supernatant (S)). The same procedure was conducted also on the dispersion before centrifugation (detonated total (T)). Stability upon centrifugation was calculated according to the following equation: 1 − (T − S)/(T). Spectral method: optical density of diluted dispersion was determined at 405 nm using 96 plate reader. Note that there is a linear correlation between CB concentration and optical density. Ratio of the optical density of the dispersion before and after centrifugation was determined.

[3] Long term stability was determined upon long term storage of concentrated dispersion at room temperature as described in 2.

FIG. 1A is an HR SEM image of SP1/CB (N326) dispersion demonstrating that the dispersion is nano-metric (particle/aggregate size is <500 nm).

Figure 1B:
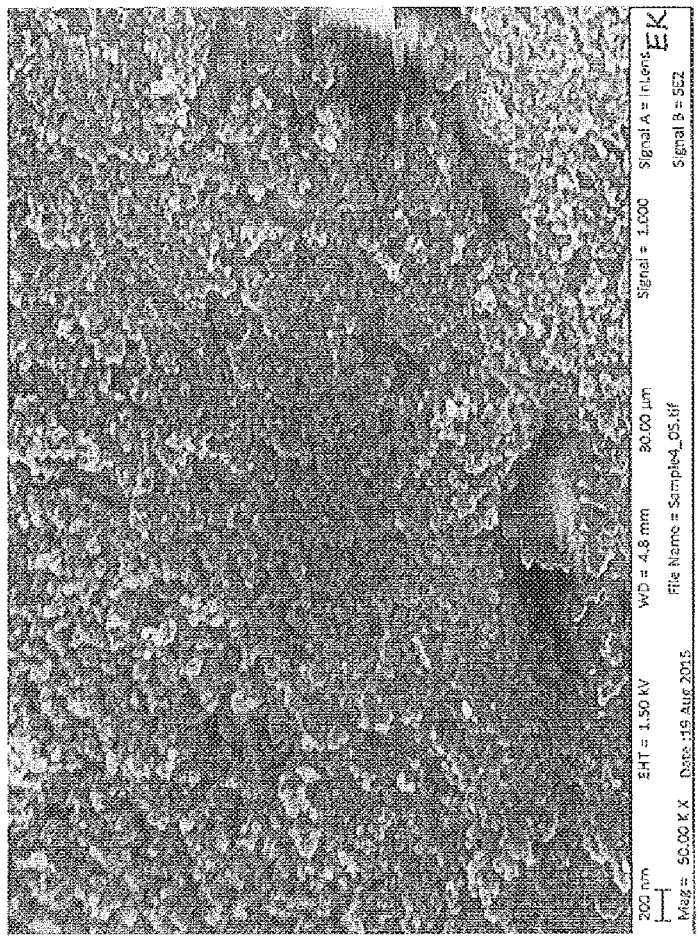

FIG. 1B is an HR SEM image SP1/CB (N326) coating of a polyester fiber.

Figure 2A:
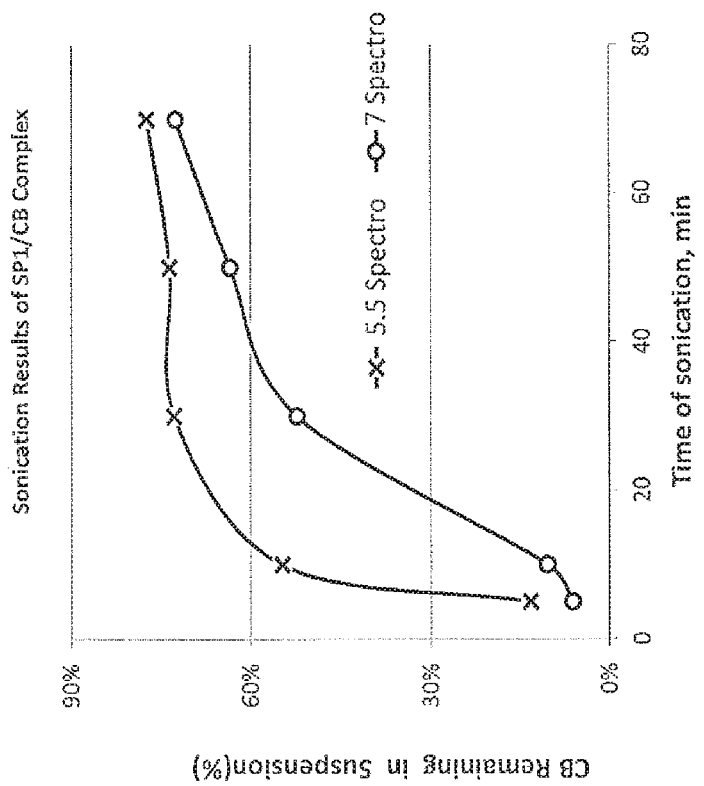
FIG. 2A is a plot depicting the effect of time of sonication on SP1/CB dispersion at different SP1/CB concentration and dry w/w ratios.
Figure 2B:
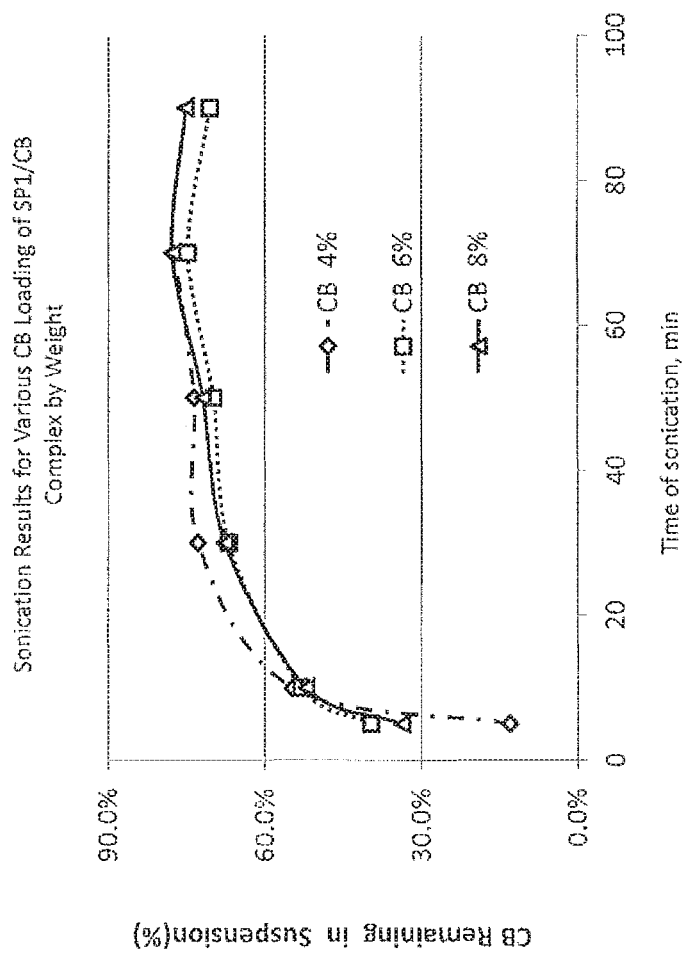
FIG. 2B is a plot depicting suspension as a function of sonication time for various loading of CB in the SP1/CB complexes.

FIG. 2A depicts the effect of time of sonication on SP1/CB dispersion at different SP1/CB concentration and dry SP1/CB w/w ratio.

The Spectro measurements relate to spectroscopic measurements and are indicative of CB concentration as a linear relationship of with optical density. The optical density of diluted dispersion was determined at 405 nm using a 96 plate reader. The ratio of the optical density of the dispersion was determined before centrifugation and several times afterwards as a function of sonication as depicted.

Minimal time of sonication is 30 min at low dry SP1/CB w/w ratio (5.5) regardless SP1/CB concentration, but longer time of sonication (60 min) is required at higher dry SP1/CB w/w ratio (7). Maximal SP1/CNT and SP1/CB concentration are 4% and 17%, respectively. Long term stability tests at room temperature of 4% dispersion SP1/CNT and SP1/CB-N326 are <12 m and <4 m, respectively (Table 4). The SP1/CNT and SP1/CB dispersions are stable at wide range of pHs (pH=5.5-11) but precipitate in the presence of divalent cations (Mg+2 and Ca+2) in concentrations of >0.3 mM and >3 mM, respectively.

SP1/CNP precipitation at low pH and in the presence of divalent cations have several practical implications: for example, low pH and the presence of divalent cations are useful conditions for CNP recycling and for toxic waste reduction. All steps with the water based dispersion of SP1/CNT and SP1/CB were carried out with de-ionized water (Concentration of divalent cations <10 μM).

FIG. 2B is a plot depicting suspension as a function of sonication time for various loading of CB in the SP1/CB complexes Dispersion of Other Types of Carbon Black Conductive CB, CB220, CB550 and CB660

The same methodology used for Graphistrength® C-100 and CB-N326, was used to disperse other types of carbon black: conductive CB, CB220, CB550 and CB660. All CNPs were dispersed to some degree (Table 4). The difference in stability upon centrifugation may be attributed to differences in specific gravity.

CNP/protein (Heat stable crude extract of recombinant L3SP1 protein) ratio is 2.8 and 7 for multiwall carbon nanotube (MWCNT) and carbon black (CB), respectively. Maximal dispersion concentration is 4-5% and 17% for multiwall carbon nanotube (MWCNT) and carbon black (CB), respectively. Note that for single wall CNTs which display much higher surface specific area, CNT/protein ratio is 8-fold lower. Therefore, much lower protein concentrations are needed in order to disperse CNP with pure protein (MWCNT/protein ratio=20), but since protein purification is costly, crude extract is used without further purification. In the absence of protein, the CNPs are not dispersed but rather readily precipitate on the bench. Dispersions stability for few months, also at elevated temperature is essential for industrial application. The complexation of CNP with SP1 protein enables the dispersion of CNPs and enhances its stability. SP1/CNP complex precipitate. Investigation of conductive CB will be further discussed.

Layer by Layer Coating

An important feature of the current invention is the "layer by layer coating" procedure, as described above, since it allows controlling CNP load on the yarn in a cost effective way minimizing waste, if any, of expensive nanoparticles. When low SP1/CNP concentration is applied (0.05% in dispersion; when liquor/fabric ratio=7 this value is equivalent to 3.5 g/Kg yarn) it is totally depleted from the applied fraction and when PEI is used in the next step it allows binding of higher load of SP1/CNP (equivalent to 7 g/Kg yarn with total load of 10.5 g/Kg), and so on. It is important to note that though increasing SP1/CNP concentration in the applied fraction may increase bound SP1/CNP.

Results

Kevlar treatment with both RFL and SP1/CNP don't change strength at max load and elongation at break. SP1/CNP treatment don't change Strength at 1% elongation (N)) (reduces flexibility), in contrast with the RFL treatment that dramatically increase Strength at 1% elongation, which is important when the reinforcement cord is stretched.

Electrical Conductivity

FIG. 3A is a flow chart depicting a non-limiting general procedure employed in the treatment of Polyethylene terephthalate (PET) yarn to render it electrically conductive in a range of 1 ohm/m to 20 Mega ohm/m. In certain a certain embodiment resistance can range between 0.1 Ω/m 10 mega Ω/m.

It should be appreciated that in certain embodiments, non-polymeric yarn is employed. As shown, the process is implemented in two primary stages; the SP1/CNP loading stage 15 and the copper loading stage 16, according to and embodiment.

SP1/CNP loading stage 15 stage commenced with the preparation of a SP1/CNP dispersion at step 20, as set forth above, to be loaded after appropriate preparation of the PET yarn.

In step 21, the yarn was de-sized using soda ash triton or another scouring solution in an Ugolini dyeing machine, for example, with smart and controlled winding on bobbin to facilitate uniform coating.

In step 22, high molecular weight (60 KDa) branched PEI was dissolved in carbonate buffer (20 mM at a pH=8.8) and applied at 45° C. when the PEI/yarn ratio=0.035%-1.4% by weight.

In step 23, the yarn underwent extensive washing with carbonate buffer equilibrium to prevent the low concentration PEI to aggregate and to precipitate CNP.

In step 24, the SP1/CNP dispersion is brought into contact with the yarn when CNP/yarn ratio=0.35%-0.9% by weight at 45° C. Typically this process takes about 0.5-1 hour until complete depletion of the SP1/CNP from the dispersion is achieved.

In step 25 an evaluation of the loading of the composition coating is performed. If the composition load is less than about 1 g of SP1/CNP composition/kg of substrate, for example, processing returns to step 22 for additional PEI and CNP treatment. Depletion of the SP1/CNP is assessed by measuring the fraction of CNP remaining in the supernatant upon high-speed centrifugation under standard conditions (0.1% in NaPi buffer; 30 min at 3000 g, at room temperature), followed by flocculation of the supernatant with 0.3% HCl, centrifugation (10 min at 4700 g), pellet dehydration (80° C., overnight) and dry weight measurement.

If determined that that the SP1/CNP coating has achieved a threshold thickness, operations continue to the copper loading stage 16. It should be noted that various threshold thicknesses of SP1/CNP coating may be employed in accordance with the particular application.

The copper loading stage 16 commences at step 26 with a PEI treatment to facilitate bonding between the SP/CNP coating and palladium when applied. It should be noted that in certain embodiments other cationic polymers are employed to facilitate bonding like copolymers and other polyamines.

In step 27, a Palladium coating is applied to the SP1/CNP layer by contacting the coated SP1/CNP substrate with a Palladium solution. Palladium salt Sodium tetra-Chloro Palladate ($NaPdCl_4$) and Palladium Chloride ($PdCl_2$), sources were purchased from Acros and used as received. In one test run, $NaPdCl_4$ was dissolved in soft water in concentration ranging between 0.01 mM-5 mM. All palladium solutions prepared in PIPES buffer (20 mM, pH=6.8). In another test run $PdCl_2$ was dissolved in water in presence of 5% technical ethanol without buffer addition and used shortly after preparation.

In general, the concentration of $NaPdCl_4$ can range from 0.1 mM-1.0 mM.

In a first run, Pd application was performed in an Orbital Shaker Incubator machine at 45° C. and a speed of 140 rotations/hour in which 1-10 meters of complex coated yarn was submerged in 100 mL palladium solution and shaken for five minutes.

Figure 3A:
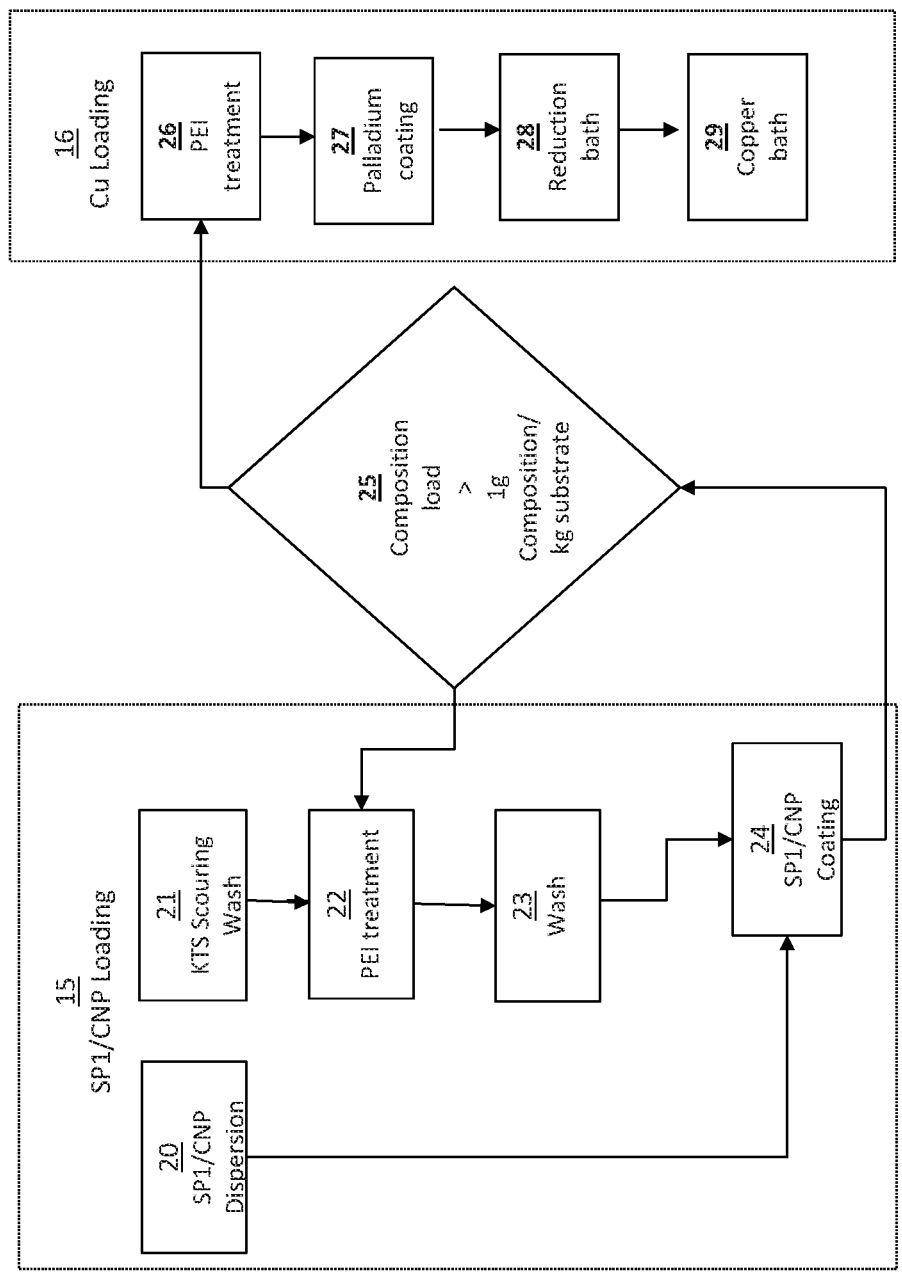
FIG. 3A is a flow chart depicting steps associated with the production of conductive yarn.
Figures 3B, 3C:
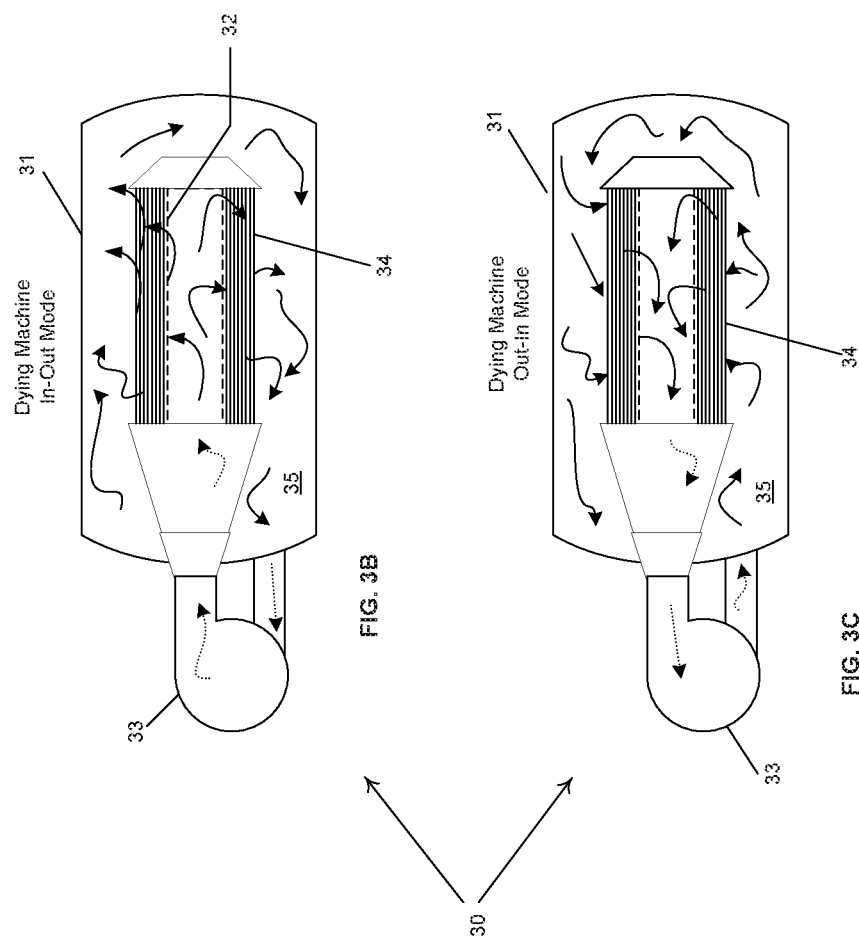
FIGS. 3B and 3C are schematic, side cross-sectional-views of a dyeing machine in an in-out and an out-in mode, respectively.

In a second run, bulk experiments were performed using a Mini Symplex Ugolini lab dyeing machine depicted in FIGS. 3B and 3C.

Specifically FIGS. 3B and 3C depict schematic views of a sample dying machine 30 processing during both in-out and out-in modes, respectively. Specifically, dying machine 30 is fitted with a perforated cylinder 32 mounted in a treatment vessel 31 though which a process liquid 35 is circulated by pump 33. Yarn 34 is wrapped around cylinder 32 during processing and the treatment liquid 35 is pumped into cylinder 32 through yarn 34 and the perforations in cylinder 32 when operating in out-in mode as depicted in FIG. 3B. In the in-out processing mode, liquid is pumped in the opposite direction out of cylinder 32 through its perforations and through the yarn 34 as depicted in FIG. 3C. It should be appreciate that various dyeing machines providing such functionality are may be employed.

As noted above, the bulk run was performed on 100 g of complex-coated yarn submerged in 0.7 L Pd solution in a Mini Symplex Ugolini lab dyeing machine with a kier volume of 0.7 L for about 0.5 hour at a liquor/yarn ratio=7 with the following pump working parameters:

In-out time 2 min.
Out-in time 1 min.
Pump output 80%.
Pressure during the process ~1 bar
Δ pressure ~0.1 bar The pH, the temperature, the pump output volume and pressure were monitored in a data logging system. This step may be repeated several times using water washes between the Pd treatments for better uniformity.

Returning now to the process, in step 28, the Palladium coated substrate was reduced in a reduction bath. Reduction solution was prepared using Borane dimethylamine complex (2.5 g/L), tri-Sodium citrate dehydrate (25 g/L) and lactic acid (25 g/L). pH of 6.7 was achieved with addition of NaOH (1M). All the reagents were purchased from Acros (Borane reagent), Merck (Citrate), Fisher Chemicals (Lactic acid) and used as received. The solution were stored for several days and found to be effective as it was prepared. Lower concentrations were also found to be effective as well. It is possible to use even lower concentration of reduction solution up to 10% of the standard solution.

It should be appreciated that in a certain embodiment, the application of a metallic catalyst, like Pd, can be achieved after a five seconds contact time of substrate and solution and in other embodiments the application can take as long as one hour.

In step 29, following a water wash, the Palladium coated substrate was subject to a copper treatment though submersion in a copper solution purchased from Amza. The active solution includes the following ingredients:

A—(Sulfuric Acid Copper (2+) pentahydrate (10-25%), Ethylene-dinitro-tetrapropan-2-ol (3-5%), methanol (1-2%))
B—(ethylene-dinitro-tetrapropan-2-ol (25-50%))
C—(Sodium hydroxide (25-50%))

Ingredients A, B and C were mixed before using in a standard ratio: A (60 mL), B (60 mL) and C (25 mL) for about 1 L solution.

The copper treatment was implemented in both bath and bulk processing.

Bath methods performed in 1 L glass Beaker containing 500 mL of copper solution with mild stirring to prevent yarn damage. The glass bath heated directly on a heat plate to 40° C. and the temperature measured inside the bath. The yarn was slowly dipped inside the bath while stirring the Cu solution. The exemption of hydrogen gas exemplified reaction progress.

Generally, yarn remains in the Cu bath for a time period ranging from 30 seconds to one hour depending on the target Cu thickness and conductivity. It should be appreciated that in a certain embodiment, the application of a metallic coating, like Cu, can be achieved after a five seconds contact time of substrate and solution and in other embodiments the application can take as long as one hour.

Following is summary of the relevant operational parameters employed during the Pd coating, reduction, and Cu coating operation 37:

| Step | Bath | Ugolini Machine |
| --- | --- | --- |
| Coating conditions | 1-10 m yarn, in 100 mL solution, 40° C. Gentle flow 140 RPM, high Liquor/textile ratio = 700 | 100 g yarn (250-500 m), 0.7 L solution, 37° C. Liquor/textile ratio = 7 Pump work parameters: in-out time 2 min, out-in time 1 min, pump output 80%, pressure during the process ~1 bar, Δ pressure ~0.1 bar. |
| 38 Palladium | 0.01 mM-5 mM $NaPdCl_4$ dissolved in PIPES buffer (pH 6.8, 20 mM), 5 min. | 0.3 mM-1 mM $NaPdCl_4$ dissolved in PIPES buffer (pH 6.8, 20 mM), 30 min. |
| 39 Reduction Bath | 5 mM-40 mM of Boron reagent concentration, Lactic acid (8-80 mM) and tri Sodium Citrate salt (25-270 mM), pH 6.7 was achieved by adding several mL of NaOH (1M). All the reagents were | 5 mM-10 mM of Boron reagent, Lactic acid (8 mM) and tri Sodium Citrate salt (25 mM), pH 6.7 was achieved by adding NaOH (1M). All the reagents |

-continued

| Step | Bath | Ugolini Machine |
|---|---|---|
| | dissolved in soft water. 1 m yarn, 100 mL solution, 40° C. 140 RPM, Liquor/textile ratio = 700, 1-5 min. | were dissolved in soft water. 30 min. |
| Water Wash | 3 washes, 1 min each, with 100 mL water. | 2 washes, 5 min each, with 0.7 L water. |
| 41 Copper Bath ($CuSO_4$) | 25° C.-75° C., 10 seconds - 40 minutes. Standard concentration ($CuSO_4 \times 5H_2O$ 40 mM, ethylene-dinitro-tetrapropanol 6 mM, NaOH 20 mM pH 13), 20% of standard. | 45° C., 30 minutes. Standard concentration. 1-4 repeats. ($CuSO_4 \times 5H_2O$ 40 mM, ethylene-dinitro-tetrapropanol 6 mM, NaOH 20 mM pH 13 |
| Final Water Wash | 3 washes, 1 min each, with 100 mL water. 12 h drying at 45° C. | 3 washes, 5 min each, with 0.7 L water. 12 h drying at 50° C. |

Bulk processing was employed for the copper treatment coating and it was found that three or four repetitions were required to achieve the resistance of 2,000 Ω/m.

The copper coated yarn was dried in oven at 50° C. for 12 hours to stabilize it and X-Ray spectroscopy employed to measure the thickness of copper layer measured using Fischerscope™, after drying and general method of thickness calculation "Cu/Base; plastic".

An evaluation of the effects of CB and PEI depositions was performed using 1100×2 dtex treated with 2 layers of CB 0.7 g/Kg and two layers of and PEI of 0.14 g/Kg each. The concentration of PEI was 0.05%-0.0005% and the $NaPdCl_4$, reduction, and $CuSO_4$ baths were implemented in accordance with procedures described above.

| Effect of PEI, Amount of SP1/CB complex and $CuSO_4$ Bath Concentration on Resistivity | | | | | |
|---|---|---|---|---|---|
| Time | Effect of PEI at Constant SP1/CB Complex load | | | Effect of SP1/CB Complex Load at Two PEI loads | |
| in Cu | | 0.14% | | 0.07% | 0.14% |
| bath (min) | CB PEI | 0.35% cap | 0.035% cap | 0.0035% cap | In process 0.7 w % | In process 0.35 w % |
| 60 | | — | 103 | Uneven | | |
| 30 | | 13 | 182 | Uneven | | |
| 20 | | 85 | 4600 | | 92 | 4,600 |
| 10 | | >20M | >20M | | 290 | >20M |
| 7 | | — | — | | | |
| 5 | | >20M | >20M | | 755 | >20M |

The conclusion was that a concentration of 0.0035 g PEI/kg yarn was too low and led to uneven coating for this particular trial; although, in a certain embodiment it such a low concentration of PEI is desirable. The optimal concentration for single CB layer was found to PEI be 0.0065 g/kg yarn at the given experimental conditions. In a certain embodiment the concentration ranges up to 10% w/w.

Figure 4A:
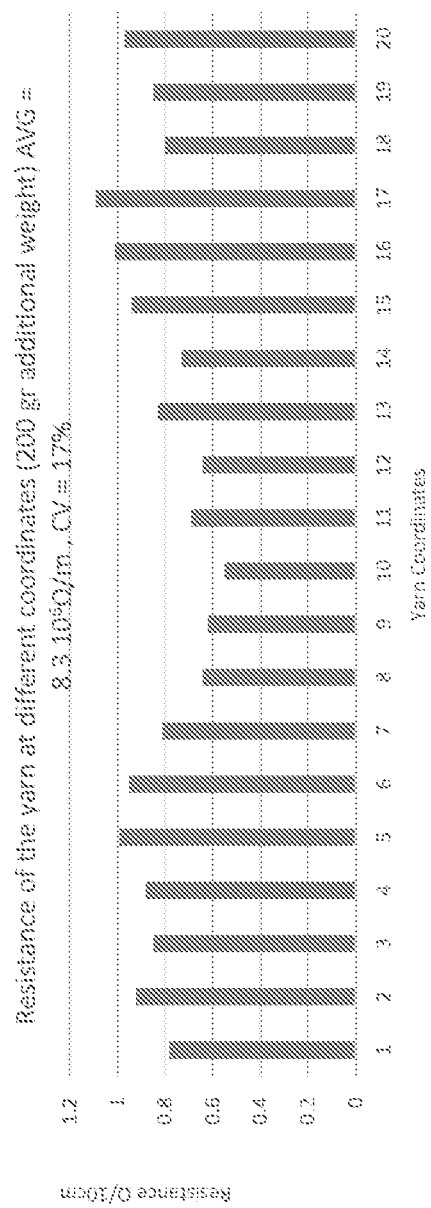
FIG. 4A is a chart depicting electrical resistance as a function of yarn length under tension.

FIG. 4A is a chart depicting results from experimentation directed at establishing optimal amounts of a competing agent $CuCl_2$ during Pd treatment. The competing agent was employed to delay bonding of the Pd and the SP1/CNP complex until the Pd solution permeated through layers of yarn during treatment. Experimentation showed that Pd bonding in the absence of competing agent resulted in a quick Pd bounding with the outer layers of yarn and insufficient bonding at the underlying layers. During experimentation, 1100×3 dtex polyester yarns were treated using Ugolini machine conducted in a bath for 10 minutes at 40° C. The resistivity of the conductive yarns was then measured at various yarn lengths under tension of a 200 gram weight.

Concentrations of $NaPdCl_4$ and $CuCl_2$ reagents and corresponding resistance measurements and uniformity results are set forth in the following table:

| | $NaPdCl_4$ Treatment and Competing Agent | | | |
|---|---|---|---|---|
| | No Competing Agent 1 mM $NaPdCl_4$ | No Competing Agent 0.3 mM $NaPdCl4$ | With Competing Agent 1 mM $NaPdCl_4$ + 10 mM $CuCl_2$ | With Competing Agent 1 mM $NaPdCl_4$ + 3 mM $CuCl_2$ |
| Resistance Ω/m (AVG) | $1.8 \times 10^6$ | $7.3 \times 10^7$ | $8.3 \times 10^6$ | $4.9 \times 10^7$ |
| Uniformity (CV) | 118% | 56% | 17% | 135% |

As shown, the optimal ratio of reagents at these experimental conditions is that producing the smallest CV of 17%

Figure 4B:
FIGS. 4B-4D are enlarged images of wound yarn depicting progressive stages of copper covering a carbon black underlayer.
Figure 4C:

FIGS. 4A-4C are microscope images of 1100×3 dtex PET yarn enlarged 250× and depicts discontinuities in the copper coating. The orange-brown areas are characteristic of copper coating whereas the black areas are characteristic of carbon black underlayer.

Figure 4D:
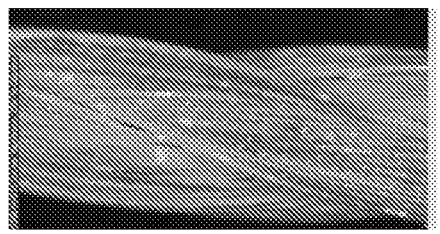

The sample depicted in FIG. 4B was treated with 0.3 mM $NaPdCl_4$, whereas the sample depicted in FIG. 4C was triple treated with 0.3 mM NaPdCl, and the sample depicted in FIG. 4D was treated with 1 mM $NaPdCl_4$ together with 10 mM $CuCl_2$.

Figure 5A:
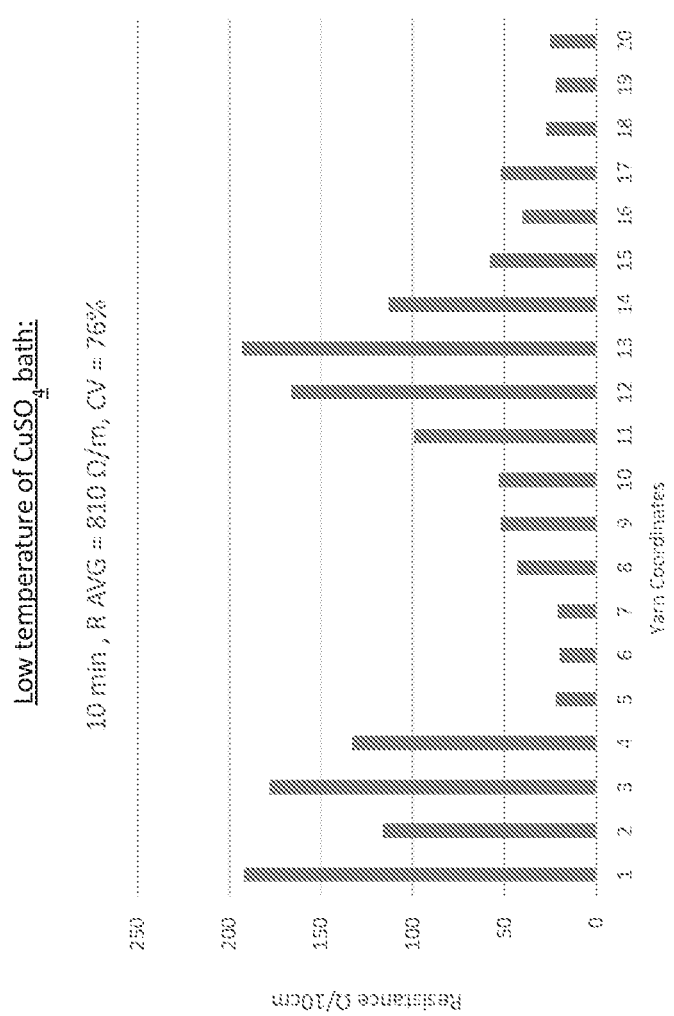
FIGS. 5A-5C are charts depicting electrical resistance as a function of yard length for low temperature Cu bath at various contact times.
Figure 5B:
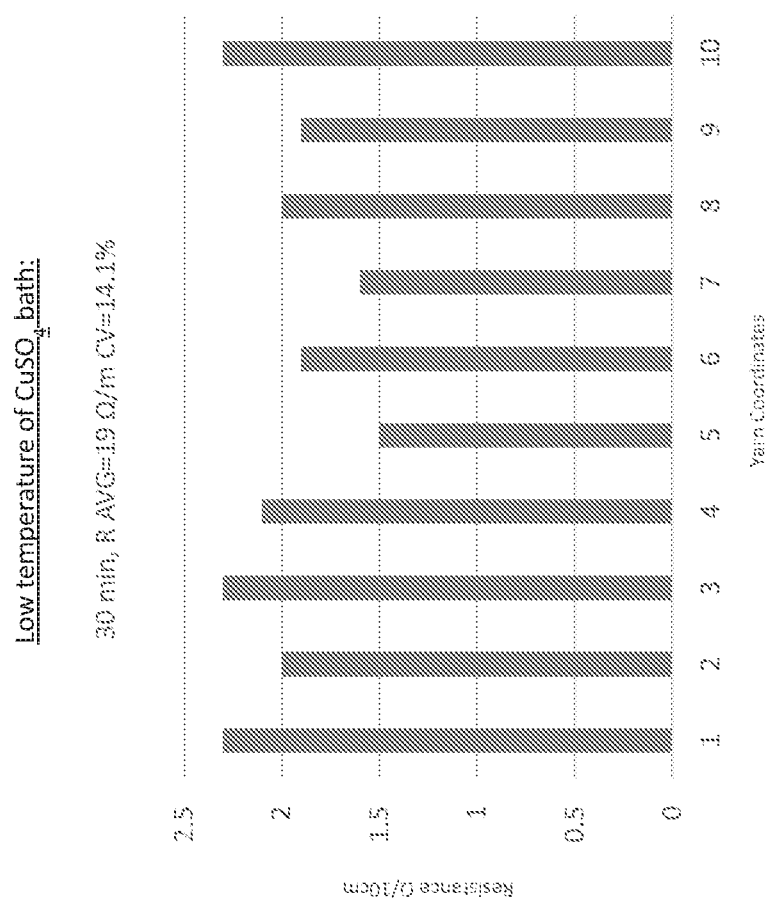
Figure 5C:
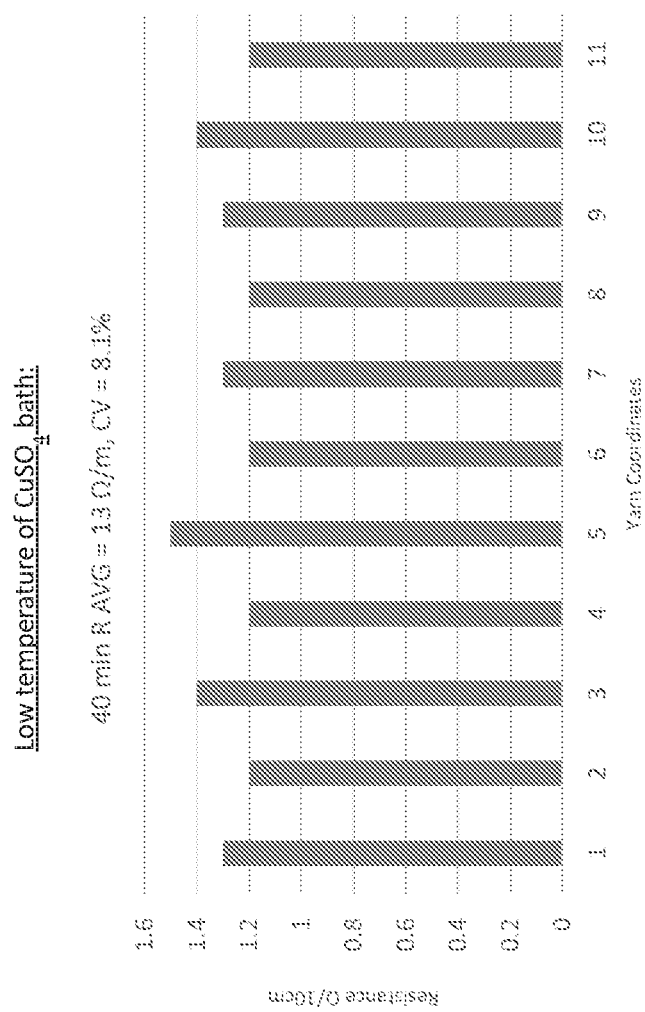

FIGS. 5A-5C depict the effect of temperature reduction from 45° C. to 25° C. of the $CuSO_4$ bath treatment time when coupled with a corresponding increase in treatment time.

Specifically, FIG. 5A depicts an average resistance of 810Ω for a 10 minute treatment time, whereas FIG. 5B depicts an average resistance of 19Ω for a 30 minute treatment time, and 5C depicts an average resistance of 13 for a 40 minute treatment. The conclusion being that lower temperature of $CuSO_4$ bath (25° C. instead 45° C.) coupled with longer treatment time improves the uniformity up to Coefficient of Variation (CV) of 8%.

Figure 6A:
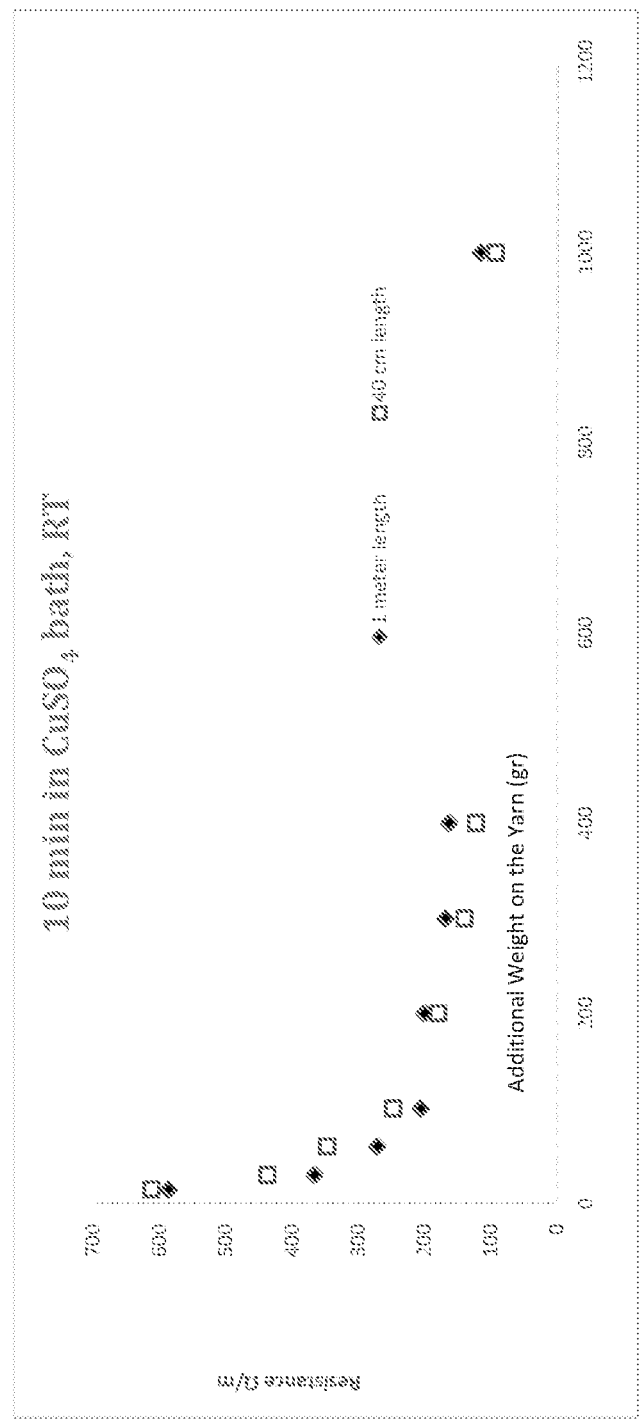
FIGS. 6A-6B are charts depicting electrical resistance as a function of weight applied to $CuSO_4$ treated yarn for 10 and 40 minutes, respectively.
Figure 6B:
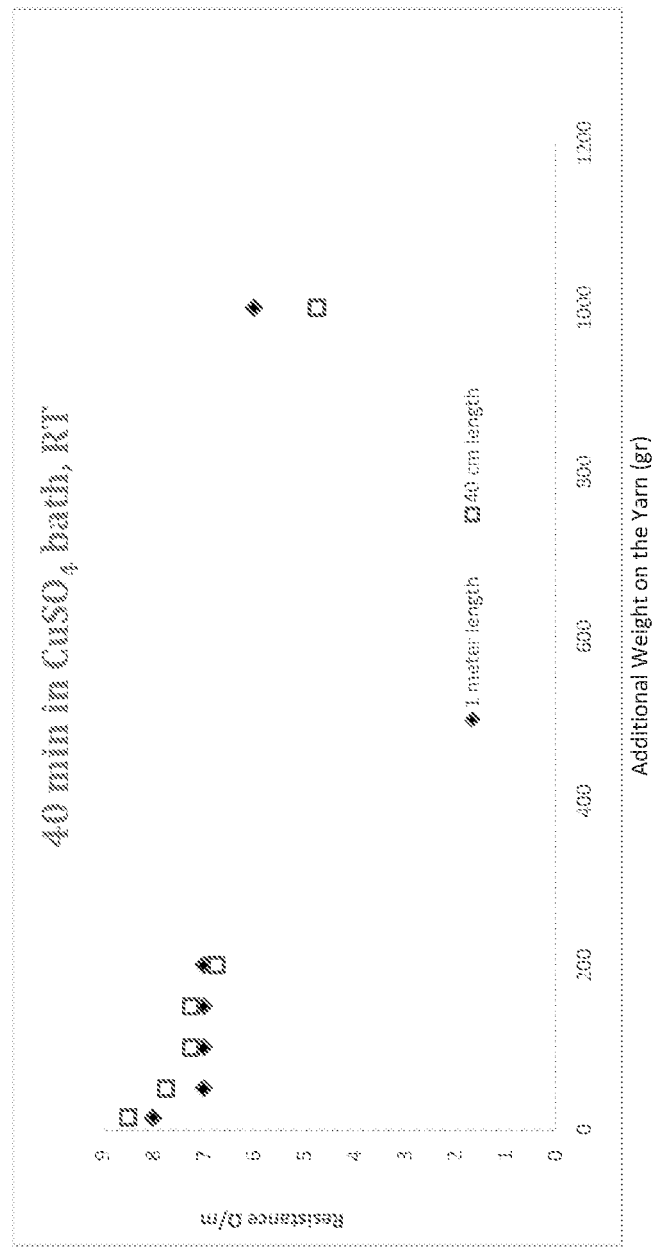

FIGS. 6A-6B are plots depicting current resistance for various PET yarn segments as a function of tension. The tests were performed for coated dtex 1100×3 polyester yarn with high twist with the following coatings:

PEI ($1^{st}$ and $2^{nd}$ layer 0.14 g/Kg, $3^{rd}$ layer 0.28 g/Kg, layer 0.28 g/Kg),
Pd 1 mM (10 mole/Kg),
Reduction (5 mM of Boron reagent) followed with three short washes 3 layers of CB (1$^{st}$ layer 0.5 g/Kg, 2$^{nd}$ layer 0.7 g/Kg, 3$^{rd}$ layer 1.0 g/Kg) applied in an Ugolini dying machine.

Specifically, FIG. 6A depicts resistance response for yarns treated in a Cu bath for only 10 minutes whereas FIG. 6B depicts the resistance response for yarns treated for 40 minutes.

It was found that points of discontinuity of the copper coating increases electrical resistance. Tension applied on yarn compresses the filaments together and improves contact between the fibers thereby improving conductivity. Accordingly, it was found that increasing tension applied to high resistance yarn dramatically reduces resistance. However, conductivity of low resistance yarn did no significantly improve upon application of tension. Yarn with high level of twist also demonstrated an ability to reduce resistance emanating from discontinuities in the copper coating for the reason noted above.

Fabrics

Figure 7A:
FIG. 7A is an image of yarn bobbins after various treatments.
Figure 7D:
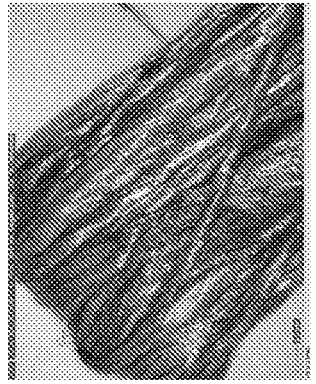
FIGS. 7B-7E are enlarged images of the yarn units of the fully Cu treated bobbin of variety of treatments.
Figure 7C:

Several fabric types such as treated Polyethylene terephthalate (PET) fabrics and SP1/CNT treated Fiber Glass fabrics which were prepared in house involved to the FIG. 7A is an image of three bobbins of PET yarn at various stages of treatment. The left bobbin is a nude bobbin with neither SP1/CB nor Pd treatments, whereas the middle bobbin has undergone full treatment; i.e. SP1/CB, Pd, and Cu treatments, and the right bobbin underwent SP1/CB and Cu treatments without a Pd treatment. (All treatments were implemented with an Ugolini dye machine.) It should be appreciated that SP1/CNT coatings in place of SP1/CB will also provide the necessary pre-Pd and Cu treatments.

Experimentation was performed to establish the necessity of each of the SP1/CB, PEI, and Pd treatments to achieved low resistance, uniform copper coating when applied to a Cu bath. After KTS scouring and smart winding of 1100×2 dtex polyester yarns, a first experiment lacking SP1/CB and Pd treatments, did not yield a Cu coating when a Cu bath was applied to the yarn. A second experiment performed with SP1/CB treated yarns; but, without Pd and Redox layers, also did not yield a Cu coating when a Cu bath was applied. A third experiment in which the yarn was subject both SP1/CB and Pd treatments yielded suitable for Cu coating when treated with a Cu bath.

Following is test data indicating the necessity of SP1/CNP and PEI, and Pd treatments as prerequisite treatments for a successive Cu treatment providing a uniform low resistant conductive coating.

| Yarn type | PET 1100x2 dtex, untreated yarn | PET 1100x2 dtex, treated with SP1/CB + PEI | PET 1100x2 dtex, treated with SP1/CB + PEI and NaPdCl$_4$ |
|---|---|---|---|
| CB and PEI treatment | No | 2 layers of CB, PEI | 2 layers of CB, PEI |
| NaPdCl$_4$ and reduction treatment in Ugolini | No | No | 1 mM NaPdCl$_4$ - 30 min, reduction - 30 min |
| CuSO$_4$ treatment in Ugolini | 30 min, 3 repeats | 30 min, 3 repeats | 30 min, 3 repeats |
| Ω/m Resistance | R > 2 * 10$^8$ | R > 2 * 10$^8$ | R = 10$^2$-10$^3$ |

In conclusion, an effective Cu coating is achievable only after SP1/CB, PEI, NaPdCl$_4$, treatments. In certain embodiments reduction treatment is also applied after the Pd treatment whereas in other embodiments this reduction treatment is not employed. The absence of any of these treatments will prevent the application of a low resistance, uniform copper coating.

FIGS. 7B-7E are enlarged views of the fibers of the properly Cu coated yarn the middle bobbin of FIG. 7. Specifically, the 226 dtex yarn depicted in FIG. 7B exhibited a resistance of 150 Ω/m after a five minute Cu bath, whereas the 1100×2 dtex yarn depicted in FIG. 7C exhibited a resistance of R=400 Ω/m after a one minute Cu bath, and the 1100×2 dtex yarn of FIG. 7D exhibited a resistance of R=10 Ω/m after a five minute Cu bath.

Figure 7E:
Figure 7B:

FIG. 7E is an enlarged view of a 1100×2 dtex yarn coated in CuSO$_4$ bath yarn in having a resistance of 40 Ω/m achieved with a Cu coating thickness of 3.5 in some areas and 3.2 micron in other areas when measured by X-RAY XDL-B instrument "Fischerscope". Dark areas have a measured thickness of 1.78 micron.

Figure 8:
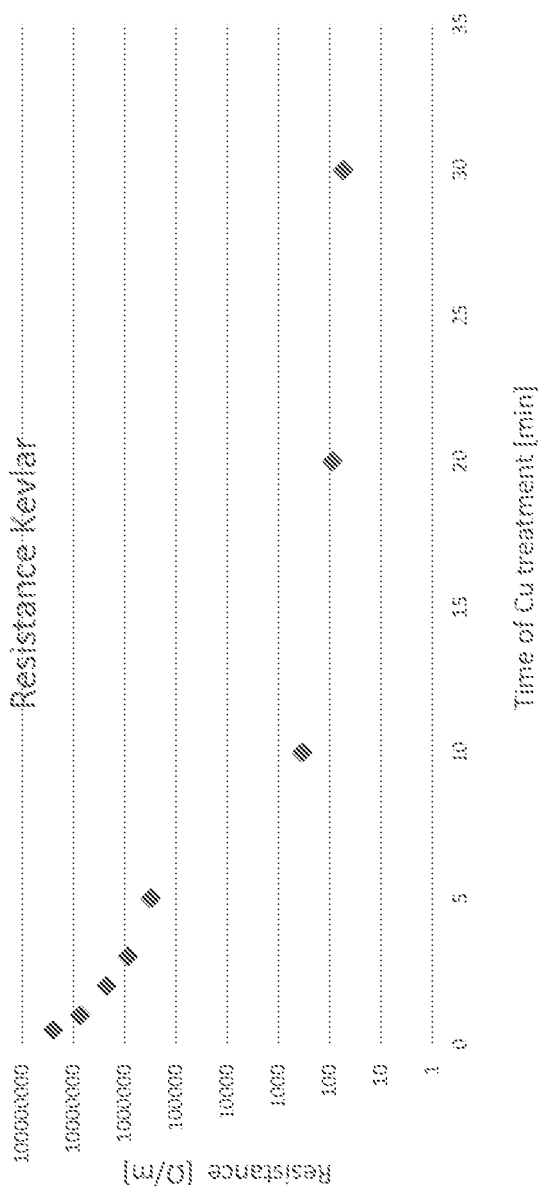
FIG. 8 is a plot depicting electrical resistance as a function of treatment time in a Cu bath for KEVLAR™ yarn.

FIG. 8 is a plot depicting resistance/length of KEVLAR™ yarns as a function of treatment time in a Cu bath. This experimentation was performed using 1100×4 dtex yarns with 3 layers of SP1/CB complex and PEI prior to treatment in an CU bath as described above. KEVLAR™ yarns exhibited high conductivity. Measurements of resistance were performed without the addition of weight.

Similar experimentation was performed for polyester fabrics. Conductivity was found to be strongly depended on NaPdCl4 concentration, CuSO$_4$ treatment time and addition of a competing agent.

Figure 9A:
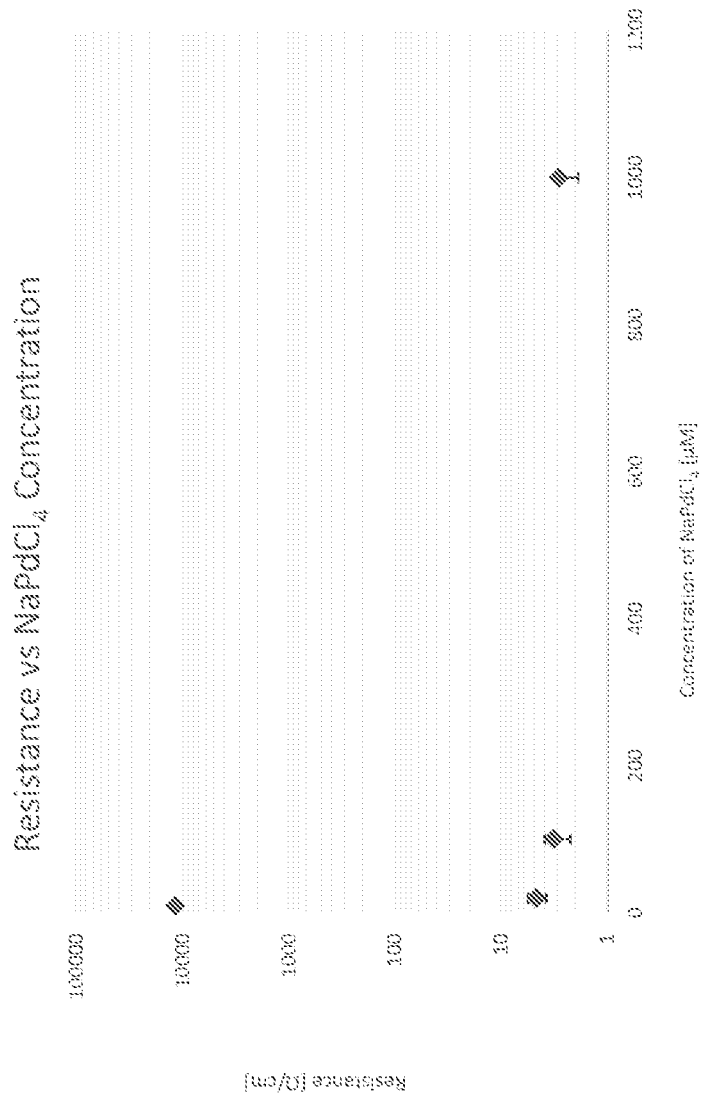
FIG. 9A is a plot depicting electrical resistance as a function of treatment time in a Cu bath for polyester fabric.

FIG. 9A is a plot depicting resistance/length of conductive polyester fabrics as a function of treatment time in a NaPdCl$_4$ bath. Surprisingly, it was found that decreasing the NaPdCl$_4$ concentration from 1 mM to 2 μM increased the resistance as depicted.

Figure 9B:
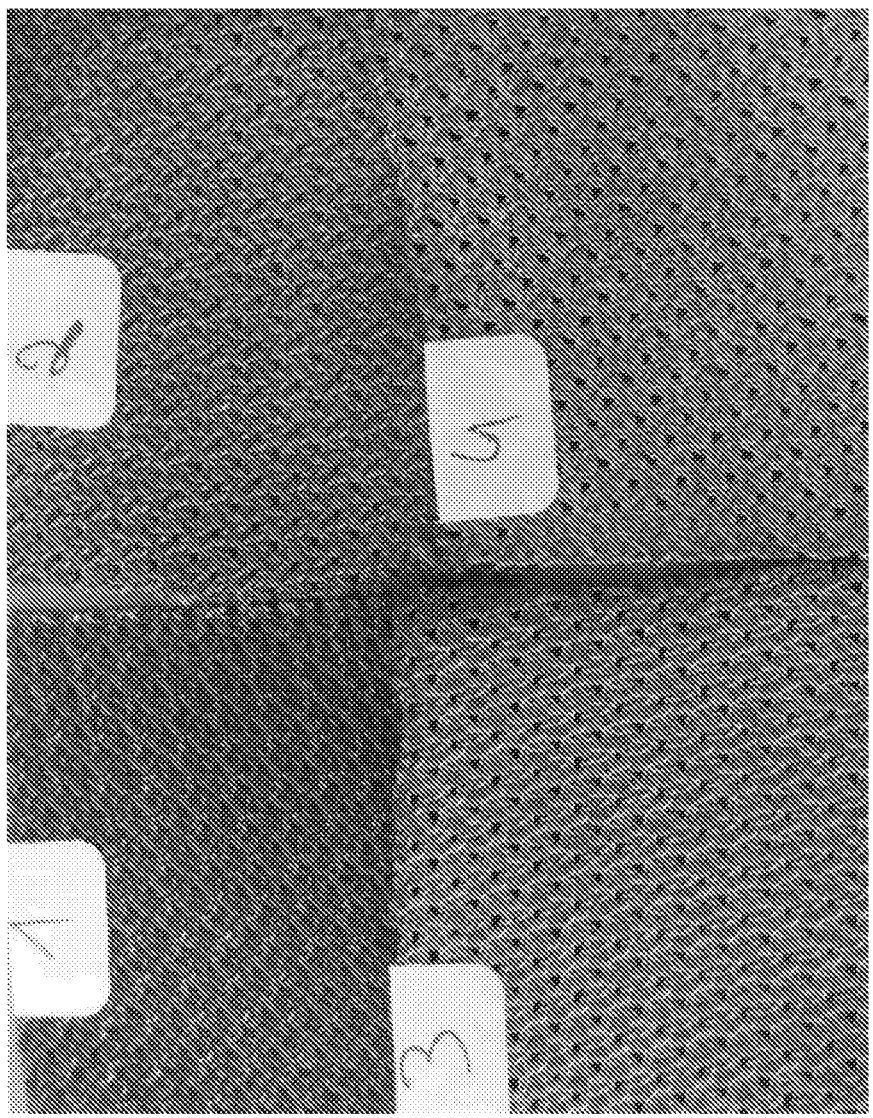
FIG. 9B is an image of conductive polyester fabric treated with different palladium concentrations.

FIG. 9B is a picture of several fabric samples after various stages of treatment from samples 1 to sample 4 having a complete copper coating.

Experimentation was also performed for glass fiber fabrics in which two layers of SP1/CNT were deposited on the glass fabric, treated with PEI followed by a NaPdCl$_4$ bath following by reduction and washes. Cu coating performed in bath at different time periods ranging from 3 minutes to 10 minutes. Additionally the experimentation of fabrics without the PEI treatment were also performed.

Figure 10A:
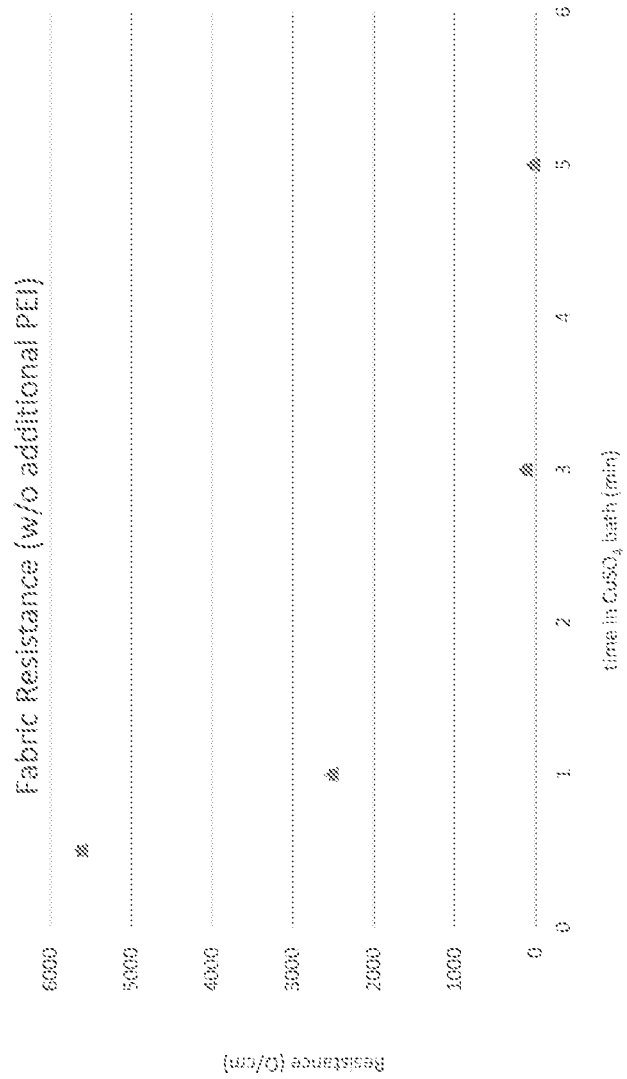
FIG. 10A is a plot depicting electrical resistance per length unit as a function of treatment time in a Cu bath for glass fiber fabric.

FIG. 10A is a plot depicting resistance/length of conductive glass fiber fabric as a function of treatment time in a CuSO$_4$ bath.

Figure 10C:
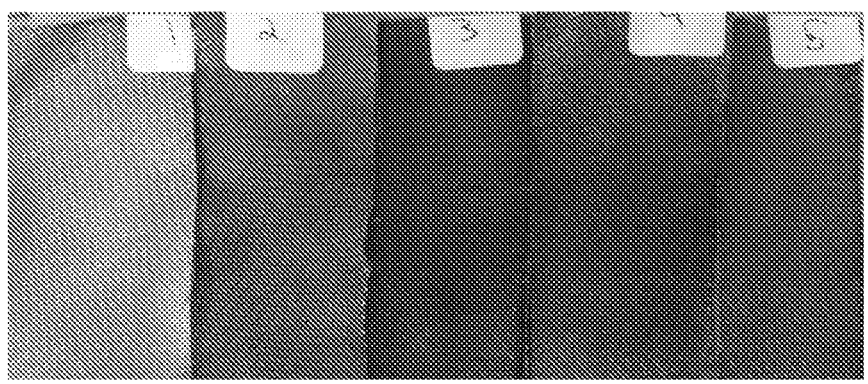
FIGS. 10B-10C are images of glass fiber fabric after various stages of treatment of in the absence of PEI treatment and in presence of PEI treatment, respectively.
Figure 10B:
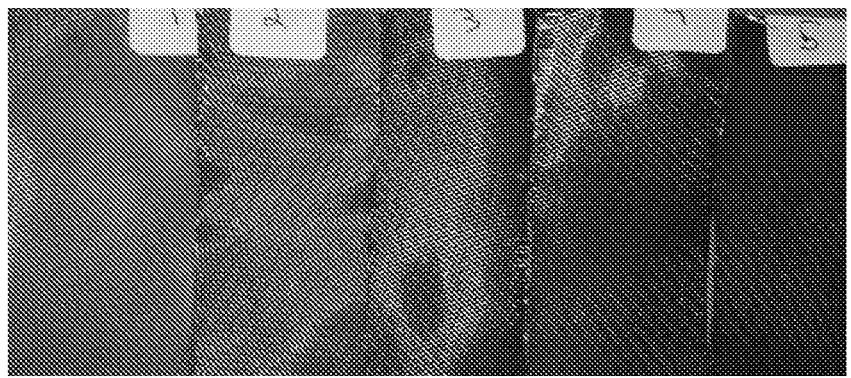

FIGS. 10B and 10C are images of samples after different treatment stages for operations including PEI treatment and without PEI treatment; respectively. As noted above, the presence of the rust or copper color is characteristic of the presence of the copper coating. As shown in the contrast in color of sample of each of the experiments, the lighter rust color in FIGS. 10B and 10C is characteristic of a more complete and copper deposition.

Conductive Carbon Black (CB$_{max}$)

As noted above, dispersion of conductive carbon black (CB$_{max}$) was investigated. It was found that PET yarn loaded with a nanometric dispersion of SP1/CB$_{max}$ complex yielded uniform and conductive coating even in the absence of electroless copper electroless coating.

Furthermore, it was found that copper electroless deposition on yarn loaded with SP1/CB$_{max}$ complex facilitated higher coating uniformity of copper coating reduced resistance than that of yarn loaded with non-conductive CB.

During investigation, a nanometric dispersion of conductive SP1/CB$_{max}$ complex was produced from CB$_{max}$ obtained from Cabot Corporation (available at 2 Seaport Ln #1300, Boston, Mass.) through the procedure described above.

Two parameters were tested; the quantity of SP1/CB$_{max}$ deposition and the thickness of the yarn. Three grades of yarn were investigated; thick yarn having a dtex of 1100×3, medium yarn having a 1100×2 dtex, and thin yarn having a dtex of 1100×1.

Each yarn grade was treated with several layers of SP1/CB$_{max}$ dispersion. The final results are summarized in the below table.

| Resistance for SP1/CB$_{max}$ Complex Without Copper Coating | | | | | | |
|---|---|---|---|---|---|---|
| | 1 CB$_{max}$ layer | | 2 CB$_{max}$ layers | | 3 CB$_{max}$ layers | |
| dtex | R (MΩ/m) | % CV | R (MΩ/m) | % CV | R (MΩ/m) | % CV |
| 1100×1 | >200 | — | >200 | — | 181 | 26% |
| 1100×2 | 99 | 7.3% | 21.7 | 10.1% | 16.5 | 8.8% |
| 1100×3 | — | — | 10.6 | 11.6% | 9.5 | 7.0% |

Initial results indicate that the coating levels of thin yarns (1100×1) were too low as may be seen by the high resistance. However medium and thick yarns (1100×2 and 1100×3) showed significantly lower resistance and a very low % CV. This is especially significant when contrasted with the high resistance (R>2*10$^8$ Ohm/m) measured in yarns loaded with nonconductive CB/SP complex.

The added coating uniformity and resulting resistivity reduction achieved through SP1/CB$_{max}$ complexes is crucial in the achievement of high conductivity using copper electroless coating yarns and fabrics.

Additionally, various yarn grades loaded with SP1/CB$_{max}$ complex were electrolessly copper coated.

Standard copper solutions were obtained from Amza Ltd. (Available at 37 Nachshon St. Industrial Area Sgula, Petach Tikva, Israel).

The active solution included three ingredients; sulfuric acid copper (2+) pentahydrate (10-25%), ethylene-dinitro-tetrapropan-2-ol (3-5%), methanol (1-2%), ethylene-dinitro-tetrapropan-2-ol (25-50%), and sodium hydroxide (25-50%). These ingredients were mixed before using in a standard ratio: A (60 mL), B (60 mL) and C (25 mL) for 1 L solution.

Multiple short coating steps of about ten minutes each with diluted copper solution prevented material waste and also facilitated uniform coating.

The copper was deposited on yarns coated with nonconductive SP1/CB complex using a batch dying machine as described above and it was found that yarn crossover occurring when wound around the bobbin prevented completely uniform coatings.

Surprisingly, the SP1/CB$_{max}$ complex facilitated a higher copper coating uniformity; thereby further reducing resistance, even in the presence of yarn crossover.

The resulting resistance measurements and associated coefficient of variation are set forth in the table below.

| Resistance for SP1/CB$_{max}$ Complex With Copper Coating | | | | | |
|---|---|---|---|---|---|
| | | Before Cu treatment | | After 3 layers of Cu | |
| dtex | CB layers | R (MΩ/m) | Uniformity % CV | R (MΩ/m) | Uniformity % CV |
| 1100×2 | 3 | 16.5 | 8.8% | 1.2 | 11.1% |
| 1100×3 | 2 | 10.6 | 11.6% | 3.6 | 12.7% |

As shown in this table, SP1/CB$_{max}$ complex is a highly effective platform for achieving uniformly conductive yarn or fabrics even after application of metallic coatings.

Polymeric Protection

Low resistance yarn or fabric of about 10-1,000 Ω/m is achieved through though the depositing of several layers of copper through 10-18 treatments of diluted copper solution, according to a certain embodiment. The yarns and fabrics are susceptible to detachment of the copper coating from the fiber through mechanical abrasion.

Accordingly, polymeric coating, like polyurethane for example, was applied after copper deposition and washing. As expected, resistance was increased; however, the benefit of the added durability offset the increase in resistivity.

It should be appreciated that in a certain embodiment FeCl$_3$ is used a conductive agent. Advantages of us using FeCl3 as a conductive agent is that it is more inexpensive than Pd and Cu, only one treatment is required, a variety of polymers are suitable for FeCl3 attraction, and also leads to leads to lower conductivity as required in certain applications.

In another embodiment, aluminum is employed with suitable polymeric substrates like polypyrrole or polyaniline.

In another embodiment, nickel with suitable polymeric substrates like polypyrrole or polyaniline.

In another embodiment, cobalt with suitable polymeric substrates like polypyrrole or polyaniline.

In another embodiment, gold metals with suitable polymeric substrates like polypyrrole or polyaniline.

In a certain embodiment the carbon particles are implemented as micro-particles instead of nanoparticles.

Although the invention has been described in conjunction with specific embodiments thereof, it is evident that many alternatives, modifications and variations will be apparent to those skilled in the art.

In certain embodiments, the outer coating is constructed from silver, other embodiments employ platinum and other embodiments employ Rhodium or Iridium. In certain embodiments a different metals are employed in separate coatings whereas in certain other embodiments identical metals are implemented as separate coatings. In other embodiments the coatings are implemented as metal alloys.

In some embodiments the thickness of the outer metal coating is implemented between 0.1 μm and 10.0 μm whereas in other embodiments the thickness of between 0.01 μm and 100.0 μm.

A certain embodiment uses a twist level of either fibers or yarn as low as 20 twists/meter whereas different embodiments use twist levels of over 100 twist/meter. It should be appreciated that other twist levels are included in the scope of the invention.

Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A conductive yarn comprising:
 a plurality of interlocked fibers at least partially coated with a composition of carbon black (CB) and SP1 variant (SP1/CB);

one or more polyamine coating(s); and an outer metal coating.

2. The conductive yarn of claim 1, wherein the polyamine coatings are a first polyamine coating sandwiched between the fiber and the composition and a second polyamine coating between the composition and the outer metal coating.

3. The conductive yarn of claim 1, further comprising an inner metal coating disposed between the second polyamine coating and the outer metal coating.

4. The conductive yarn of claim 1, wherein said SP1 variant is non-covalently bound to the carbon black.

5. The conductive yarn of claim 1, wherein said SP1 variant has the amino acid sequence of SEQ ID NOs: 3, 4, 6, 8, 9, 14-18 or 86; wherein the carbon black is selected from the group consisting of conductive carbon black and non-conductive carbon black;

wherein the outer metal coating is a copper coating; wherein the inner metal coating is Pd(II), Pt(II), Rh(I), Ir(I), iron, aluminum, gold, silver, nickel, or combination thereof; wherein the fiber is selected from the group consisting of cotton fiber, wool fiber, silk fiber, glass fiber, nylon fiber, polyester fiber, aramid fiber, polyethylene fiber, poly-olefin fiber, polypropylene fiber, and elastane fiber; wherein the load of said SP1/CB on said yarn is between 0.01 gr/kg and 100 gr/kg; wherein said CB:SP1 ratio is between 0.1:1 to 30:1 dry w/w; wherein the yarn has a twist range of at least 10 winds/meter; wherein the outer metal coating has a thickness of between 0.01 μm and 100.0 μm; wherein said yarn has a resistance between 0.001 Ω/m to 1000 mega Ω/m; wherein said polyamine includes polyethyleneimine (PEI);

wherein the yarn further comprises a polymeric coating on the outer metal coating; or any combination thereof.

6. The conductive yarn of claim 5, wherein the load of said SP1/CB on said yarn is between 5 gr/kg and 15 gr/kg; said CB:SP1 ratio is between 2.5:1 to 8:1 dry w/w; or combination thereof.

7. The conductive yarn of claim 1, wherein the inner metal coating is Pd(II), Pt(II), Rh(I), Ir(I), iron, aluminum, gold, silver, nickel, or combination thereof.

8. A conductive yarn comprising:
a plurality of interlocked fibers at least partially coated with a composition of conductive carbon black ($CB_{max}$) and SP1 variant ($SP1/CB_{max}$);

one or more polyamine coating(s); and an outer metal coating.

9. The conductive yarn of claim 8, further comprising a polymeric coating on the outer metal coating; wherein the polyamine coatings are implemented as a first polyamine coating sandwiched between the fiber and the composition of the $SP1/CB_{max}$ and a second polyamine coating between the composition and the outer metal coating; or combination thereof.

10. A conductive film comprising:
a polymeric film coated at least partially coated with a composition of carbon black (CB) and SP1 variant (SP1/CB);

a plurality of polyamine coatings; and an outer metal coating disposed on the polyamines coating.

11. The conductive film of claim 10, wherein the polyamine coatings are a first polyamine coating sandwiched between the film and the composition and a second polyamine coating between the composition and the outer metal coating.

12. The conductive film of claim 10, wherein the inner metal coating is disposed between the second polyamine coating and the outer metal coating.

13. The conductive film of claim 10, wherein the CB includes conductive $CB_{max}$.

14. A method of producing the conductive yarn of claim 1, comprising:

contacting a plurality of fibers with a polyamine so as to form a plurality of polyamine coated fibers;

contacting the polyamine coated fibers with a dispersion comprising an SP1/CB complex so as to form a plurality of complex coated fibers; and contacting the plurality of complex coated fibers with a metallic catalyst so as to form a metallic catalyst coating on the plurality of fibers.

15. The method of claim 14, further comprising at least one step of washing said yarn with a buffer or water after each step of the method; wherein the contacting the plurality of complex coated fibers with a metallic catalyst is implemented in a textile dying machine or a bath; wherein said dispersion comprises an SP1/CB composition in a concentration of between 0.01% and 50% w/w; wherein said dispersion comprises an SP1/CB composition is in a concentration of 2%, 4%, 6%, or 8% w/w; wherein said PEI is applied to the yarn at a load of 0.0035% to 30.0% w/w; wherein said method is performed at temperature between 4°-90° C.; wherein the metallic catalyst is iron, gold, silver, nickel, platinum, aluminum, or any combination thereof; wherein the metallic catalyst is implemented as Pd(II), Pt(II), Rh(I), Ir(I), Cu(II) or any combination thereof; wherein the method further comprises applying an outer metallic coating of copper outside of the metallic catalyst coating the fibers; wherein the method further comprises drying the fibers after contacting the metal catalyst; wherein the CB of the SP1/CB complex is implemented as conductive carbon black ($CB_{max}$); or any combination thereof.

16. The method of claim 15, wherein said dispersion comprises an SP1/CB composition is in a concentration of 0.05%, 0.1%, between 0.05% and 0.15%, or between 1% and 20% w/w; wherein said PEI is applied to the yarn at a load of 0.007% to 0.7% w/w; wherein the metallic catalyst is a combination of Pd(II) and Cu(II); wherein the contacting the plurality of fibers with a metallic catalyst is implemented in a time span ranging from 5 seconds to 1 hour; wherein the method further comprises reducing the metallic catalyst to the metallic state; wherein the method further comprises applying a polymeric coating onto the outer metallic coating of copper; or any combination thereof.

17. The method of claim 16, wherein the ratio between Pd(II) and Cu(II) is 1:10.

* * * * *

SEQUENCE LISTING

```
<160> NUMBER OF SEQ ID NOS: 89

<210> SEQ ID NO 1
<211> LENGTH: 103
<212> TYPE: PRT
<213> ORGANISM: Artificial sequence
<220> FEATURE:
<223> OTHER INFORMATION: Sp1 mutant variant: amino acid 2-6 deleted,
      M43C mutated

<400> SEQUENCE: 1

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
                20                  25                  30

Asp Leu Ile Pro Ser Cys Lys Ser Phe Asn Trp Gly Thr Asp Leu Gly
            35                  40                  45

Met Glu Ser Ala Glu Leu Asn Arg Gly Tyr Thr His Ala Phe Glu Ser
        50                  55                  60

Thr Phe Glu Ser Lys Ser Gly Leu Gln Glu Tyr Leu Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 2
<211> LENGTH: 103
<212> TYPE: PRT
<213> ORGANISM: Artificial sequence
<220> FEATURE:
<223> OTHER INFORMATION: Sp1 mutant variant: amino acid 2-6 deleted,
      L81C mutated

<400> SEQUENCE: 2

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
                20                  25                  30

Asp Leu Ile Pro Ser Met Lys Ser Phe Asn Trp Gly Thr Asp Leu Gly
            35                  40                  45

Met Glu Ser Ala Glu Leu Asn Arg Gly Tyr Thr His Ala Phe Glu Ser
        50                  55                  60
```

```
Thr Phe Glu Ser Lys Ser Gly Leu Gln Glu Tyr Cys Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 3
<211> LENGTH: 114
<212> TYPE: PRT
<213> ORGANISM: Artificial sequence
<220> FEATURE:
<223> OTHER INFORMATION: mTB peptide fused to N' of Sp1 (2-6 deleted and
      M43C mutated)

<400> SEQUENCE: 3

Met Arg Lys Leu Pro Asp Ala Ala Thr Arg Thr Pro Lys Leu Val Lys
1               5                   10                  15

His Thr Leu Leu Thr Arg Phe Lys Asp Glu Ile Thr Arg Glu Gln Ile
            20                  25                  30

Asp Asn Tyr Ile Asn Asp Tyr Thr Asn Leu Leu Asp Leu Ile Pro Ser
        35                  40                  45

Met Lys Ser Phe Asn Trp Gly Thr Asp Leu Gly Met Glu Ser Ala Glu
    50                  55                  60

Leu Asn Arg Gly Tyr Thr His Ala Phe Glu Ser Thr Phe Glu Ser Lys
65                  70                  75                  80

Ser Gly Leu Gln Glu Tyr Leu Asp Ser Ala Ala Leu Ala Ala Phe Ala
                85                  90                  95

Glu Gly Phe Leu Pro Thr Leu Ser Gln Arg Leu Val Ile Asp Tyr Phe
            100                 105                 110

Leu Tyr

<210> SEQ ID NO 4
<211> LENGTH: 108
<212> TYPE: PRT
<213> ORGANISM: Populus tremula
<220> FEATURE:
<221> NAME/KEY: misc_feature
<223> OTHER INFORMATION: Wild type Sp1 polypeptide

<400> SEQUENCE: 4

Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 5
<211> LENGTH: 6
<212> TYPE: PRT
```

<213> ORGANISM: Artificial sequence
<220> FEATURE:
<223> OTHER INFORMATION: mTBP peptide

<400> SEQUENCE: 5

Arg Lys Leu Pro Asp Ala
1               5

<210> SEQ ID NO 6
<211> LENGTH: 120
<212> TYPE: PRT
<213> ORGANISM: Artificial sequence
<220> FEATURE:
<223> OTHER INFORMATION: L1-Sp1 fusion polypeptide

<400> SEQUENCE: 6

Met His Trp Ser Ala Trp Trp Ile Arg Ser Asn Gln Ser Ala Thr Arg
1               5                   10                  15

Thr Pro Lys Leu Val Lys His Thr Leu Leu Thr Arg Phe Lys Asp Glu
            20                  25                  30

Ile Thr Arg Glu Gln Ile Asp Asn Tyr Ile Asn Asp Tyr Thr Asn Leu
        35                  40                  45

Leu Asp Leu Ile Pro Ser Met Lys Ser Phe Asn Trp Gly Thr Asp Leu
    50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
        115                 120

<210> SEQ ID NO 7
<211> LENGTH: 333
<212> TYPE: DNA
<213> ORGANISM: Artificial sequence
<220> FEATURE:
<223> OTHER INFORMATION: Delta N' SP1 coding sequence

<400> SEQUENCE: 7
ccacagagag aaagggaaga catgaagctt gtgaagcaca cattgttgac tcggttcaag     60
gatgagatca cacgagaaca gatcgacaac tacattaatg actataccaa tctgctcgat    120
ctcattccaa gcatgaagag tttcaattgg ggcacggatc tgggcatgga gtctgcggag    180
ctaaaccgag atacactca tgcctttgaa tctacatttg agagcaagtc tggtttgcaa     240
gagtacctcg attctgctgc tcttgctgca tttgcagaag gttttttgcc tactttgtca    300
cagcgtcttg tgatagacta ctttctctac taa                                 333

<210> SEQ ID NO 8
<211> LENGTH: 120
<212> TYPE: PRT
<213> ORGANISM: Artificial sequence
<220> FEATURE:
<223> OTHER INFORMATION: L3-Sp1 fusion polypeptide

<400> SEQUENCE: 8

Met Asp Tyr Phe Ser Ser Pro Tyr Tyr Glu Gln Leu Phe Ala Thr Arg
1               5                   10                  15

Thr Pro Lys Leu Val Lys His Thr Leu Leu Thr Arg Phe Lys Asp Glu

```
                    20                  25                  30
Ile Thr Arg Glu Gln Ile Asp Asn Tyr Ile Asn Asp Tyr Thr Asn Leu
                35                  40                  45

Leu Asp Leu Ile Pro Ser Met Lys Ser Phe Asn Trp Gly Thr Asp Leu
50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
                100                 105                 110

Leu Val Ile Asp Tyr Phe Leu Tyr
                115                 120

<210> SEQ ID NO 9
<211> LENGTH: 120
<212> TYPE: PRT
<213> ORGANISM: Artificial sequence
<220> FEATURE:
<223> OTHER INFORMATION: L4-Sp1 fusion polypeptide

<400> SEQUENCE: 9

Met His Trp Ser Ala Trp Trp Ile Arg Ser Asn Gln Ser Ala Thr Arg
1               5                   10                  15

Thr Pro Lys Leu Val Lys His Thr Leu Thr Arg Phe Lys Asp Glu
                20                  25                  30

Ile Thr Lys Glu Gln Ile Asp Asn Tyr Ile Asn Asp Tyr Thr Asn Leu
                35                  40                  45

Leu Asp Leu Ile Pro Ser Met Lys Ser Phe Asn Trp Gly Thr Asp Leu
50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
                100                 105                 110

Leu Val Ile Asp Tyr Phe Leu Tyr
                115                 120

<210> SEQ ID NO 10
<211> LENGTH: 12
<212> TYPE: PRT
<213> ORGANISM: Artificial sequence
<220> FEATURE:
<223> OTHER INFORMATION: L1 peptide

<400> SEQUENCE: 10

His Trp Ser Ala Trp Trp Ile Arg Ser Asn Gln Ser
1               5                   10

<210> SEQ ID NO 11
<211> LENGTH: 12
<212> TYPE: PRT
<213> ORGANISM: Artificial sequence
<220> FEATURE:
<223> OTHER INFORMATION: L2 peptide

<400> SEQUENCE: 11

His Ser Ser Tyr Trp Tyr Ala Phe Asn Asn Lys Thr
1               5                   10
```

<210> SEQ ID NO 12
<211> LENGTH: 12
<212> TYPE: PRT
<213> ORGANISM: Artificial sequence
<220> FEATURE:
<223> OTHER INFORMATION: L3 peptide

<400> SEQUENCE: 12

Asp Tyr Phe Ser Ser Pro Tyr Tyr Glu Gln Leu Phe
1               5                   10

<210> SEQ ID NO 13
<211> LENGTH: 4
<212> TYPE: PRT
<213> ORGANISM: Artificial sequence
<220> FEATURE:
<223> OTHER INFORMATION: L6 peptide

<400> SEQUENCE: 13

Ser Asn Gln Ser
1

<210> SEQ ID NO 14
<211> LENGTH: 120
<212> TYPE: PRT
<213> ORGANISM: Artificial sequence
<220> FEATURE:
<223> OTHER INFORMATION: L2-Sp1 fusion polypeptde

<400> SEQUENCE: 14

Met His Ser Ser Tyr Trp Tyr Ala Phe Asn Asn Lys Thr Ala Thr Arg
1               5                   10                  15

Thr Pro Lys Leu Val Lys His Thr Leu Leu Thr Arg Phe Lys Asp Glu
            20                  25                  30

Ile Thr Arg Glu Gln Ile Asp Asn Tyr Ile Asn Asp Tyr Thr Asn Leu
        35                  40                  45

Leu Asp Leu Ile Pro Ser Met Lys Ser Phe Asn Trp Gly Thr Asp Leu
    50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
            115                 120

<210> SEQ ID NO 15
<211> LENGTH: 112
<212> TYPE: PRT
<213> ORGANISM: Artificial sequence
<220> FEATURE:
<223> OTHER INFORMATION: L6-Sp1 fusion polypeptide

<400> SEQUENCE: 15

Met Ser Asn Gln Ser Ala Thr Arg Thr Pro Lys Leu Val Lys His Thr
1               5                   10                  15

Leu Leu Thr Arg Phe Lys Asp Glu Ile Thr Arg Glu Gln Ile Asp Asn
            20                  25                  30

Tyr Ile Asn Asp Tyr Thr Asn Leu Leu Asp Leu Ile Pro Ser Met Lys
        35                  40                  45

```
Ser Phe Asn Trp Gly Thr Asp Leu Gly Met Glu Ser Ala Glu Leu Asn
        50                  55                  60

Arg Gly Tyr Thr His Ala Phe Glu Ser Thr Phe Glu Ser Lys Ser Gly
 65                  70                  75                  80

Leu Gln Glu Tyr Leu Asp Ser Ala Ala Leu Ala Ala Phe Ala Glu Gly
                85                  90                  95

Phe Leu Pro Thr Leu Ser Gln Arg Leu Val Ile Asp Tyr Phe Leu Tyr
                100                 105                 110

<210> SEQ ID NO 16
<211> LENGTH: 120
<212> TYPE: PRT
<213> ORGANISM: Artificial sequence
<220> FEATURE:
<223> OTHER INFORMATION: L7-Sp1 fusion polypeptide

<400> SEQUENCE: 16

Met His Trp Ser Ala Trp Trp Ile Arg Ser Asn Gln Ser Ala Thr Arg
 1               5                  10                  15

Thr Pro Lys Leu Val Lys His Thr Leu Leu Thr Arg Phe Lys Asp Glu
                20                  25                  30

Ile Thr Arg Glu Gln Ile Asp Asn Tyr Ile Asn Asp Tyr Thr Asn Leu
            35                  40                  45

Leu Asp Leu Ile Pro Ser Met Lys Ser Phe Asn Trp Gly Thr Asp Leu
        50                  55                  60

Gly Met Glu Ser Ala Glu Leu Asn Arg Gly Tyr Thr His Ala Phe Glu
 65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
                100                 105                 110

Leu Val Ile Asp Tyr Phe Leu Tyr
            115                 120

<210> SEQ ID NO 17
<211> LENGTH: 120
<212> TYPE: PRT
<213> ORGANISM: Artificial sequence
<220> FEATURE:
<223> OTHER INFORMATION: L5-Sp1 fusion polypeptide

<400> SEQUENCE: 17

Met His Trp Ser Ala Trp Trp Ile Arg Ser Asn Gln Ser Ala Thr Arg
 1               5                  10                  15

Thr Pro Lys Leu Val Lys His Thr Leu Leu Thr Arg Phe Lys Asp Glu
                20                  25                  30

Ile Cys Arg Glu Gln Ile Asp Asn Tyr Ile Asn Asp Tyr Thr Asn Leu
            35                  40                  45

Leu Asp Leu Ile Pro Ser Met Lys Ser Phe Asn Trp Gly Thr Asp Leu
        50                  55                  60

Gly Met Glu Ser Ala Glu Leu Asn Arg Gly Tyr Thr His Ala Phe Glu
 65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
                100                 105                 110

Leu Val Ile Asp Tyr Phe Leu Tyr
```

```
            115                 120

<210> SEQ ID NO 18
<211> LENGTH: 120
<212> TYPE: PRT
<213> ORGANISM: Artificial sequence
<220> FEATURE:
<223> OTHER INFORMATION: L8-Sp1 fusion polypeptide

<400> SEQUENCE: 18

Met His Trp Ser Ala Trp Trp Ile Arg Ser Asn Gln Ser Ala Thr Arg
1               5                   10                  15

Thr Pro Lys Leu Val Lys His Thr Leu Leu Thr Arg Phe Lys Asp Glu
            20                  25                  30

Ile Thr Lys Glu Gln Ile Asp Asn Tyr Ile Asn Asp Tyr Thr Asn Leu
        35                  40                  45

Leu Asp Leu Ile Pro Ser Met Lys Ser Phe Asn Trp Gly Thr Asp Leu
    50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
            115                 120

<210> SEQ ID NO 19
<211> LENGTH: 6
<212> TYPE: PRT
<213> ORGANISM: Artificial sequence
<220> FEATURE:
<223> OTHER INFORMATION: Exemplary heterologous titanium binding peptide

<400> SEQUENCE: 19

Arg Ala Leu Pro Asp Ala
1               5

<210> SEQ ID NO 20
<211> LENGTH: 10
<212> TYPE: PRT
<213> ORGANISM: Artificial sequence
<220> FEATURE:
<223> OTHER INFORMATION: Exemplary peptide that binds inorganic
      substances

<400> SEQUENCE: 20

Ala Lys Pro Ser Tyr Pro Pro Thr Tyr Lys
1               5                   10

<210> SEQ ID NO 21
<211> LENGTH: 6
<212> TYPE: PRT
<213> ORGANISM: Artificial sequence
<220> FEATURE:
<223> OTHER INFORMATION: Exemplary peptide that binds inorganic
      substances

<400> SEQUENCE: 21

Ala Lys Pro Thr Tyr Lys
1               5

<210> SEQ ID NO 22
```

```
<211> LENGTH: 10
<212> TYPE: PRT
<213> ORGANISM: Artificial sequence
<220> FEATURE:
<223> OTHER INFORMATION: Exemplary peptide that binds inorganic
      substances

<400> SEQUENCE: 22

Pro Lys Ile Ser Tyr Pro Pro Thr Tyr Lys
1               5                   10

<210> SEQ ID NO 23
<211> LENGTH: 10
<212> TYPE: PRT
<213> ORGANISM: Artificial sequence
<220> FEATURE:
<223> OTHER INFORMATION: Exemplary peptide that binds inorganic
      substances
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 23

Ala Pro Pro Pro Ala Xaa Thr Ala Xaa Lys
1               5                   10

<210> SEQ ID NO 24
<211> LENGTH: 10
<212> TYPE: PRT
<213> ORGANISM: Artificial sequence
<220> FEATURE:
<223> OTHER INFORMATION: Exemplary peptide that binds inorganic
      substances
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 24

Ala Thr Pro Lys Pro Xaa Thr Ala Xaa Lys
1               5                   10

<210> SEQ ID NO 25
<211> LENGTH: 4
<212> TYPE: PRT
<213> ORGANISM: Artificial sequence
<220> FEATURE:
<223> OTHER INFORMATION: Exemplary peptide that binds inorganic
      substances

<400> SEQUENCE: 25

Pro Tyr Val Lys
1

<210> SEQ ID NO 26
<211> LENGTH: 12
<212> TYPE: PRT
<213> ORGANISM: Artificial sequence
<220> FEATURE:
<223> OTHER INFORMATION: Exemplary peptide that binds inorganic
      substances
```

<400> SEQUENCE: 26

Ala Lys Pro Ser Pro Tyr Val Pro Thr Gly Tyr Lys
1               5                   10

<210> SEQ ID NO 27
<211> LENGTH: 13
<212> TYPE: PRT
<213> ORGANISM: Artificial sequence
<220> FEATURE:
<223> OTHER INFORMATION: Exemplary peptide that binds inorganic
      substances

<400> SEQUENCE: 27

Gly Gln Gln Lys Gln Thr Ala Tyr Asp Pro Gly Tyr Lys
1               5                   10

<210> SEQ ID NO 28
<211> LENGTH: 567
<212> TYPE: DNA
<213> ORGANISM: Populus tremula

<400> SEQUENCE: 28

```
atccacagag agaaagggaa gacatggcaa ccagaactcc aaagcttgtg aagcacacat        60
tgttgactcg gttcaaggat gagatcacac gagaacagat cgacaactac attaatgact       120
ataccaatct gctcgatctc attccaagca tgaagagttt caattggggc acggatctgg       180
gcatggagtc tgcggagcta aaccgaggat acactcatgc ctttgaatct acatttgaga       240
gcaagtctgg tttgcaagag tacctcgatt ctgctgctct tgctgcattt gcagaagggt       300
ttttgcctac tttgtcacag cgtcttgtga tagactactt tctctactaa acgctcagga       360
gtaacgactt cggccgggct atttcatggt aataaagtaa tgtaatgttc aataaatgct       420
ggttttgaac cactgaatgt tcgtgtcttg atttcttgtc tgtgctaagt gaagggagtg       480
ctgctattcc tttaaaaata aagcccttgg ggttgagttg tagttttca atcttttcc         540
ccgatttatt tcggtcttgg tgttgtt                                            567
```

<210> SEQ ID NO 29
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 29

Val Val Lys His Leu Val Ile Val Gln Phe Lys Glu Asp Val Thr Pro
1               5                   10                  15

Glu Arg Leu Asp Gly Leu Ile Arg Gly Tyr Ala Gly Leu Val Asp Lys
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 30
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 30

Val Val Lys His Leu Val Ile Val Gln Phe Lys Glu Asp Val Thr Pro
1               5                   10                  15

Glu Arg Leu Asp Gly Leu Ile Arg Gly Tyr Ala Gly Leu Val Asp Lys
                20                  25                  30

Val Pro Ser Met Lys Ala Phe His Trp Gly Thr Asp Val Ser Ile Glu
            35                  40                  45

Asn Xaa Xaa Met His Gln Gly Phe Thr His Val Phe Glu Ser Thr Phe
        50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 31
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 31

Val Val Lys His Leu Val Ile Val Gln Phe Lys Glu Asp Val Thr Pro
1               5                   10                  15

Glu Arg Leu Glu Gly Leu Ile Arg Gly Tyr Ala Gly Leu Val Asp Lys
                20                  25                  30

Val Pro Ser Met Lys Ala Phe His Trp Gly Thr Asp Val Ser Ile Glu
            35                  40                  45

Asn Xaa Xaa Met His Gln Gly Phe Thr His Val Phe Glu Ser Thr Phe
        50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 32
<211> LENGTH: 84
<212> TYPE: PRT
<213> ORGANISM: Zea mays
<220> FEATURE:
<221> NAME/KEY: misc_feature
<222> LOCATION: (50)..(51)
<223> OTHER INFORMATION: Xaa can be any naturally occurring amino acid

<400> SEQUENCE: 32

Val Val Lys His Ile Leu Leu Ala Ser Phe Lys Glu Glu Val Thr Gln
1               5                   10                  15

```
Glu Arg Leu Asp Glu Leu Ile Arg Gly Tyr Ala Ala Leu Val Gly Val
             20                  25                  30

Val Pro Ser Met Lys Ala Phe His Trp Gly Thr Asp Val Ser Ile Glu
         35                  40                  45

Asn Xaa Xaa Met His Gln Gly Phe Thr His Val Phe Glu Ser Thr Phe
     50                  55                  60

Glu Ser Thr Glu Gly Ile Lys Glu Tyr Ile Glu His Pro Ala His Val
 65                  70                  75                  80

Glu Phe Ala Lys
```

<210> SEQ ID NO 33
<211> LENGTH: 98
<212> TYPE: PRT
<213> ORGANISM: Oryza sativa
<220> FEATURE:
<221> NAME/KEY: misc_feature
<222> LOCATION: (50)..(51)
<223> OTHER INFORMATION: Xaa can be any naturally occurring amino acid

<400> SEQUENCE: 33

```
Val Val Lys His Ile Leu Leu Ala Arg Phe Lys Glu Asp Val Ala Pro
 1               5                  10                  15

Glu Arg Leu Asp Gln Leu Ile Arg Gly Tyr Ala Gly Leu Val Asp Leu
             20                  25                  30

Val Pro Ser Met Lys Ala Phe His Trp Gly Thr Asp Val Ser Ile Glu
         35                  40                  45

Asn Xaa Xaa Met His Gln Gly Phe Thr His Val Phe Glu Ser Thr Phe
     50                  55                  60

Glu Ser Thr Glu Gly Val Lys Glu Tyr Ile Glu His Pro Ala His Val
 65                  70                  75                  80

Glu Phe Ala Asn Glu Phe Leu Pro Val Leu Glu Lys Thr Leu Ile Ile
                 85                  90                  95

Asp Tyr
```

<210> SEQ ID NO 34
<211> LENGTH: 98
<212> TYPE: PRT
<213> ORGANISM: Triticum aestivum
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (48)..(49)
<223> OTHER INFORMATION: Xaa can be any naturally occurring amino acid

<400> SEQUENCE: 34

```
Val Val Lys His Leu Val Leu Ala Arg Phe Lys Glu Glu Ala Thr Pro
 1               5                  10                  15

Glu Ala Leu Asp Xaa Leu Ile Arg Arg Tyr Ala Gly Leu Val Asp Ala
             20                  25                  30

Val Pro Ser Met Lys Ala Phe His Trp Gly Thr Asp Val Thr Val Xaa
         35                  40                  45

Xaa Leu Asp Thr His Glu Gly Phe Thr His Val Phe Glu Ser Thr Phe
     50                  55                  60

Glu Ser Ala Glu Gly Val Lys Glu Tyr Ile Ala His Pro Ser His Val
 65                  70                  75                  80

Glu Phe Val Asp Glu Phe Leu Ala Leu Ala Glu Lys Met Leu Ile Val
                 85                  90                  95
```

Asp Tyr

<210> SEQ ID NO 35
<211> LENGTH: 109
<212> TYPE: PRT
<213> ORGANISM: Arabidopsis thaliana

<400> SEQUENCE: 35

Met Glu Glu Ala Lys Gly Pro Val Lys His Val Leu Leu Ala Ser Phe
1               5                   10                  15

Lys Asp Gly Val Ser Pro Glu Lys Ile Glu Glu Leu Ile Lys Gly Tyr
            20                  25                  30

Ala Asn Leu Val Asn Leu Ile Glu Pro Met Lys Ala Phe His Trp Gly
        35                  40                  45

Lys Asp Val Ser Ile Glu Asn Leu His Gln Gly Tyr Thr His Ile Phe
    50                  55                  60

Glu Ser Thr Phe Glu Ser Lys Glu Ala Val Ala Glu Tyr Ile Ala His
65                  70                  75                  80

Pro Ala His Val Glu Phe Ala Thr Ile Phe Leu Gly Ser Leu Asp Lys
                85                  90                  95

Val Leu Val Ile Asp Tyr Lys Pro Thr Ser Val Ser Leu
            100                 105

<210> SEQ ID NO 36
<211> LENGTH: 47
<212> TYPE: PRT
<213> ORGANISM: Arabidopsis thaliana

<400> SEQUENCE: 36

Leu His Gln Gly Tyr Thr His Ile Leu Glu Ser Thr Phe Glu Ser Lys
1               5                   10                  15

Glu Ala Val Ala Glu Tyr Ile Ala His Pro Ala His Val Glu Phe Ala
            20                  25                  30

Thr Ile Phe Leu Gly Ser Leu Asp Lys Val Leu Val Ile Asp Tyr
        35                  40                  45

<210> SEQ ID NO 37
<211> LENGTH: 98
<212> TYPE: PRT
<213> ORGANISM: Glycine max
<220> FEATURE:
<221> NAME/KEY: misc_feature
<222> LOCATION: (50)..(51)
<223> OTHER INFORMATION: Xaa can be any naturally occurring amino acid

<400> SEQUENCE: 37

Val Val Lys His Val Leu Leu Ala Lys Phe Lys Asp Asp Val Thr Pro
1               5                   10                  15

Glu Arg Ile Glu Glu Leu Ile Lys Asp Tyr Ala Asn Leu Val Asn Leu
            20                  25                  30

Ile Pro Pro Met Lys Ser Phe His Trp Gly Lys Asp Val Ser Ala Glu
        35                  40                  45

Asn Xaa Xaa Leu His Gln Gly Phe Thr His Val Phe Glu Ser Thr Phe
    50                  55                  60

Glu Ser Pro Glu Gly Val Ala Glu Tyr Val Ala His Pro Ala His Val
65                  70                  75                  80

Glu Tyr Ala Asn Leu Phe Leu Ser Cys Leu Glu Lys Val Ile Val Ile
                85                  90                  95

Asp Tyr

```
<210> SEQ ID NO 38
<211> LENGTH: 98
<212> TYPE: PRT
<213> ORGANISM: Lycopersicon esculentum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 38

Val Val Lys His Ile Leu Leu Ala Lys Phe Lys Asp Gly Ile Pro Pro
1               5                   10                  15

Glu Gln Ile Asp Gln Leu Ile Lys Gln Tyr Ala Asn Leu Val Asn Leu
            20                  25                  30

Val Glu Pro Met Lys Ala Phe Gln Trp Gly Lys Asp Val Ser Ile Glu
        35                  40                  45

Asn Xaa Xaa Leu His Gln Gly Phe Thr His Val Phe Glu Ser Thr Phe
    50                  55                  60

Asp Ser Leu Glu Gly Val Ala Glu Tyr Ile Ala His Pro Val His Val
65                  70                  75                  80

Glu Tyr Ala Asn Thr Leu Leu Pro Gln Leu Glu Lys Phe Leu Ile Val
                85                  90                  95

Asp Tyr

<210> SEQ ID NO 39
<211> LENGTH: 93
<212> TYPE: PRT
<213> ORGANISM: Glycine max
<220> FEATURE:
<221> NAME/KEY: misc_feature
<222> LOCATION: (49)..(50)
<223> OTHER INFORMATION: Xaa can be any naturally occurring amino acid

<400> SEQUENCE: 39

His Val Leu Leu Pro Lys Leu Lys Asp Tyr Phe Thr Pro Glu Arg Ile
1               5                   10                  15

Glu Leu Met Val Asp Tyr Ala Asn Leu Val Asn Leu Met Pro Arg Met
            20                  25                  30

Lys Ser Phe His Ser Gly Arg Asp Val Ser Ala Glu Tyr Leu His Leu
        35                  40                  45

Xaa Xaa Gly Cys Thr His Val Tyr Glu Ser Thr Phe Asp Ser Pro Gly
    50                  55                  60

Val Ala Glu Tyr Val Ala His Ala His Val Glu Tyr Ala Asn Gln
65                  70                  75                  80

Asp Leu Ser Cys Leu Glu Lys Val Ile Ala Ile Asp Tyr
                85                  90

<210> SEQ ID NO 40
<211> LENGTH: 108
<212> TYPE: PRT
<213> ORGANISM: Populus tremula x Populus tremuloides

<400> SEQUENCE: 40

Met Ala Thr Arg Thr Pro Lys Leu Val Lys His Thr Leu Ala Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
```

```
                35                  40                  45
Gly Thr Asp Leu Gly Met Glu Ser Ala Glu Leu Asn Arg Gly Tyr Thr
 50                  55                  60

His Ala Phe Glu Ser Thr Phe Glu Ser Lys Ser Gly Leu Gln Glu Tyr
 65                  70                  75                  80

Leu Asp Ser Ala Ala Leu Ala Ala Phe Ala Glu Gly Phe Leu Pro Thr
                 85                  90                  95

Leu Ser Gln Arg Leu Val Ile Asp Tyr Phe Leu Tyr
                100                 105

<210> SEQ ID NO 41
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 41

Lys His Leu Cys Leu Val Arg Phe Lys Glu Gly Val Val Val Glu Asp
  1               5                  10                  15

Ile Xaa Xaa Xaa Ile Glu Glu Leu Thr Lys Leu Ala Ala Glu Leu Asp
                 20                  25                  30

Thr Val Lys Phe Phe Gly Trp Gly Lys Asp Val Leu Asn Gln Glu Ala
             35                  40                  45

Xaa Leu Thr Gln Gly Phe Thr His Val Phe Ser Met Ser Phe Ala Ser
 50                  55                  60

Ala Glu Asp Leu Ala Ala Tyr Met Gly His Glu Lys His Ser Ala Phe
 65                  70                  75                  80

Ala Ala Thr Phe Met Ala Val Leu Asp Lys Val Val Leu Asp Phe
                 85                  90                  95

<210> SEQ ID NO 42
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 42

Lys His Leu Cys Leu Val Arg Phe Lys Glu Gly Val Val Val Glu Asp
  1               5                  10                  15

Ile Xaa Xaa Xaa Ile Glu Glu Leu Thr Lys Leu Ala Ala Glu Leu Asp
                 20                  25                  30

Thr Val Lys Phe Phe Gly Trp Gly Lys Asp Val Leu Asn Gln Glu Ala
             35                  40                  45

Xaa Leu Thr Gln Gly Phe Thr His Val Phe Ser Met Ser Phe Ala Ser
 50                  55                  60

Ala Glu Asp Leu Ala Ala Cys Met Gly His Glu Lys His Ser Ala Phe
 65                  70                  75                  80
```

Ala Ala Thr Phe Met Ala Val Leu Asp Lys Val Val Leu Asp Phe
            85                  90                  95

<210> SEQ ID NO 43
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 43

Lys His Leu Cys Met Ala Lys Phe Lys Glu Gly Val Val Val Glu Asp
1               5                   10                  15

Ile Xaa Xaa Xaa Ile Gln Glu Leu Thr Lys Leu Ala Ala Glu Leu Asp
                20                  25                  30

Thr Val Lys Tyr Phe Gly Trp Gly Lys Asp Val Leu Asn Gln Glu Ala
            35                  40                  45

Xaa Leu Thr Gln Gly Phe Thr His Val Phe Val Met Thr Phe Ala Ser
50                  55                  60

Ala Glu Asp Leu Ala Ala Cys Met Gly His Glu Lys His Thr Ala Phe
65                  70                  75                  80

Ala Ala Thr Phe Met Ala Ala Leu Asp Lys Val Val Val Met Asp Phe
            85                  90                  95

<210> SEQ ID NO 44
<211> LENGTH: 97
<212> TYPE: PRT
<213> ORGANISM: Oryza sativa
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 44

Val Lys His Leu Cys Leu Val Lys Phe Lys Glu Glu Val Leu Xaa Xaa
1               5                   10                  15

Xaa Val Asp Asp Ile Leu Gln Gly Met Thr Lys Leu Val Ser Glu Met
                20                  25                  30

Asp Met Val Lys Ser Phe Glu Trp Gly Lys Asp Val Xaa Leu Asn Gln
            35                  40                  45

Glu Met Leu Thr Gln Gly Phe Thr His Val Phe Ser Leu Thr Phe Ala
50                  55                  60

Ser Ser Glu Asp Leu Thr Thr Tyr Met Ser His Glu Arg His Gln Glu
65                  70                  75                  80

Phe Ala Gly Thr Phe Met Ala Ala Ile Asp Lys Val Val Val Asp
            85                  90                  95

Phe

<210> SEQ ID NO 45
<211> LENGTH: 104
<212> TYPE: PRT
<213> ORGANISM: Sorghum bicolor
<220> FEATURE:

```
<221> NAME/KEY: misc_feature
<222> LOCATION: (40)..(42)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid

<400> SEQUENCE: 45

Arg Arg Pro Thr Met Gly Glu Val Lys His Leu Cys Leu Val Lys Phe
1               5                   10                  15

Lys Glu Gly Val Val Val Glu Asp Val Leu Lys Gly Met Thr Asp Leu
            20                  25                  30

Val Ala Gly Met Asp Met Val Xaa Xaa Xaa Lys Ser Phe Glu Trp Gly
        35                  40                  45

Gln Asp Val Xaa Leu Asn Gln Glu Met Leu Thr Gln Gly Phe Thr His
    50                  55                  60

Val Phe Ser Leu Thr Phe Ala Phe Ala Asp Asp Leu Ala Thr Tyr Met
65                  70                  75                  80

Gly His Asp Arg His Ala Ala Phe Ala Ala Thr Phe Met Ala Ala Leu
                85                  90                  95

Asp Lys Val Val Val Ile Asp Phe
            100

<210> SEQ ID NO 46
<211> LENGTH: 77
<212> TYPE: PRT
<213> ORGANISM: Zea mays
<220> FEATURE:
<221> NAME/KEY: misc_feature
<222> LOCATION: (25)..(25)
<223> OTHER INFORMATION: Xaa can be any naturally occurring amino acid

<400> SEQUENCE: 46

Glu Ser Thr Phe Glu Ser Thr Glu Gly Ile Lys Glu Tyr Ile Glu His
1               5                   10                  15

Pro Ala His Val Glu Phe Ala Lys Xaa Leu Asn Gln Glu Met Leu Thr
            20                  25                  30

Gln Gly Phe Thr His Val Phe Ser Leu Thr Phe Ala Thr Ala Ala Asp
        35                  40                  45

Leu Ala Ala Tyr Met Ala His Asp Ser His Thr Ala Phe Ala Ala Thr
    50                  55                  60

Phe Met Ala Ala Ile Asp Lys Val Leu Val Val Asp Phe
65                  70                  75

<210> SEQ ID NO 47
<211> LENGTH: 97
<212> TYPE: PRT
<213> ORGANISM: Lycopersicon esculentum
<220> FEATURE:
<221> NAME/KEY: misc_feature
<222> LOCATION: (32)..(34)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid

<400> SEQUENCE: 47

Lys His Leu Val Leu Val Lys Phe Lys Glu Asp Val Val Val Glu Asp
1               5                   10                  15

Ile Leu Lys Glu Leu Glu Lys Leu Val Gln Glu Met Asp Ile Val Xaa
            20                  25                  30
```

```
Xaa Xaa Lys Ser Phe Val Trp Gly Lys Asp Val Xaa Xaa Glu Ser His
         35                  40                  45

Glu Met Leu Arg Gln Gly Phe Thr His Ala Ile Ile Met Thr Phe Asn
 50                  55                  60

Ser Lys Glu Asp Tyr Gln Thr Phe Ala Asn His Pro Asn His Val Gly
 65              70                  75                  80

Phe Ser Ala Thr Phe Ala Thr Val Ile Asp Lys Ala Val Leu Leu Asp
                 85                  90                  95

Phe

<210> SEQ ID NO 48
<211> LENGTH: 94
<212> TYPE: PRT
<213> ORGANISM: Solanum tuberosum
<220> FEATURE:
<221> NAME/KEY: misc_feature
<222> LOCATION: (29)..(31)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid

<400> SEQUENCE: 48

Leu Leu Val Lys Phe Lys Gln Asp Val Glu Glu Asp Val Leu Lys
 1               5                  10                  15

Gln Ile Glu Gln Leu Val Asn Glu Ile Asp Leu Ile Xaa Xaa Xaa Lys
             20                  25                  30

Ser Phe Val Trp Gly Lys Asp Thr Xaa Xaa Glu Ser Asn Glu Met Val
         35                  40                  45

Thr Gln Gly Tyr Thr His Ala Met Ile Met Thr Phe Asn Ser Lys Glu
 50                  55                  60

Asp Tyr Glu Ala Cys Val Val Lys Glu Val Xaa Xaa Glu Phe Ser Ala
 65              70                  75                  80

Ile Phe Val Thr Val Val Glu Lys Ile Leu Val Leu Asn Phe
                 85                  90

<210> SEQ ID NO 49
<211> LENGTH: 96
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid

<400> SEQUENCE: 49

His Tyr Val Ile Val Lys Phe Lys Asp Gly Val Ala Xaa Xaa Xaa Val
 1               5                  10                  15

Asp Asp Leu Ile Gln Gly Leu Glu Lys Met Val Phe Gly Ile Asp His
             20                  25                  30

Val Lys Ser Phe Glu Trp Gly Lys Asp Ile Xaa Xaa Glu Ser His Asp
         35                  40                  45

Met Leu Arg Gln Gly Phe Thr His Ala Phe Leu Met Thr Phe Asn Gly
```

```
                    50                  55                  60
Lys Glu Glu Phe Asn Ala Phe Gln Thr His Pro Asn His Leu Glu Phe
 65                  70                  75                  80

Ser Gly Val Phe Ser Pro Ala Ile Glu Lys Ile Val Val Leu Asp Phe
                 85                  90                  95

<210> SEQ ID NO 50
<211> LENGTH: 96
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid

<400> SEQUENCE: 50

His Tyr Val Ile Val Lys Phe Lys Asp Gly Val Ala Xaa Xaa Xaa Val
 1               5                  10                  15

Asp Glu Leu Ile Gln Gly Leu Glu Lys Met Val Ser Gly Ile Asp His
                20                  25                  30

Val Lys Ser Phe Glu Trp Gly Lys Asp Ile Xaa Xaa Glu Ser His Asp
             35                  40                  45

Met Leu Arg Gln Gly Phe Thr His Val Phe Leu Met Ala Phe Asn Gly
         50                  55                  60

Lys Glu Glu Phe Asn Ala Phe Gln Thr His Pro Asn His Leu Glu Phe
 65                  70                  75                  80

Thr Gly Val Phe Ser Pro Ala Ile Glu Lys Ile Val Val Leu Asp Phe
                 85                  90                  95

<210> SEQ ID NO 51
<211> LENGTH: 97
<212> TYPE: PRT
<213> ORGANISM: Glycine max
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid

<400> SEQUENCE: 51

Lys His Phe Val Ile Val Lys Phe Lys Glu Gly Val Ala Xaa Xaa Xaa
 1               5                  10                  15

Val Asp Glu Leu Thr Lys Gly Met Glu Lys Leu Val Thr Glu Ile Gly
                20                  25                  30

Ala Val Lys Ser Phe Glu Trp Gly Gln Asp Ile Xaa Xaa Glu Ser Leu
             35                  40                  45

Asp Val Leu Arg Gln Gly Phe Thr His Ala Phe Leu Met Thr Phe Asn
         50                  55                  60

Lys Lys Glu Asp Phe Val Ala Phe Gln Ser His Pro Asn His Val Glu
 65                  70                  75                  80

Phe Ser Thr Lys Phe Ser Ala Ala Ile Glu Asn Ile Val Leu Leu Asp
                 85                  90                  95

Phe
```

-continued

```
<210> SEQ ID NO 52
<211> LENGTH: 43
<212> TYPE: PRT
<213> ORGANISM: Glycine max
<220> FEATURE:
<221> NAME/KEY: misc_feature
<222> LOCATION: (18)..(19)
<223> OTHER INFORMATION: Xaa can be any naturally occurring amino acid

<400> SEQUENCE: 52

Leu Val Ser Glu Ile His Ala Val Lys Ser Phe Glu Trp Gly Gln Asp
1               5                   10                  15

Ile Xaa Xaa Glu Ser Leu Asp Val Leu Arg Gln Gly Phe Thr His Ala
            20                  25                  30

Phe Leu Met Thr Phe Asn Lys Lys Arg Arg Leu
        35                  40

<210> SEQ ID NO 53
<211> LENGTH: 111
<212> TYPE: PRT
<213> ORGANISM: Arabidopsis thaliana

<400> SEQUENCE: 53

Met Ala Thr Ser Gly Phe Lys His Leu Val Val Lys Phe Lys Glu
1               5                   10                  15

Asp Thr Lys Val Asp Glu Ile Leu Lys Gly Leu Glu Asn Leu Val Ser
            20                  25                  30

Gln Ile Asp Thr Val Lys Ser Phe Glu Trp Gly Glu Asp Lys Glu Ser
        35                  40                  45

His Asp Met Leu Arg Gln Gly Phe Thr His Ala Phe Ser Met Thr Phe
    50                  55                  60

Glu Asn Lys Asp Gly Tyr Val Ala Phe Thr Ser His Pro Leu His Val
65                  70                  75                  80

Glu Phe Ser Ala Ala Phe Thr Ala Val Ile Asp Lys Ile Val Leu Leu
                85                  90                  95

Asp Phe Pro Val Ala Ala Val Lys Ser Ser Val Val Ala Thr Pro
            100                 105                 110

<210> SEQ ID NO 54
<211> LENGTH: 100
<212> TYPE: PRT
<213> ORGANISM: Glycine max
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid

<400> SEQUENCE: 54

Lys Thr Val Glu His Ile Val Leu Phe Lys Val Lys Glu Glu Thr Glu
1               5                   10                  15

Pro Ser Lys Val Ser Asp Met Val Asn Gly Leu Gly Ser Leu Val Ser
            20                  25                  30

Leu Asp Pro Val Leu His Xaa Leu Ser Val Gly Pro Leu Leu Arg Asn
        35                  40                  45

Arg Ser Ser Ala Leu Thr Xaa Xaa Phe Thr His Met Leu His Ser Arg
    50                  55                  60

Tyr Lys Ser Lys Glu Asp Leu Glu Ala Tyr Ser Ala His Pro Ser His
65                  70                  75                  80
```

Val Ser Val Val Lys Gly Tyr Val Leu Pro Ile Ile Asp Asp Ile Met
            85                  90                  95

Ser Val Asp Trp
            100

<210> SEQ ID NO 55
<211> LENGTH: 352
<212> TYPE: DNA
<213> ORGANISM: Artificial sequence
<220> FEATURE:
<223> OTHER INFORMATION: mtbSP coding sequence

<400> SEQUENCE: 55
aaaacatatg cgcaaacttc cggatgcggc aaccagaact ccaaagcttg tgaagcacac     60
attgttgact cggttcaagg atgagatcac acgagaacag atcgacaact acattaatga    120
ctataccaat ctgctcgatc tcattccaag catgaagagt ttcaattggg gcacggatct    180
gggcatggag tctgcggagc taaaccgagg atacactcat gcctttgaat ctacatttga    240
gagcaagtct ggtttgcaag agtacctcga ttctgctgct cttgctgcat ttgcagaagg    300 gttttttgcct actttgtcac agcgtcttgt gatagactac tttctctact aa           352

<210> SEQ ID NO 56
<211> LENGTH: 383
<212> TYPE: DNA
<213> ORGANISM: Artificial sequence
<220> FEATURE:
<223> OTHER INFORMATION: L1-SP1 coding sequence

<400> SEQUENCE: 56
aaggagatat acaaaaacat atgcactggt cagcatggtg atacgatca aatcaatcag      60 caaccagaac tccaaagctt gtgaagcaca cattgttgac tcggttcaag gatgagatca   120
cacgagaaca gatcgacaac tacattaatg actataccaa tctgctcgat ctcattccaa   180
gcatgaagag tttcaattgg ggcacggatc tgggcatgga gtctgcggag ctaaaccgag   240
gatacactca tgcctttgaa tctacatttg agagcaagtc tggtttgcaa gagtacctcg   300
attctgctgc tcttgctgca tttgcagaag ggttttttgcc tactttgtca cagcgtcttg   360
tgatagacta ctttctctac taa                                            383

<210> SEQ ID NO 57
<211> LENGTH: 384
<212> TYPE: DNA
<213> ORGANISM: Artificial sequence
<220> FEATURE:
<223> OTHER INFORMATION: L2-Sp1 coding sequence

<400> SEQUENCE: 57
gaaggagata tacaaaaaca tatgcactca tcatactggt acgcattcaa caacaaaaca     60
gcaaccagaa ctccaaagct tgtgaagcac acattgttga ctcggttcaa ggatgagatc    120
acacgagaac agatcgacaa ctacattaat gactatacca atctgctcga tctcattcca    180
agcatgaaga gtttcaattg ggcacggat ctgggcatgg agtctgcgga gctaaaccga     240
ggatacactc atgcctttga atctacattt gagagcaagt ctggtttgca agagtacctc    300
gattctgctg ctcttgctgc atttgcagaa gggttttttgc ctactttgtc acagcgtctt   360
gtgatagact actttctcta ctaa                                           384

<210> SEQ ID NO 58

<210> SEQ ID NO 58
<211> LENGTH: 375
<212> TYPE: DNA
<213> ORGANISM: Artificial sequence
<220> FEATURE:
<223> OTHER INFORMATION: L3-SP1 coding sequence

<400> SEQUENCE: 58

```
atacaaaaac atatggatta tttttcatca ccatattatg aacaattatt tgcaaccaga    60
actccaaagc ttgtgaagca cacattgttg actcggttca aggatgagat cacacgagaa   120
cagatcgaca actacattaa tgactatacc aatctgctcg atctcattcc aagcatgaag   180
agtttcaatt ggggcacgga tctgggcatg gagtctgcgg agctaaaccg aggatacact   240
catgcctttg aatctacatt tgagagcaag tctggtttgc aagagtacct cgattctgct   300
gctcttgctg catttgcaga agggtttttg cctactttgt cacagcgtct tgtgatagac   360
tactttctct actaa                                                    375
```

<210> SEQ ID NO 59
<211> LENGTH: 361
<212> TYPE: DNA
<213> ORGANISM: Artificial sequence
<220> FEATURE:
<223> OTHER INFORMATION: L6-SP1 coding sequence

<400> SEQUENCE: 59

```
agaaggagat atacaaaaac atatgtcaaa tcaatcagca accagaactc caaagcttgt    60
gaagcacaca ttgttgactc ggttcaagga tgagatcaca cgagaacaga tcgacaacta   120
cattaatgac ataccaatc tgctcgatct cattccaagc atgaagagtt caattgggg    180
cacggatctg gcatggagt ctgcggagct aaaccgagga tacactcatg cctttgaatc   240
tacatttgag agcaagtctg gtttgcaaga gtacctcgat tctgctgctc ttgctgcatt   300
tgcagaaggg ttttgccta ctttgtcaca gcgtcttgtg atagactact ttctctacta   360
a                                                                   361
```

<210> SEQ ID NO 60
<211> LENGTH: 383
<212> TYPE: DNA
<213> ORGANISM: Artificial sequence
<220> FEATURE:
<223> OTHER INFORMATION: L4-Sp1 coding sequence

<400> SEQUENCE: 60

```
aaggagatat acaaaaacat atgcactggt cagcatggtg gatacgatca aatcaatcag    60
caaccagaac tccaaagctt gtgaagcaca cattgttgac tcggttcaag gatgagatca   120
caaaagaaca gatcgacaac tacattaatg actataccaa tctgctcgat ctcattccaa   180
gcatgaagag tttcaattgg ggcacggatc tgggcatgga gtctgcggag ctaaaccgag   240
gatacactca tgcctttgaa tctacatttg agagcaagtc tggtttgcaa gagtacctcg   300
attctgctgc tcttgctgca tttgcagaag ggttttttgcc tactttgtca cagcgtcttg   360
tgatagacta ctttctctac taa                                           383
```

<210> SEQ ID NO 61
<211> LENGTH: 383
<212> TYPE: DNA
<213> ORGANISM: Artificial sequence
<220> FEATURE:
<223> OTHER INFORMATION: L5-Sp1 coding sequence

<400> SEQUENCE: 61

```
aaggagatat acaaaaacat atgcactggt cagcatggtg gatacgatca aatcaatcag    60
caaccagaac tccaaagctt gtgaagcaca cattgttgac tcggttcaag gatgagatct   120
gccgagaaca gatcgacaac tacattaatg actataccaa tctgctcgat ctcattccaa   180
gcatgaagag tttcaattgg ggcacggatc tgggcatgga gtctgcggag ctaaaccgag   240
gatacactca tgcctttgaa tctacatttg agagcaagtc tggtttgcaa gagtacctcg   300
attctgctgc tcttgctgca tttgcagaag ggttttgcc tactttgtca cagcgtcttg    360
tgatagacta ctttctctac taa                                          383
```

<210> SEQ ID NO 62
<211> LENGTH: 383
<212> TYPE: DNA
<213> ORGANISM: Artificial sequence
<220> FEATURE:
<223> OTHER INFORMATION: L7-SP1 coding sequence

<400> SEQUENCE: 62

```
aaggagatat acaaaaacat atgcactggt cagcatggtg gattcgttca aatcaatcag    60
caaccagaac tccaaagctt gtgaagcaca cattgttgac tcggttcaag gatgagatca   120
cacgagaaca gatcgacaac tacattaatg actataccaa tctgctcgat ctcattccaa   180
gcatgaagag tttcaattgg ggcacggatc tgggcatgga gtctgcggag ctaaaccgag   240
gatacactca tgcctttgaa tctacatttg agagcaagtc tggtttgcaa gagtacctcg   300
attctgctgc tcttgctgca tttgcagaag ggttttgcc tactttgtca cagcgtcttg    360
tgatagacta ctttctctac taa                                          383
```

<210> SEQ ID NO 63
<211> LENGTH: 383
<212> TYPE: DNA
<213> ORGANISM: Artificial sequence
<220> FEATURE:
<223> OTHER INFORMATION: L8_Sp1 coding sequence

<400> SEQUENCE: 63

```
aaggagatat acaaaaacat atgcactggt cagcatggtg gattcgttca aatcaatcag    60
caaccagaac tccaaagctt gtgaagcaca cattgttgac tcggttcaag gatgagatca   120
caaaagaaca gatcgacaac tacattaatg actataccaa tctgctcgat ctcattccaa   180
gcatgaagag tttcaattgg ggcacggatc tgggcatgga gtctgcggag ctaaaccgag   240
gatacactca tgcctttgaa tctacatttg agagcaagtc tggtttgcaa gagtacctcg   300
attctgctgc tcttgctgca tttgcagaag ggttttgcc tactttgtca cagcgtcttg    360
tgatagacta ctttctctac taa                                          383
```

<210> SEQ ID NO 64
<211> LENGTH: 103
<212> TYPE: PRT
<213> ORGANISM: Artificial sequence
<220> FEATURE:
<223> OTHER INFORMATION: Sp1 mutant variant: amino acid 2-6 deleted

<400> SEQUENCE: 64

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

```
Asp Leu Ile Pro Ser Met Lys Ser Phe Asn Trp Gly Thr Asp Leu Gly
             35                  40                  45

Met Glu Ser Ala Glu Leu Asn Arg Gly Tyr Thr His Ala Phe Glu Ser
 50                  55                  60

Thr Phe Glu Ser Lys Ser Gly Leu Gln Glu Tyr Leu Asp Ser Ala Ala
 65                  70                  75                  80

Leu Ala Ala Phe Ala Glu Gly Phe Leu Pro Thr Leu Ser Gln Arg Leu
                 85                  90                  95

Val Ile Asp Tyr Phe Leu Tyr
            100
```

<210> SEQ ID NO 65
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 65
ctgctcgatc tcattccaag ctgtaagagt ttcaattggg gcacg        45

<210> SEQ ID NO 66
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 66
gcaagtctgg tttgcaagag tactgcgatt ctgctgctct tgctg        45

<210> SEQ ID NO 67
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 67
aaaacatatg cgcaaacttc cggatgcggc aaccagaact ccaaagcttg        50

<210> SEQ ID NO 68
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 68
aaaagagctc ttagtaaaga agtaatcaa taac        34

<210> SEQ ID NO 69
<211> LENGTH: 312
<212> TYPE: DNA
<213> ORGANISM: Artificial sequence
<220> FEATURE:
<223> OTHER INFORMATION: M43C delta N' SP1 coding sequence

<400> SEQUENCE: 69
atgaagcttg tgaagcacac attgttgact cggttcaagg atgagatcac acgagaacag        60
atcgacaact acattaatga ctataccaat ctgctcgatc tcattccaag ctgtaagagt        120
ttcaattggg gcacggatct gggcatggag tctgcggagc taaaccgagg atacactcat        180

```
gcctttgaat ctacatttga gagcaagtct ggtttgcaag agtacctcga ttctgctgct    240
cttgctgcat ttgcagaagg gttttttgcct actttgtcac agcgtcttgt gatagactac    300
tttctctact aa                                                        312
```

```
<210> SEQ ID NO 70
<211> LENGTH: 77
<212> TYPE: DNA
<213> ORGANISM: Artificial sequence
<220> FEATURE:
<223> OTHER INFORMATION: Single strand DNA oligonucleotide

<400> SEQUENCE: 70
aaggagatat acaaaaacat atgcactggt cagcatggtg gatacgatca aatcaatcag    60
caaccagaac tccaaag                                                   77
```

```
<210> SEQ ID NO 71
<211> LENGTH: 77
<212> TYPE: DNA
<213> ORGANISM: Artificial sequence
<220> FEATURE:
<223> OTHER INFORMATION: Single strand DNA oligonucleotide

<400> SEQUENCE: 71
ctttggagtt ctggttgctg attgatttga tcgtatccac catgctgacc agtgcatatg    60 ttttttgtata tctcctt                                                  77
```

```
<210> SEQ ID NO 72
<211> LENGTH: 80
<212> TYPE: DNA
<213> ORGANISM: Artificial sequence
<220> FEATURE:
<223> OTHER INFORMATION: Single strand DNA oligonucleotide

<400> SEQUENCE: 72
agaaggagat atacaaaaac atatgcactc atcatactgg tacgcattca acaacaaaac    60
agcaaccaga actccaaagc                                                80
```

```
<210> SEQ ID NO 73
<211> LENGTH: 80
<212> TYPE: DNA
<213> ORGANISM: Artificial sequence
<220> FEATURE:
<223> OTHER INFORMATION: Single strand DNA oligonucleotide

<400> SEQUENCE: 73
gctttggagt tctggttgct gttttgttgt tgaatgcgta ccagtatgat gagtgcatat    60 gttttttgtat atctccttct                                               80
```

```
<210> SEQ ID NO 74
<211> LENGTH: 65
<212> TYPE: DNA
<213> ORGANISM: Artificial sequence
<220> FEATURE:
<223> OTHER INFORMATION: Single strand DNA oligonucleotide

<400> SEQUENCE: 74
atacaaaaac atatggatta tttttcatca ccatattatg aacaattatt tgcaaccaga    60
actcc                                                                65
```

```
<210> SEQ ID NO 75
<211> LENGTH: 65
```

```
<212> TYPE: DNA
<213> ORGANISM: Artificial sequence
<220> FEATURE:
<223> OTHER INFORMATION: Single strand DNA oligonucleotide

<400> SEQUENCE: 75
ggagttctgg ttgcaaataa ttgttcataa tatggtgatg aaaaataatc catatgtttt      60
tgtat                                                                  65

<210> SEQ ID NO 76
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 76
agaaggagat atacaaaaac atatgtcaaa tcaatcagca accagaactc caaagc          56

<210> SEQ ID NO 77
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 77
gctttggagt tctggttgct gattgatttg acatatgttt ttgtatatct ccttct          56

<210> SEQ ID NO 78
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 78
actggtcagc atggtggatt cgatcaaatc aatcag                                36

<210> SEQ ID NO 79
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 79
ctgattgatt tgatcgaatc caccatgctg accagt                                36

<210> SEQ ID NO 80
<211> LENGTH: 37
<212> TYPE: DNA
<213> ORGANISM: Artificial sequence
<220> FEATURE:
<223> OTHER INFORMATION: Single strand DNA oligonucleotide

<400> SEQUENCE: 80
gtcagcatgg tggattcgtt caaatcaatc agcaacc                               37

<210> SEQ ID NO 81
<211> LENGTH: 37
<212> TYPE: DNA
<213> ORGANISM: Artificial sequence
<220> FEATURE:
<223> OTHER INFORMATION: Single strand DNA oligonucleotide
```

<400> SEQUENCE: 81
ggttgctgat tgatttgaac gaatccacca tgctgac        37

<210> SEQ ID NO 82
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 82
tgactcggtt caaggatgag atcacaaaag aacagatcga ca        42

<210> SEQ ID NO 83
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 83
tgtcgatctg ttcttttgtg atctcatcct tgaaccgagt ca        42

<210> SEQ ID NO 84
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 84
actcggttca aggatgagat ctgccgagaa cagatcgaca actac        45

<210> SEQ ID NO 85
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 85
gtagttgtcg atctgttctc ggcagatctc atccttgaac cgagt        45

<210> SEQ ID NO 86
<211> LENGTH: 301
<212> TYPE: PRT
<213> ORGANISM: Artificial sequence
<220> FEATURE:
<223> OTHER INFORMATION: SP1-CBD chimeric polypeptide

<400> SEQUENCE: 86

Met Ala Ala Thr Ser Ser Met Ser Val Glu Phe Tyr Asn Ser Asn Lys
1               5                   10                  15

Ser Ala Gln Thr Asn Ser Ile Thr Pro Ile Ile Lys Ile Thr Asn Thr
            20                  25                  30

Ser Asp Ser Asp Leu Asn Leu Asn Asp Val Lys Val Arg Tyr Tyr Tyr

```
Val Glu Phe Gly Phe Ala Ser Gly Arg Ala Thr Leu Lys Lys Gly Gln
                100                 105                 110

Phe Ile Thr Ile Gln Gly Arg Ile Thr Lys Ser Asp Trp Ser Asn Tyr
            115                 120                 125

Thr Gln Thr Asn Asp Tyr Ser Phe Asp Ala Ser Ser Thr Pro Val
        130                 135                 140

Val Asn Pro Lys Val Thr Gly Tyr Ile Gly Gly Ala Lys Val Leu Gly
145                 150                 155                 160

Thr Ala Pro Ala Val Pro Ser Gly Ser Val Thr Ser Ser Lys Thr
                165                 170                 175

Thr Thr Thr Ala Ser Lys Thr Ser Thr Ser Ser Thr Ser Glu
            180                 185                 190

Phe Met Ala Thr Ser Thr Pro Lys Leu Val Lys His Thr Leu Leu Thr
                195                 200                 205

Arg Phe Lys Asp Glu Ile Thr Arg Glu Gln Ile Asp Asn Tyr Ile Asn
            210                 215                 220

Asp Tyr Thr Asn Leu Leu Asp Leu Ile Pro Ser Met Lys Ser Phe Asn
225                 230                 235                 240

Trp Gly Thr Asp Leu Gly Met Glu Ser Ala Glu Leu Asn Arg Gly Tyr
                245                 250                 255

Thr His Ala Phe Glu Ser Thr Phe Glu Ser Lys Ser Gly Leu Gln Glu
            260                 265                 270

Tyr Leu Asp Ser Ala Ala Leu Ala Ala Phe Ala Glu Gly Phe Leu Pro
                275                 280                 285

Thr Leu Ser Gln Arg Leu Val Ile Asp Tyr Phe Leu Tyr
        290                 295                 300

<210> SEQ ID NO 87
<211> LENGTH: 163
<212> TYPE: PRT
<213> ORGANISM: Artificial sequence
<220> FEATURE:
<223> OTHER INFORMATION: CBD domain

<400> SEQUENCE: 87

Met Ala Ala Thr Ser Ser Met Ser Val Glu Phe Tyr Asn Ser Asn Lys
1               5                   10                  15

Ser Ala Gln Thr Asn Ser Ile Thr Pro Ile Ile Lys Ile Thr Asn Thr
            20                  25                  30

Ser Asp Ser Asp Leu Asn Leu Asn Asp Val Lys Val Arg Tyr Tyr Tyr
        35                  40                  45

Thr Ser Asp Gly Thr Gln Gly Gln Thr Phe Trp Cys Asp His Ala Gly
    50                  55                  60

Ala Leu Leu Gly Asn Ser Tyr Val Asp Asn Thr Ser Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Arg Ala Thr Leu Lys Lys Gly Gln
                100                 105                 110

Phe Ile Thr Ile Gln Gly Arg Ile Thr Lys Ser Asp Trp Ser Asn Tyr
            115                 120                 125

Thr Gln Thr Asn Asp Tyr Ser Phe Asp Ala Ser Ser Thr Pro Val
        130                 135                 140

Val Asn Pro Lys Val Thr Gly Tyr Ile Gly Gly Ala Lys Val Leu Gly
145                 150                 155                 160
```

```
Thr Ala Pro

<210> SEQ ID NO 88
<211> LENGTH: 108
<212> TYPE: PRT
<213> ORGANISM: Artificial sequence
<220> FEATURE:
<223> OTHER INFORMATION: Sp1 polypeptide

<400> SEQUENCE: 88

Met Ala Thr Ser Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
                20                  25                  30

Tyr Thr Asn Leu Leu Asp Leu Ile Pro Ser Met Lys Ser Phe Asn Trp
            35                  40                  45

Gly Thr Asp Leu Gly Met Glu Ser Ala Glu Leu Asn Arg Gly Tyr Thr
        50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
                100                 105

<210> SEQ ID NO 89
<211> LENGTH: 30
<212> TYPE: PRT
<213> ORGANISM: Artificial sequence
<220> FEATURE:
<223> OTHER INFORMATION: SP1-CBD fusion protein peptide linker.

<400> SEQUENCE: 89

Ala Val Pro Ser Gly Ser Val Thr Ser Thr Ser Lys Thr Thr Thr Thr
1               5                   10                  15

Ala Ser Lys Thr Ser Thr Ser Thr Ser Ser Thr Ser Glu Phe
                20                  25                  30
```